United States Patent
Tipler

(10) Patent No.: US 9,983,104 B2
(45) Date of Patent: May 29, 2018

(54) FLOW CONTROL DEVICES AND THEIR USE WITH EXPLOSIVE CARRIER GASES

(71) Applicant: Andrew Tipler, Trumbull, CT (US)

(72) Inventor: Andrew Tipler, Trumbull, CT (US)

(73) Assignee: PerkinElmer Health Sciences, Inc., Waltham, MA (US)

(*) Notice: Subject to any disclaimer, the term of this patent is extended or adjusted under 35 U.S.C. 154(b) by 249 days.

(21) Appl. No.: 14/634,856

(22) Filed: Mar. 1, 2015

(65) Prior Publication Data
US 2015/0268137 A1 Sep. 24, 2015

Related U.S. Application Data

(63) Continuation of application No. 13/351,892, filed on Jan. 17, 2012, now Pat. No. 8,966,957.

(60) Provisional application No. 61/433,783, filed on Jan. 18, 2011.

(51) Int. Cl.
| | |
|---|---|
| *G01N 1/00* | (2006.01) |
| *G01N 1/22* | (2006.01) |
| *G01N 27/62* | (2006.01) |
| *G01N 30/28* | (2006.01) |
| *G01N 30/02* | (2006.01) |

(52) U.S. Cl.
CPC ......... *G01N 1/2226* (2013.01); *G01N 27/626* (2013.01); *G01N 30/28* (2013.01); *G01N 2001/2229* (2013.01); *G01N 2030/025* (2013.01)

(58) Field of Classification Search
CPC .. G01N 2030/025; G01N 30/88; G01N 30/74; G01N 2030/8854; G01N 30/72; G01N 1/2226; G01N 30/28; G01N 27/626

USPC .............................. 73/23.41, 23.22, 23.35
See application file for complete search history.

(56) References Cited

U.S. PATENT DOCUMENTS

| | | | |
|---|---|---|---|
| 4,422,860 A | 12/1983 | Feinstein | |
| 4,704,141 A | 11/1987 | Krebber | |
| 5,363,707 A * | 11/1994 | Augenblick | G01N 30/06 73/863.81 |
| 5,711,789 A | 1/1998 | Hinshaw | |
| 5,952,556 A * | 9/1999 | Shoji | G01N 30/32 422/89 |
| 7,013,707 B2 * | 3/2006 | Prohaska | G01N 27/4045 204/421 |
| 7,343,779 B1 * | 3/2008 | Yu | G01N 30/08 422/89 |

(Continued)

FOREIGN PATENT DOCUMENTS

WO 2004009202 1/2004

OTHER PUBLICATIONS

Extended European Search Report for EP12736362.0 dated Oct. 26, 2017.

*Primary Examiner* — Eric S McCall
*Assistant Examiner* — Mohammed E Keramet-Amircola
(74) *Attorney, Agent, or Firm* — Rhodes IP PLC; Christopher R Rhodes

(57) ABSTRACT

Certain embodiments described herein are directed to devices, systems and methods that are configured to control flow of an explosive carrier gas in a sampling system. In some examples, a flow control device configured to provide release of explosive carrier gas in less than an explosive amount to void space in the sampling system is described. Systems and methods using the flow control device are also disclosed.

20 Claims, 85 Drawing Sheets

(56) References Cited

U.S. PATENT DOCUMENTS

| | | | | |
|---|---|---|---|---|
| 8,114,200 B2* | 2/2012 | Alm | .................. | G01N 30/463 |
| | | | | 73/23.35 |
| 8,322,189 B2* | 12/2012 | Wang | .................. | G01N 30/463 |
| | | | | 73/23.22 |
| 8,943,872 B2* | 2/2015 | Liu | .................. | G01N 30/461 |
| | | | | 73/23.35 |
| 2003/0106363 A1* | 6/2003 | Sacks | .................. | G01N 30/32 |
| | | | | 73/23.35 |
| 2003/0109054 A1* | 6/2003 | Sacks | .................. | G01N 30/32 |
| | | | | 436/161 |
| 2006/0099716 A1* | 5/2006 | Tipler | .................. | G01N 30/16 |
| | | | | 436/161 |
| 2008/0105033 A1* | 5/2008 | Tipler | .................. | G01N 30/30 |
| | | | | 73/23.42 |
| 2010/0101411 A1* | 4/2010 | Tipler | .................. | G01N 30/20 |
| | | | | 95/86 |
| 2011/0308298 A1* | 12/2011 | Magni | .................. | G01N 30/32 |
| | | | | 73/23.35 |

* cited by examiner

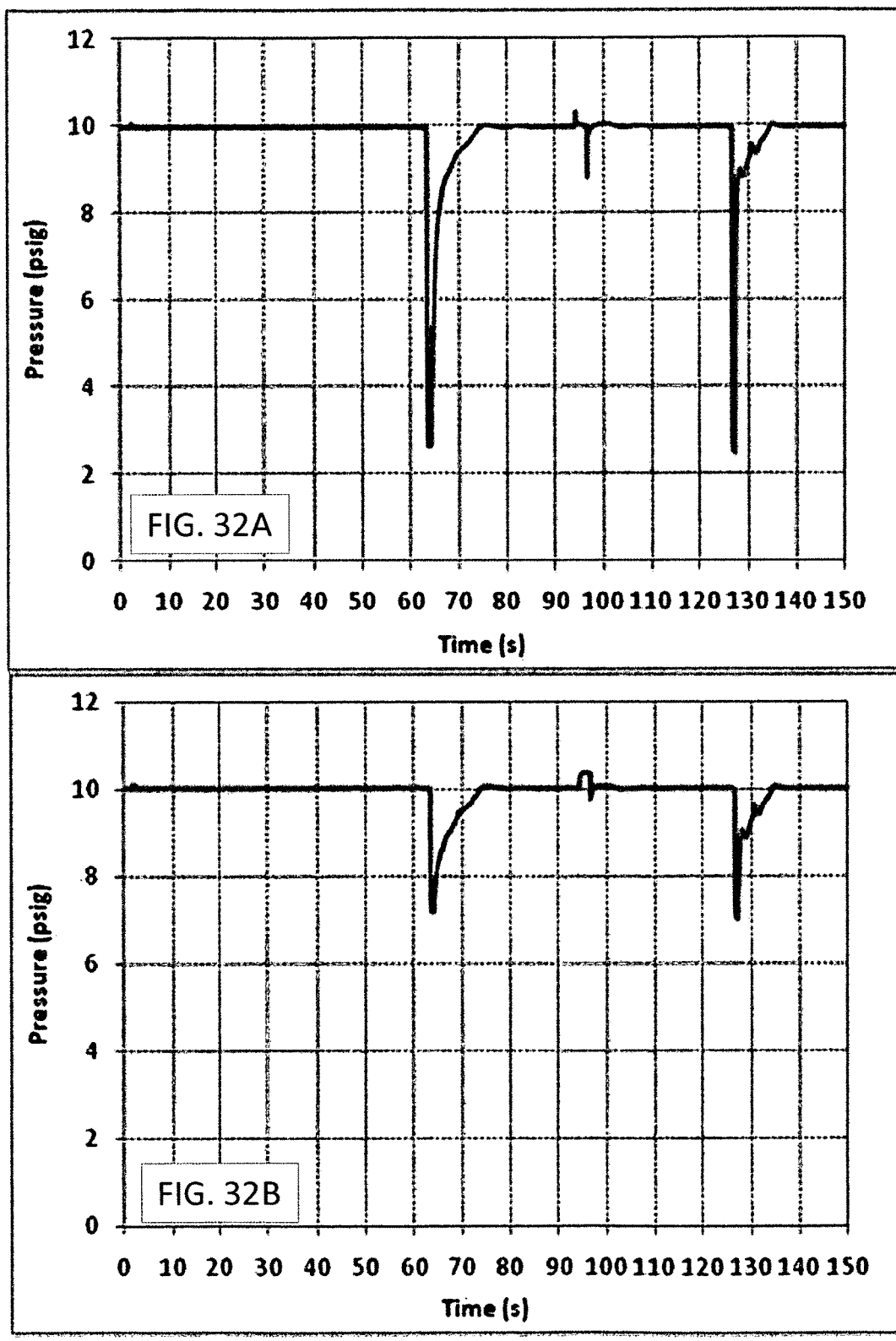

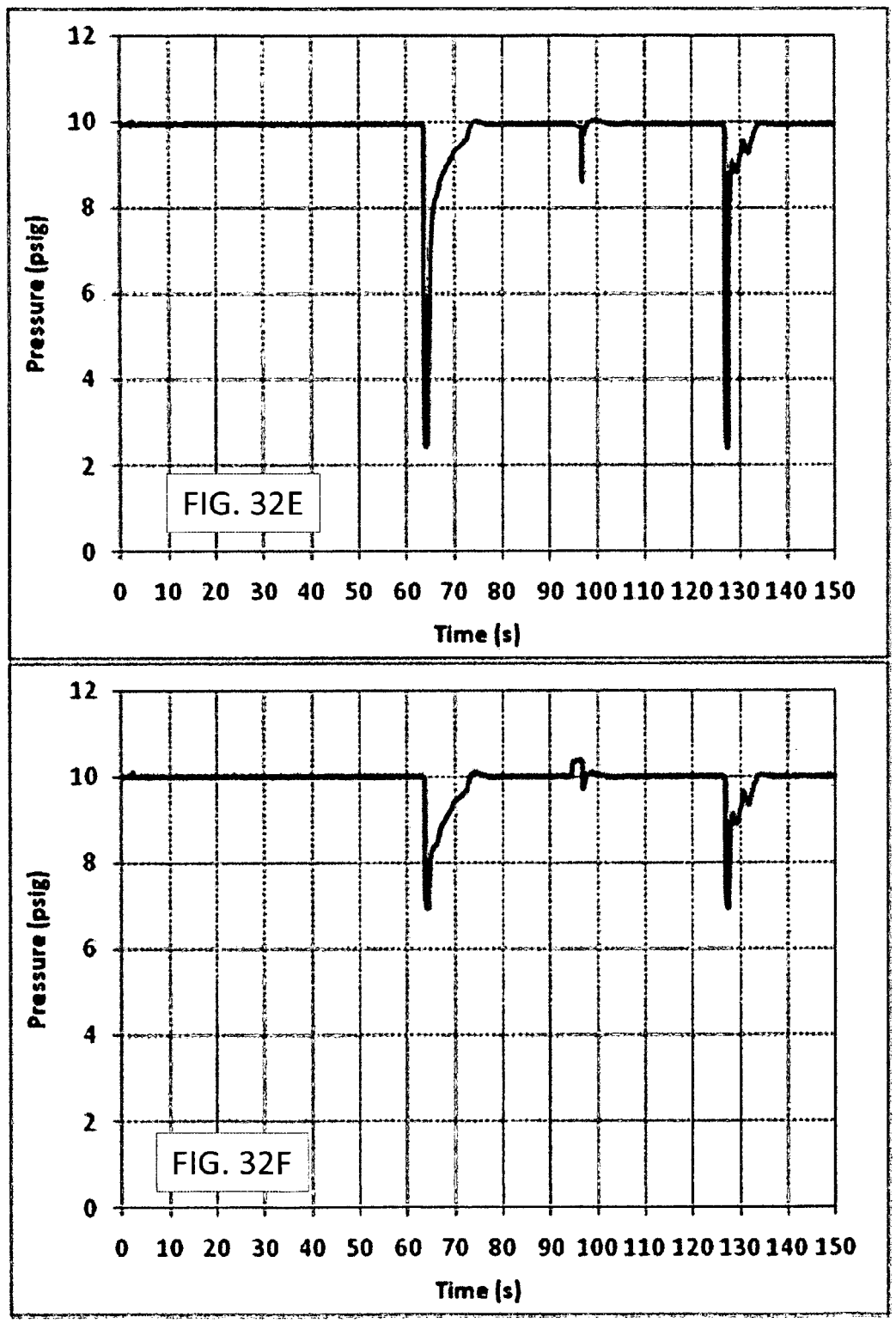

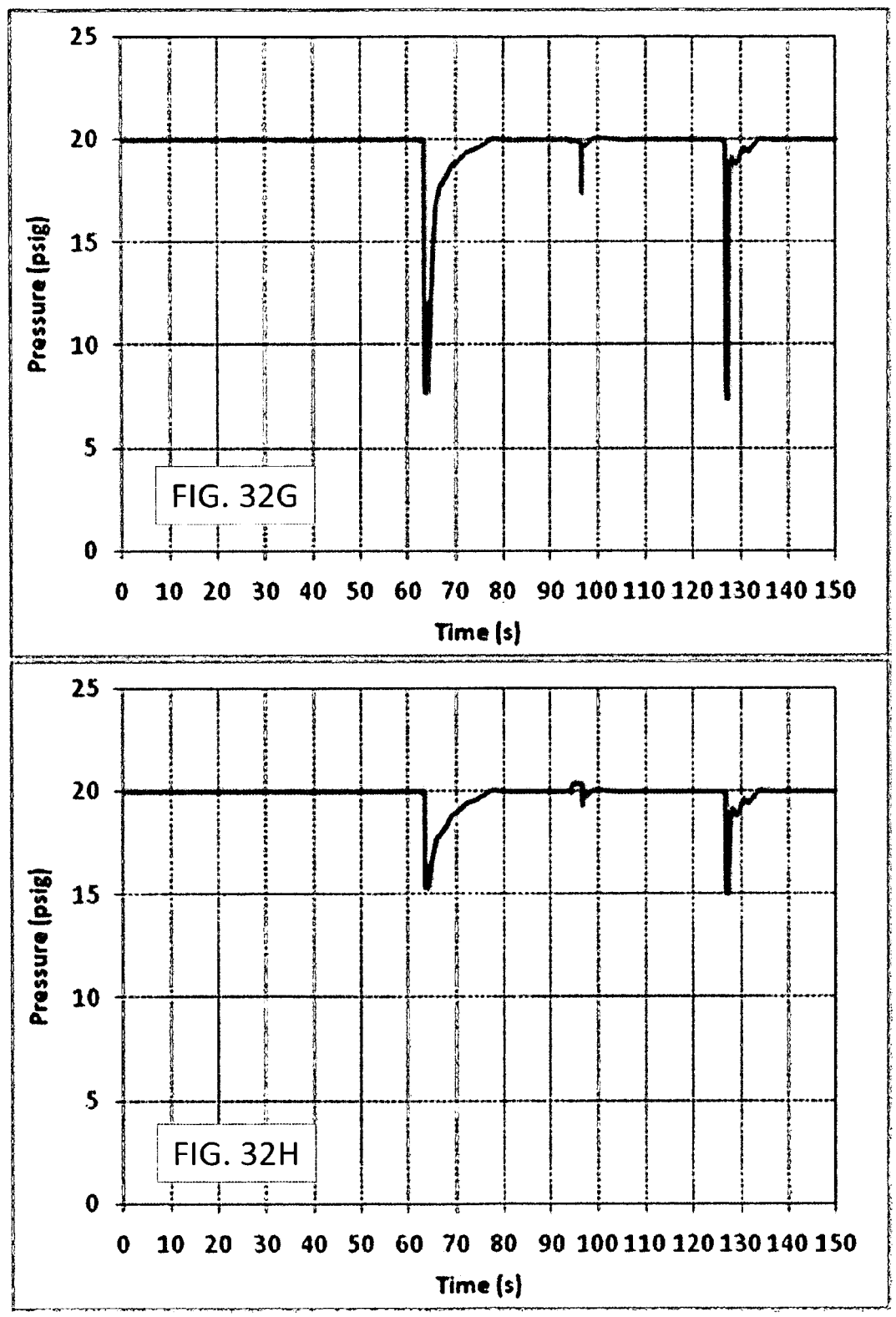

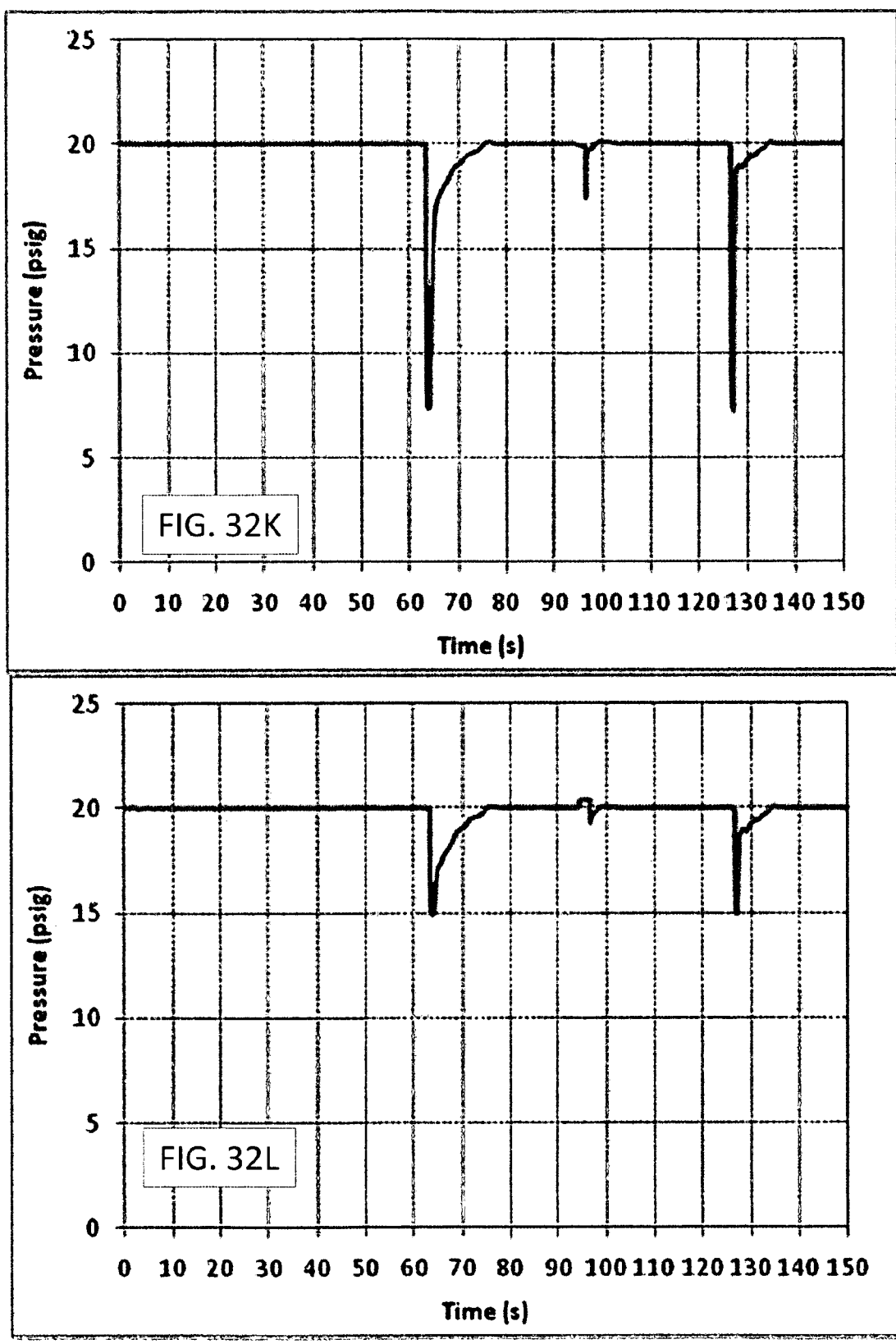

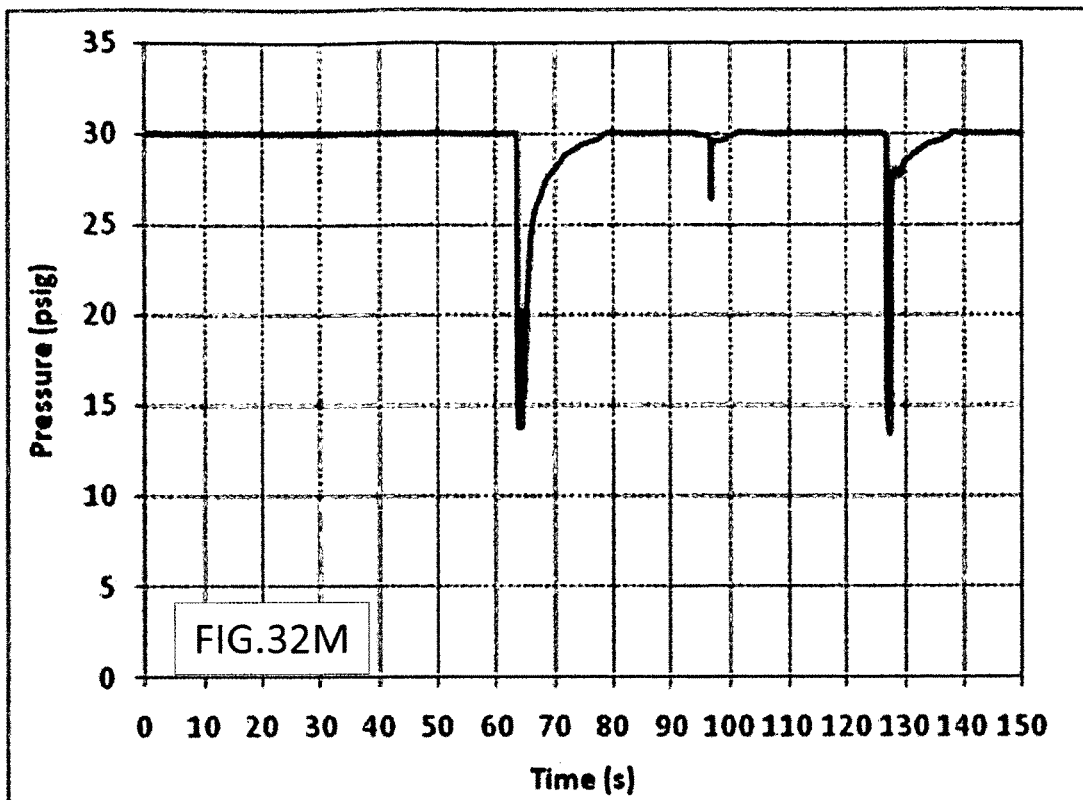
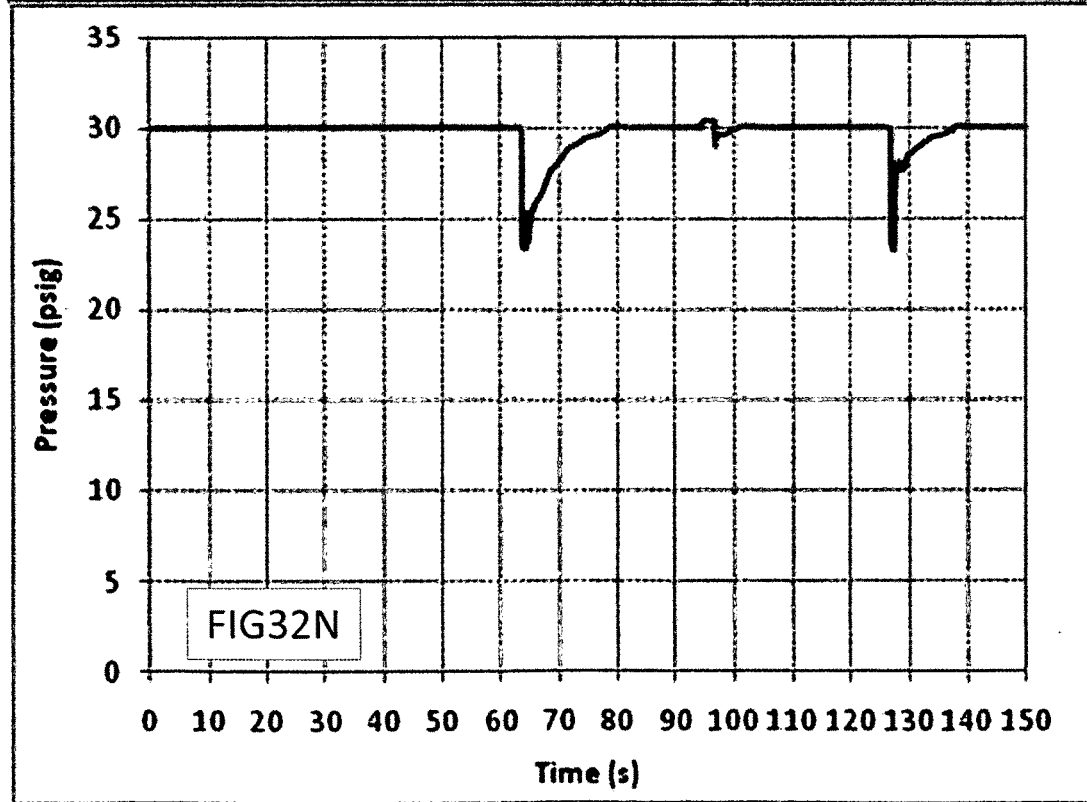

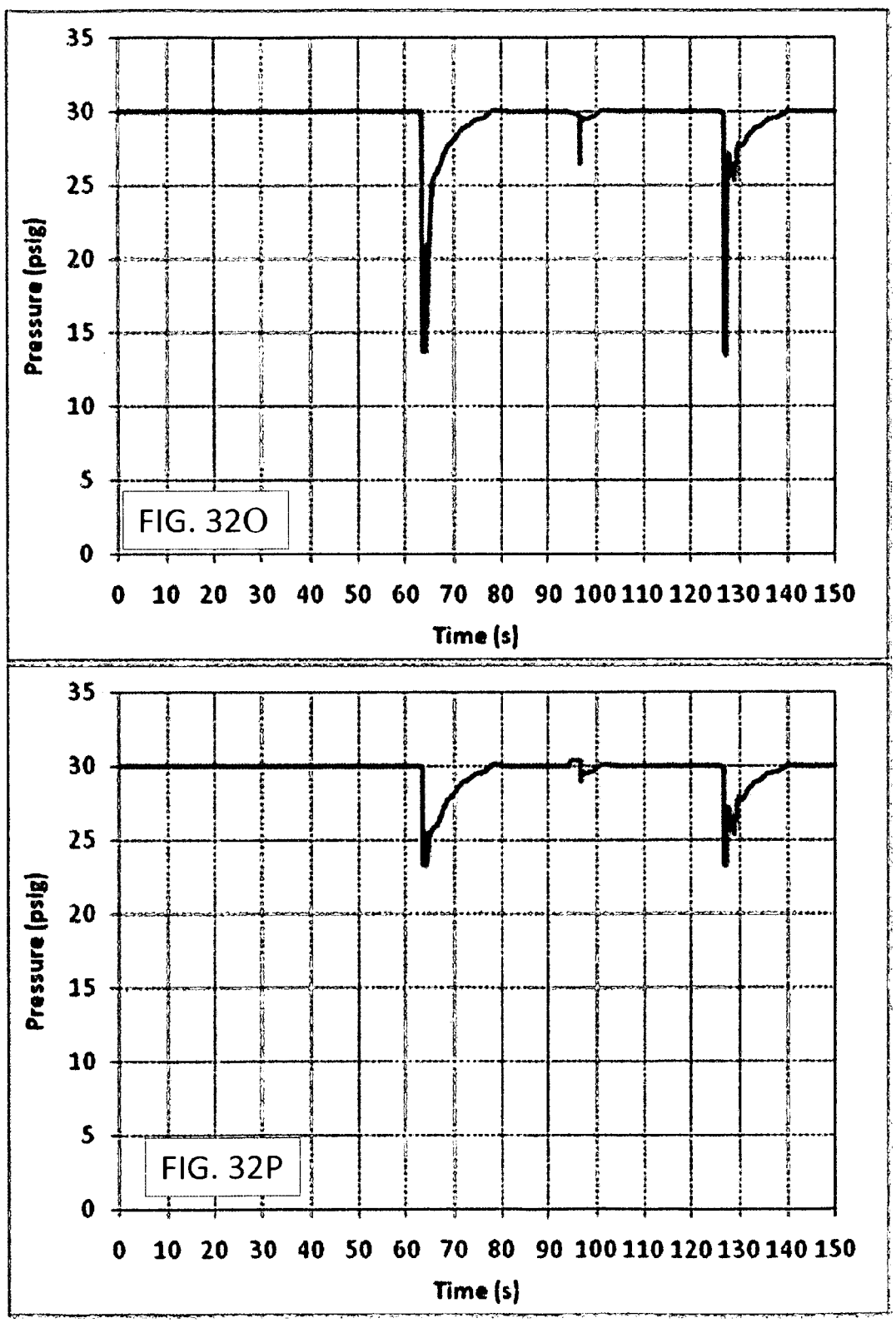

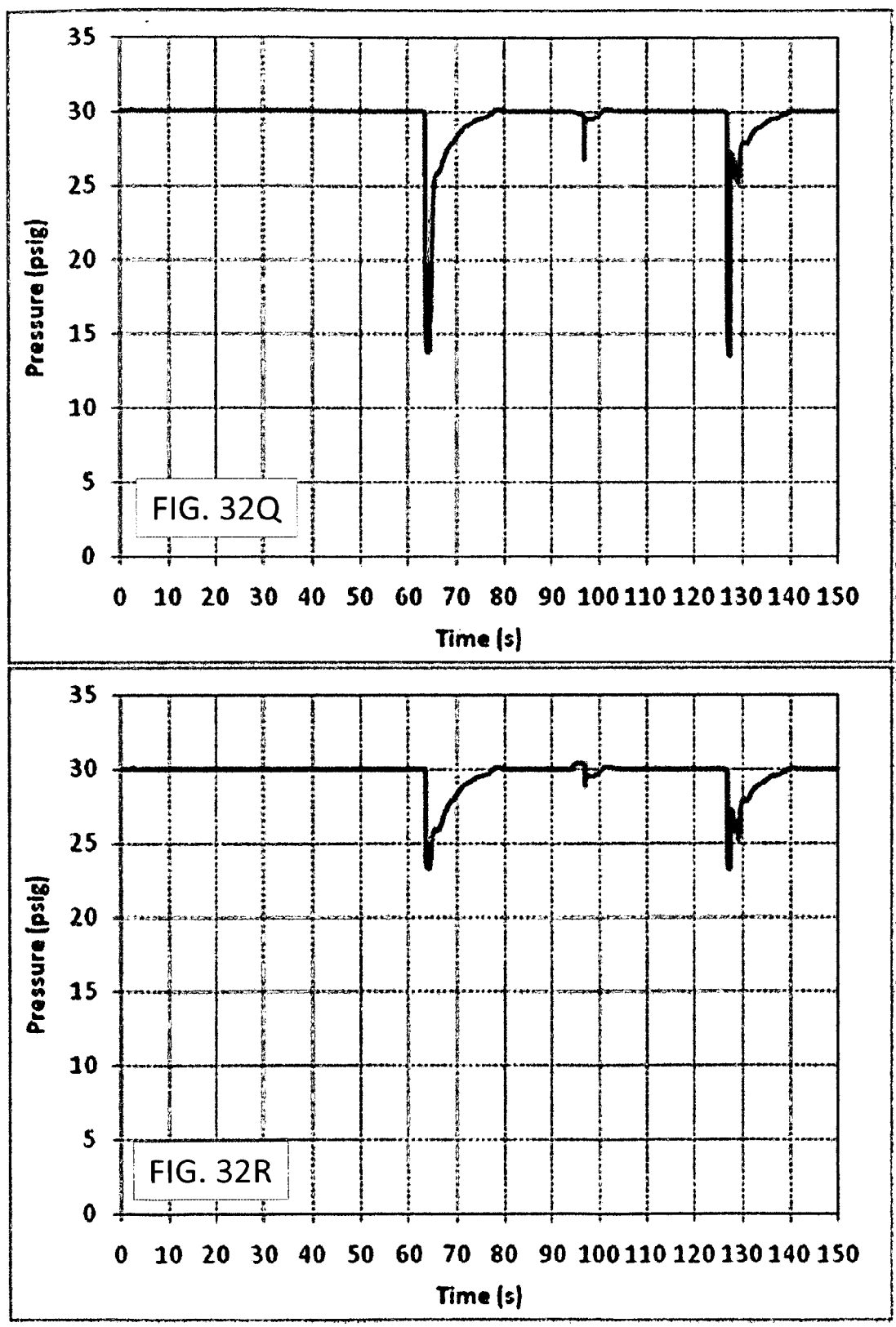

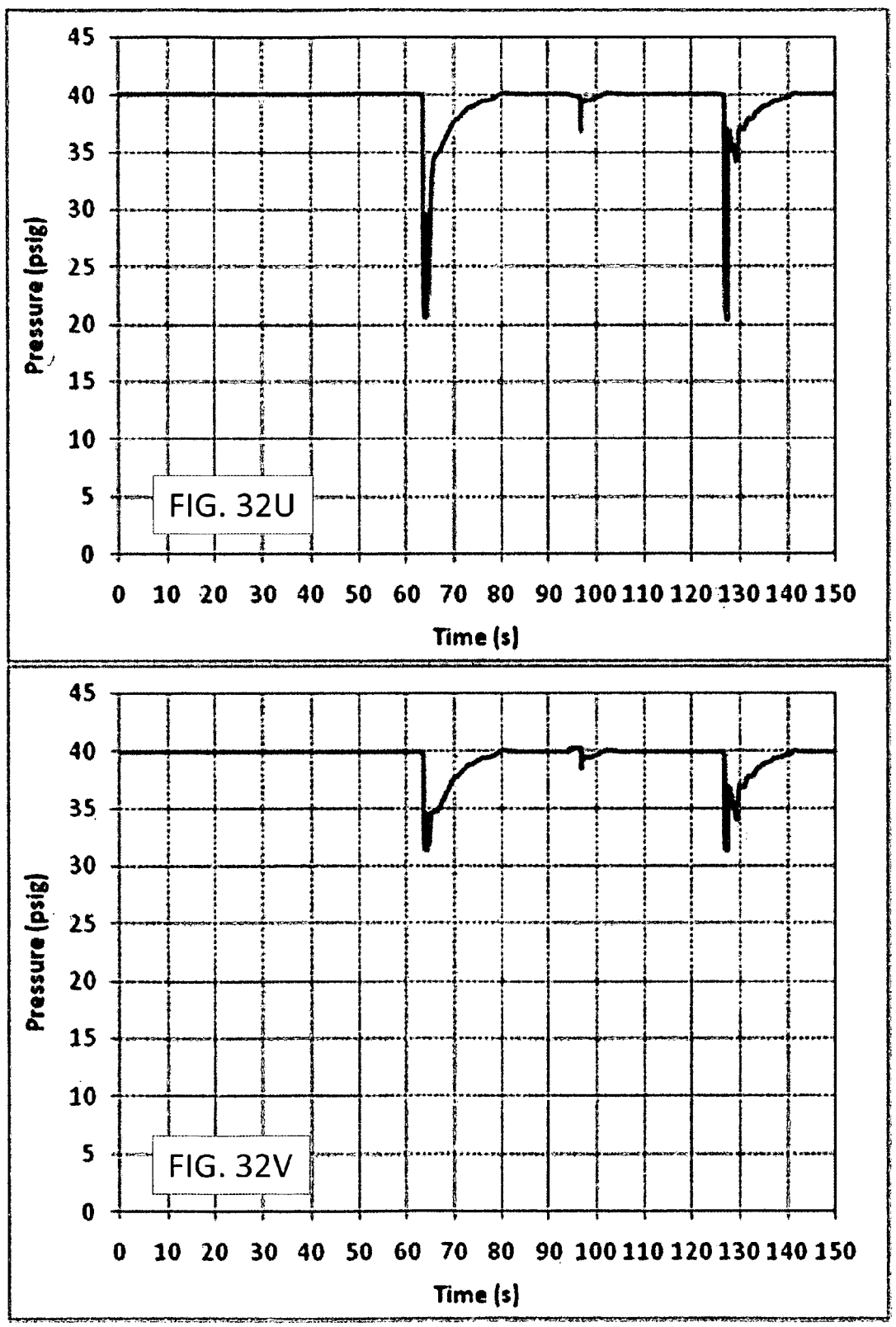

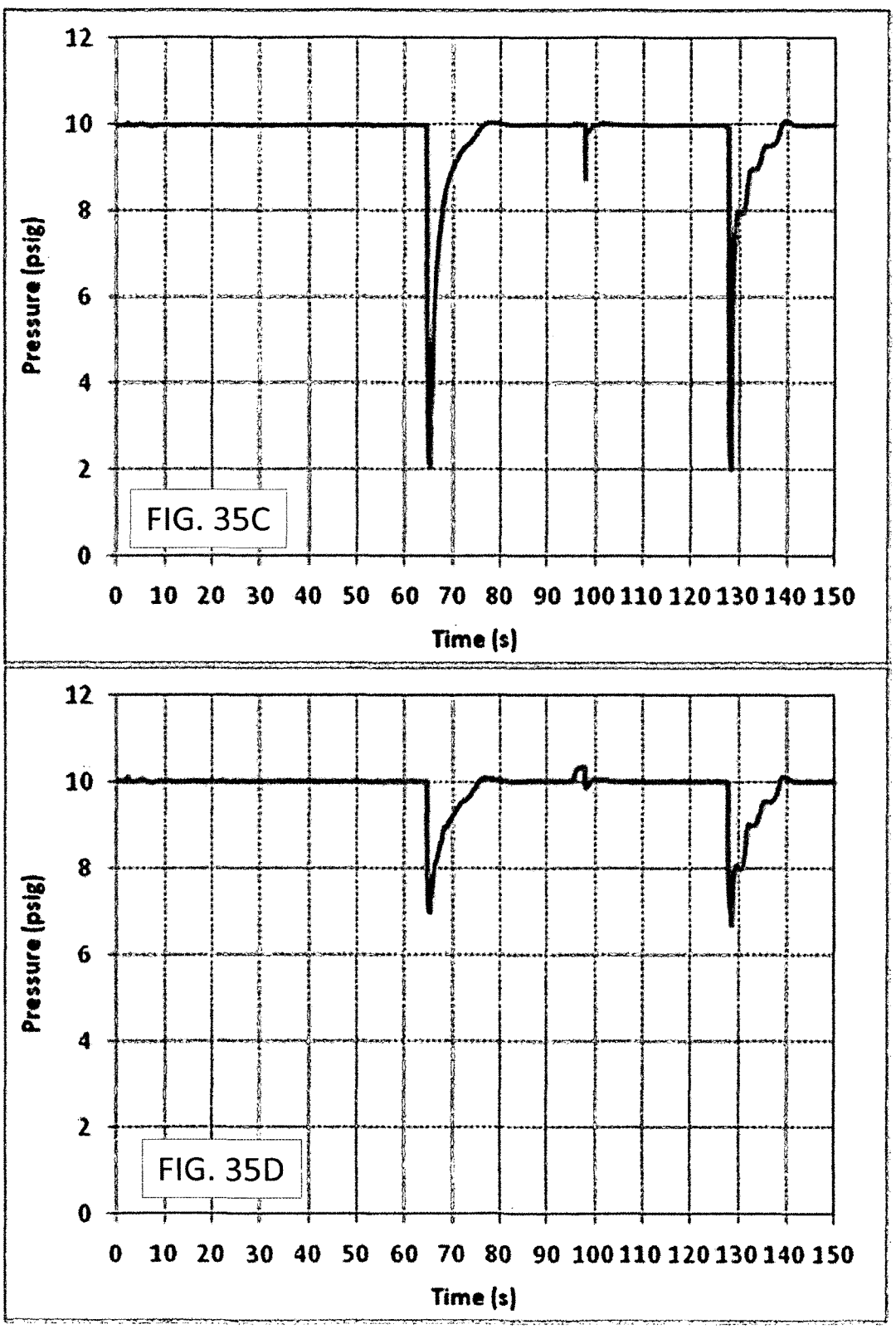

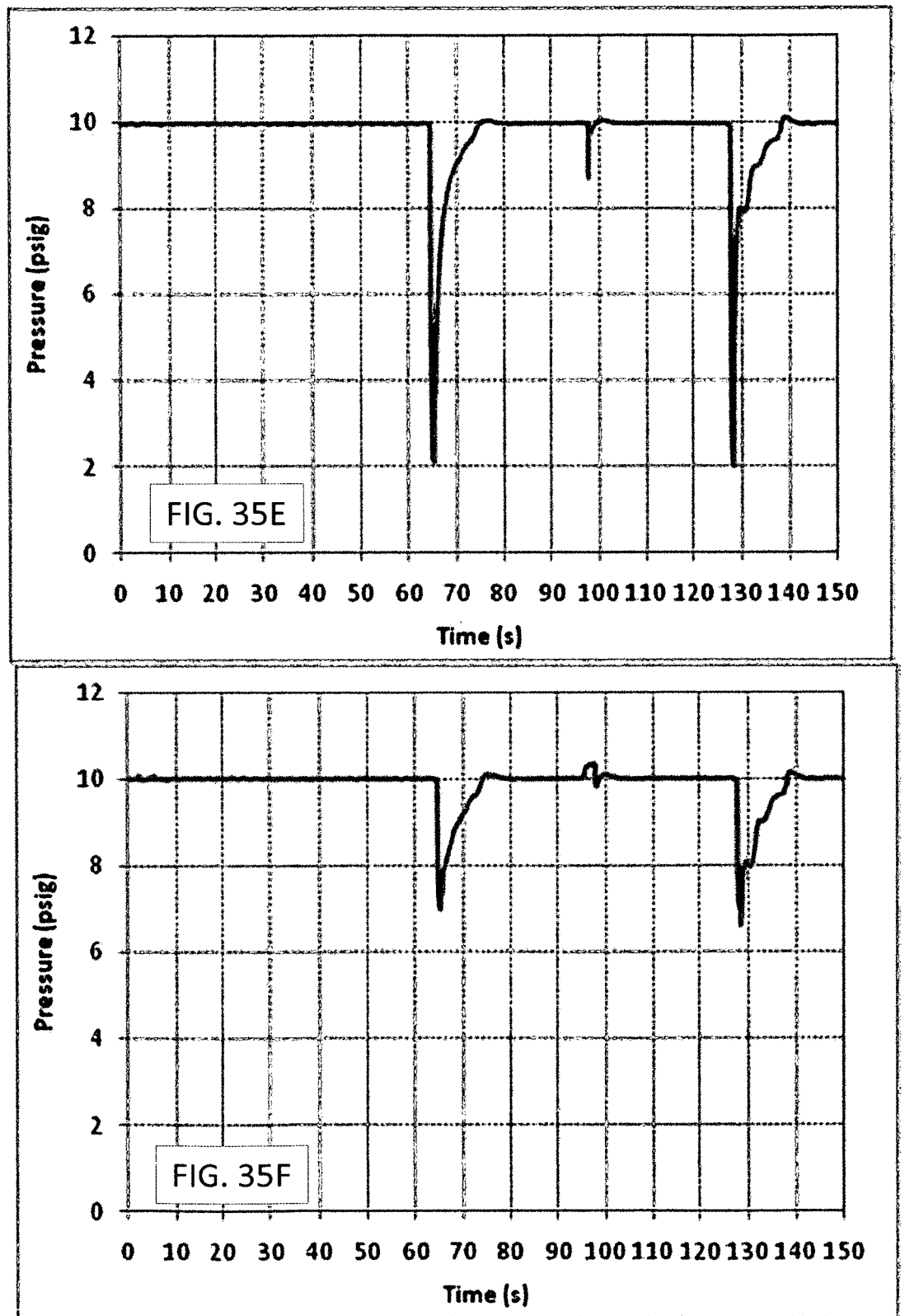

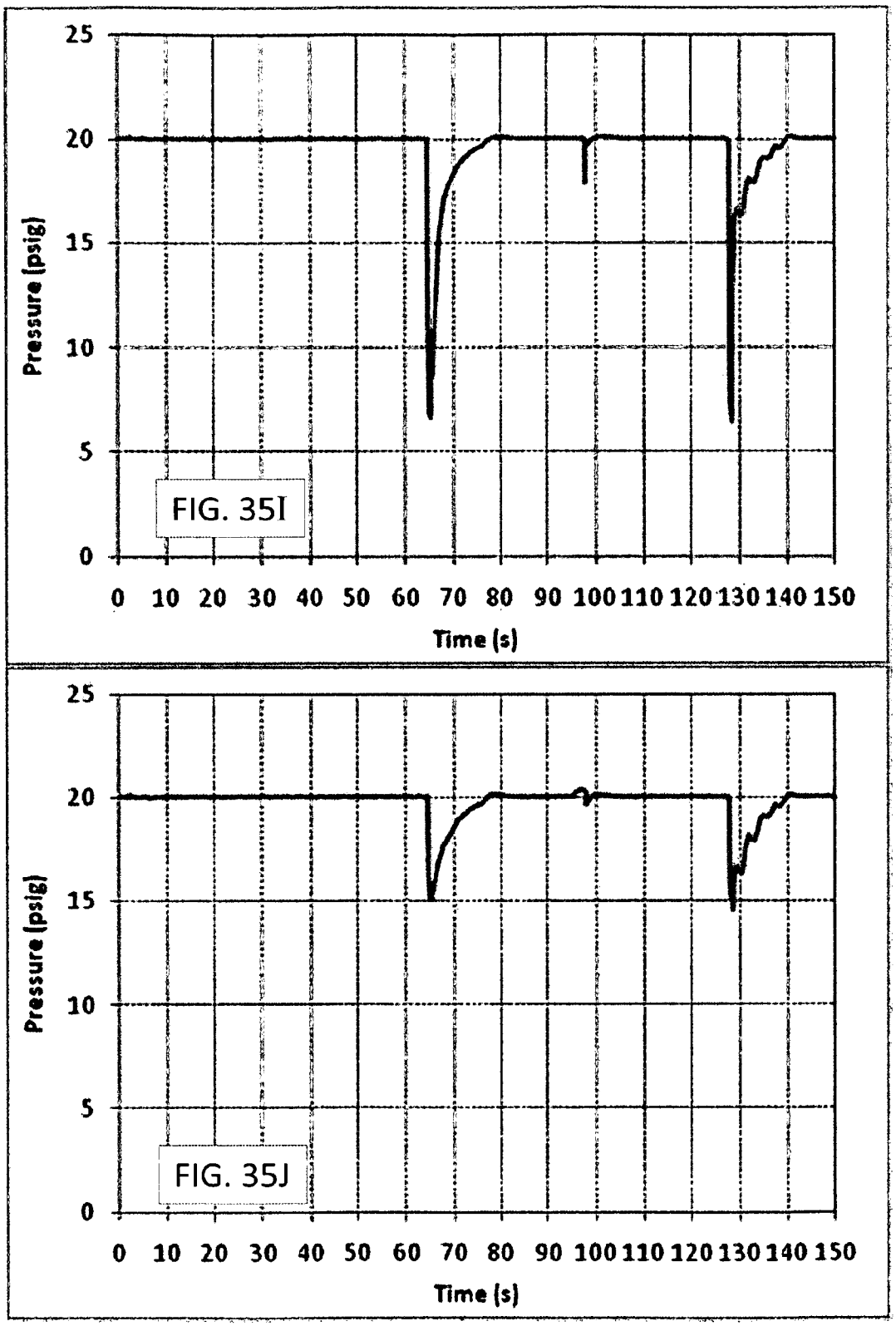

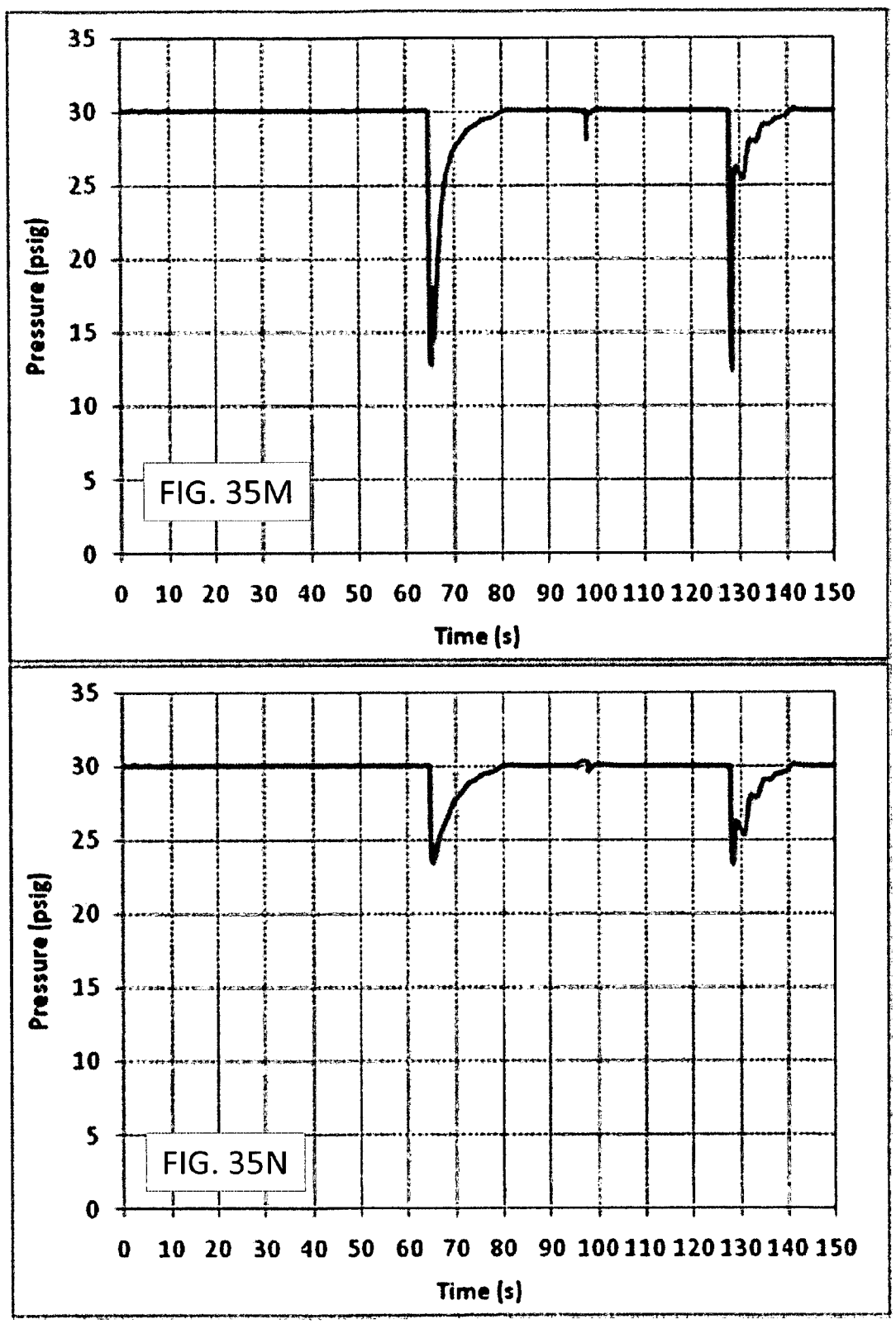

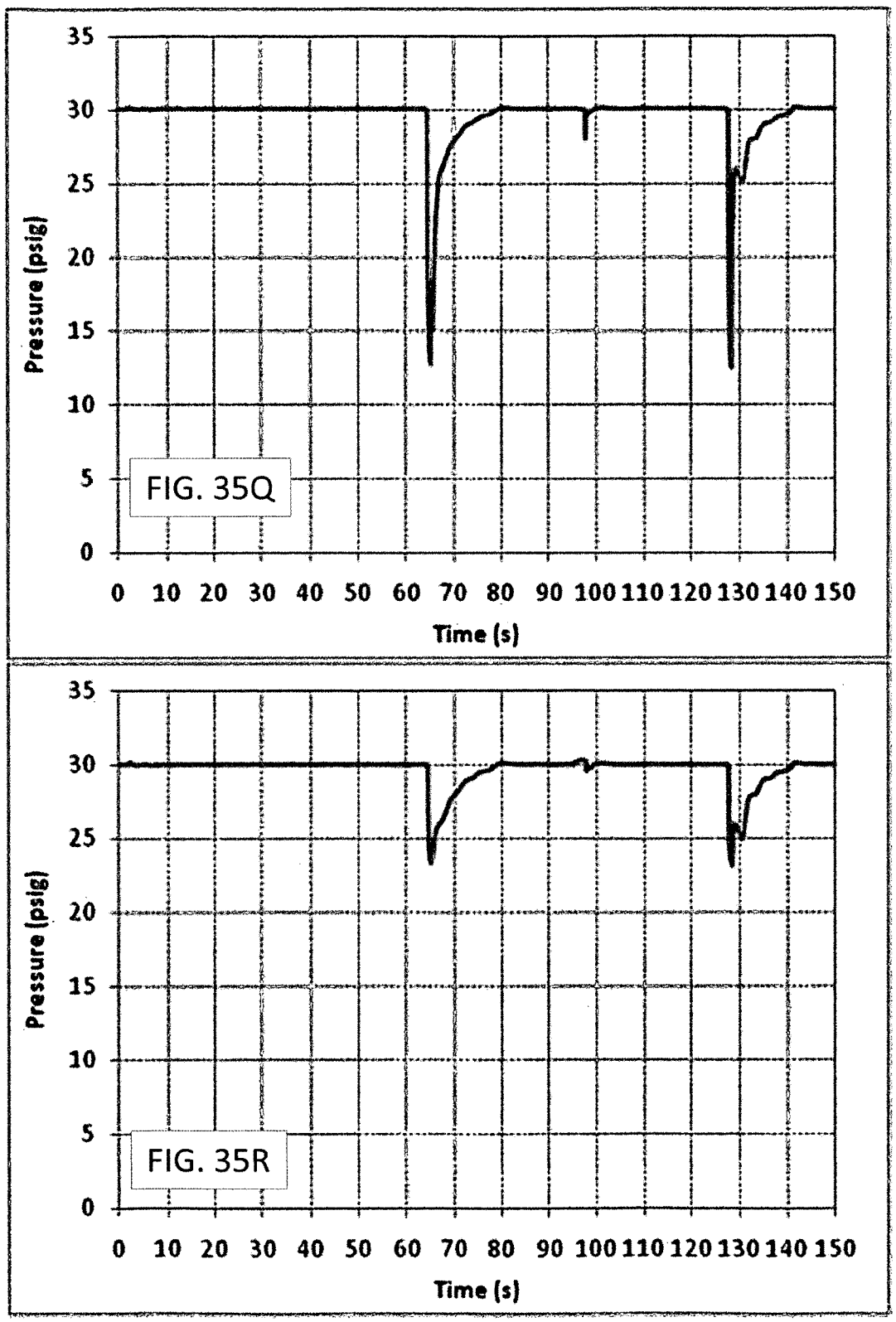

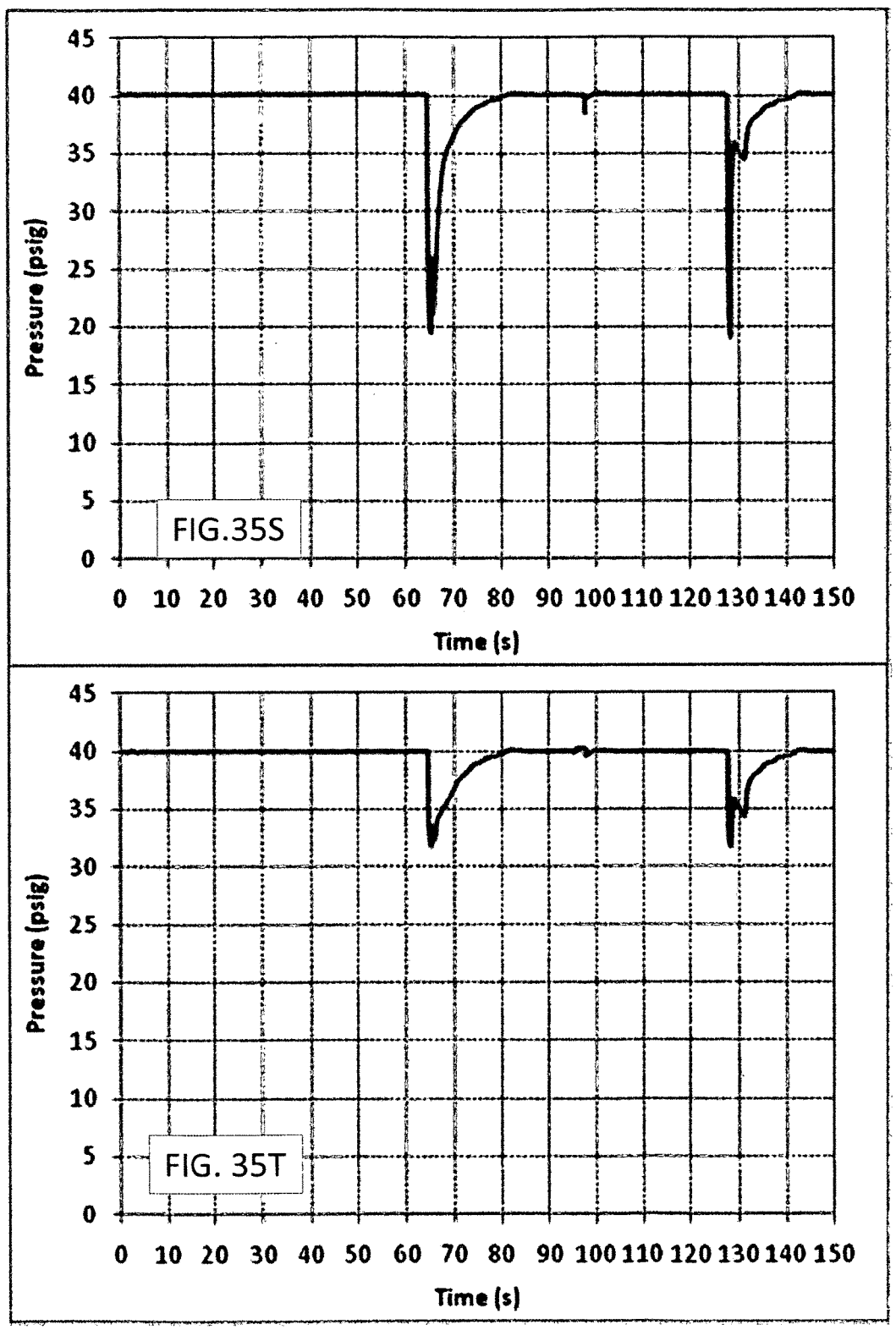

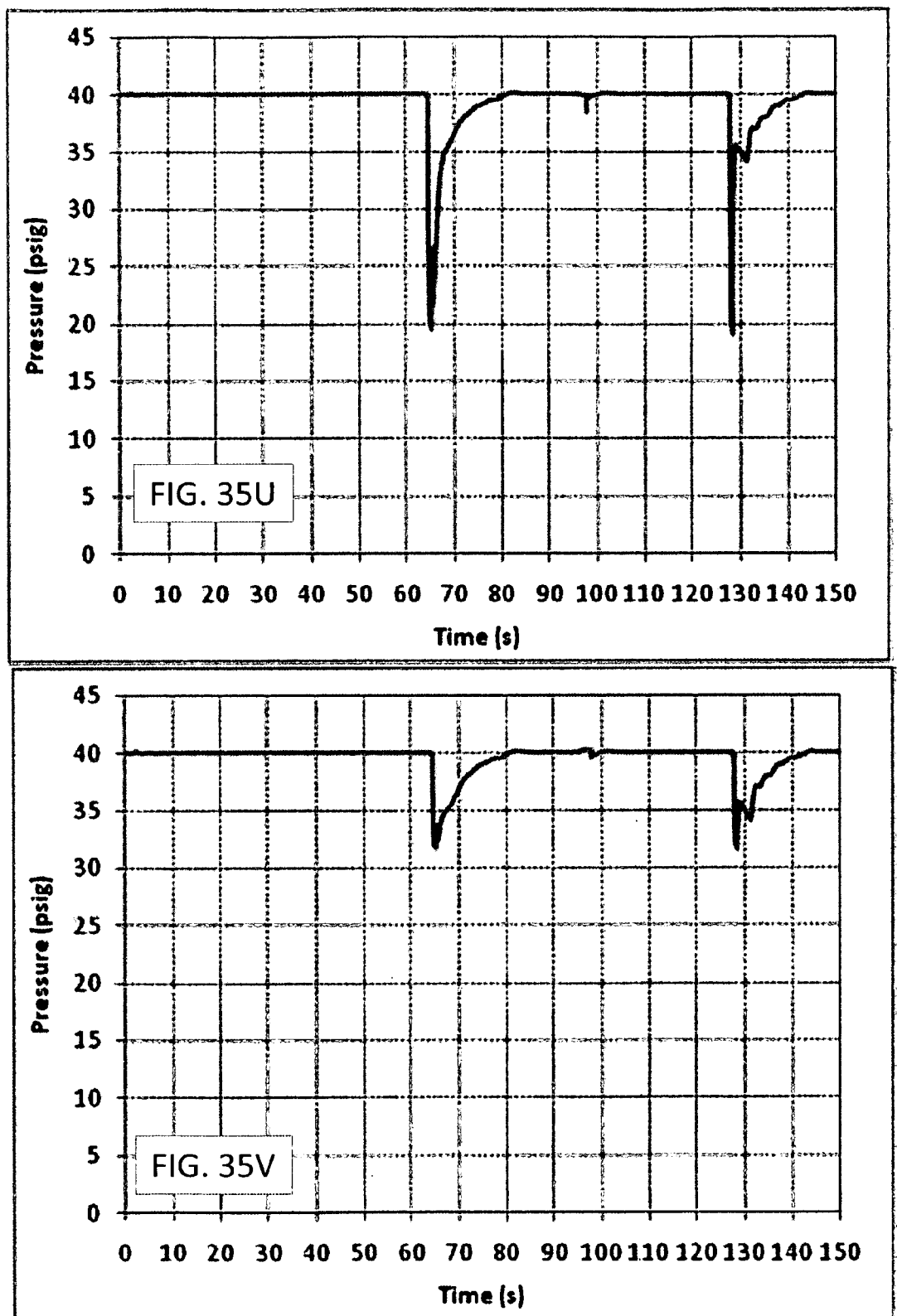

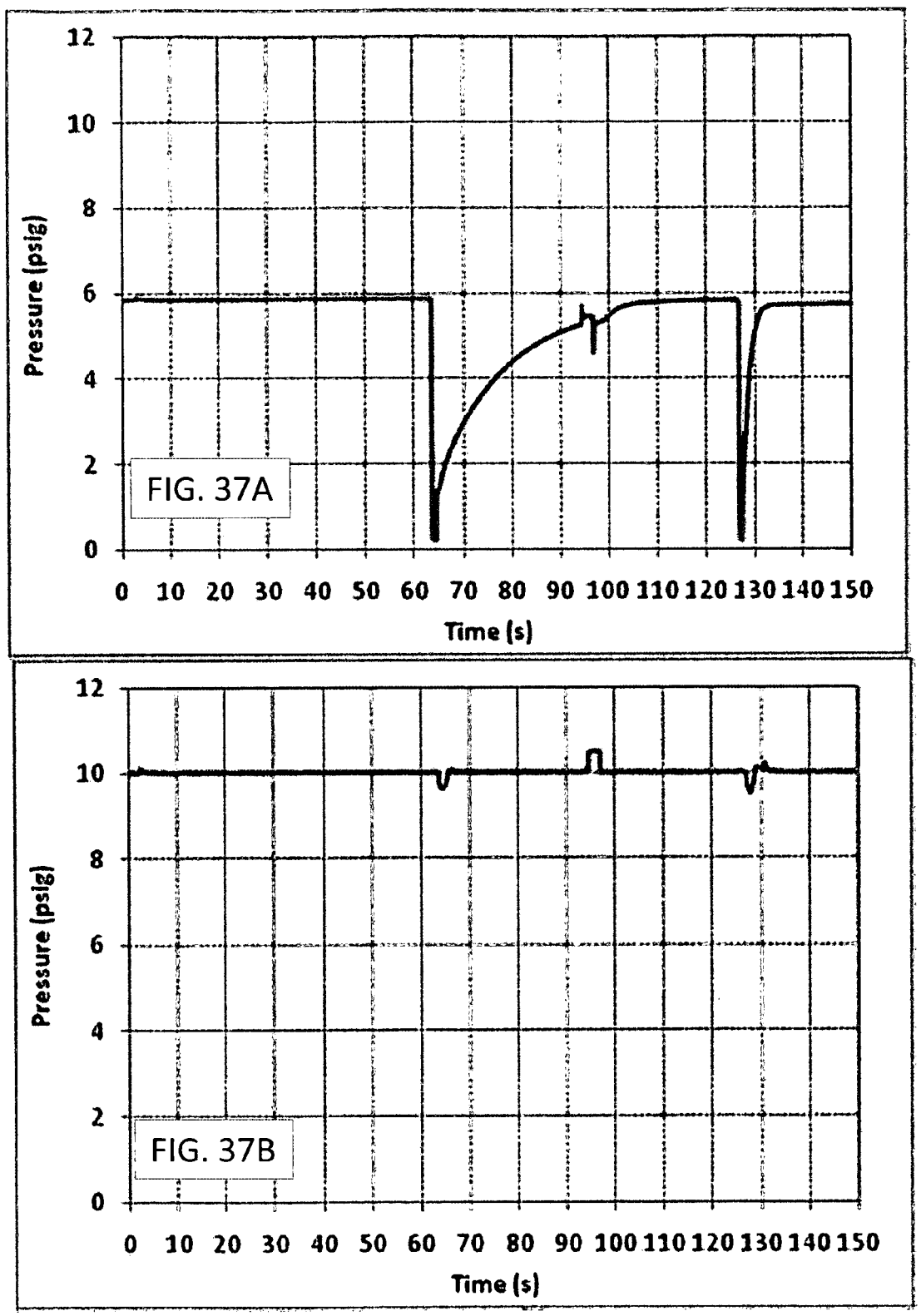

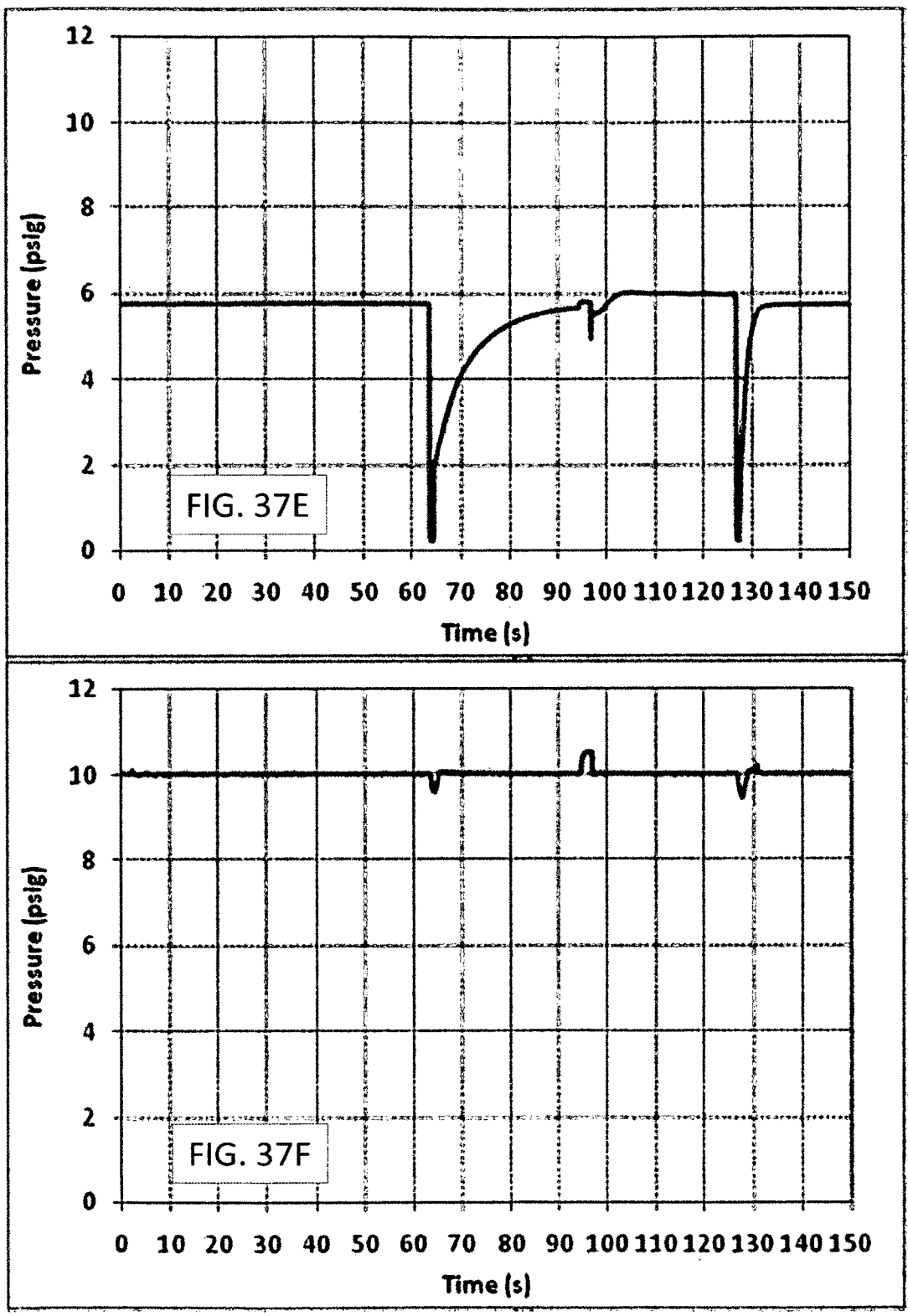

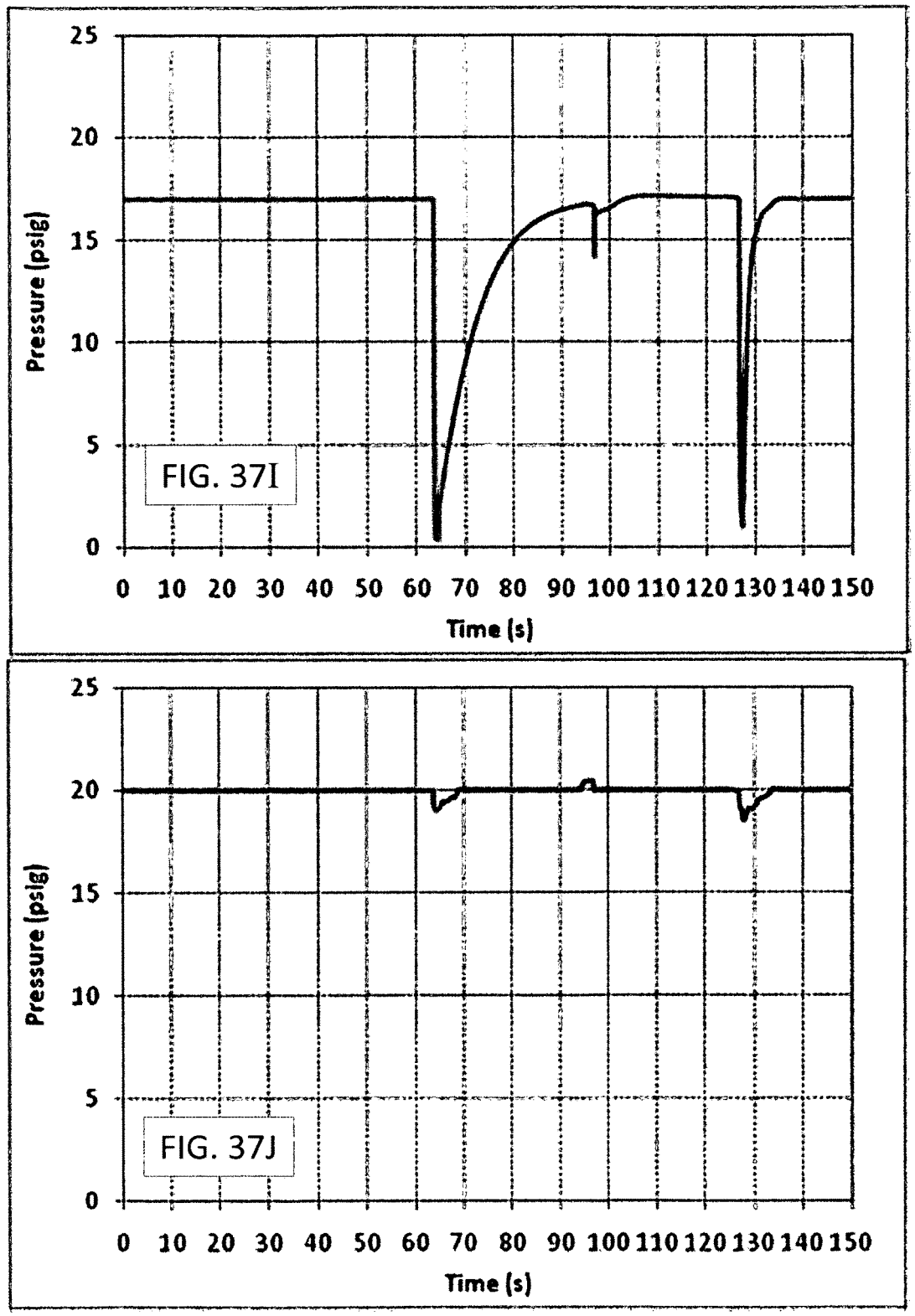

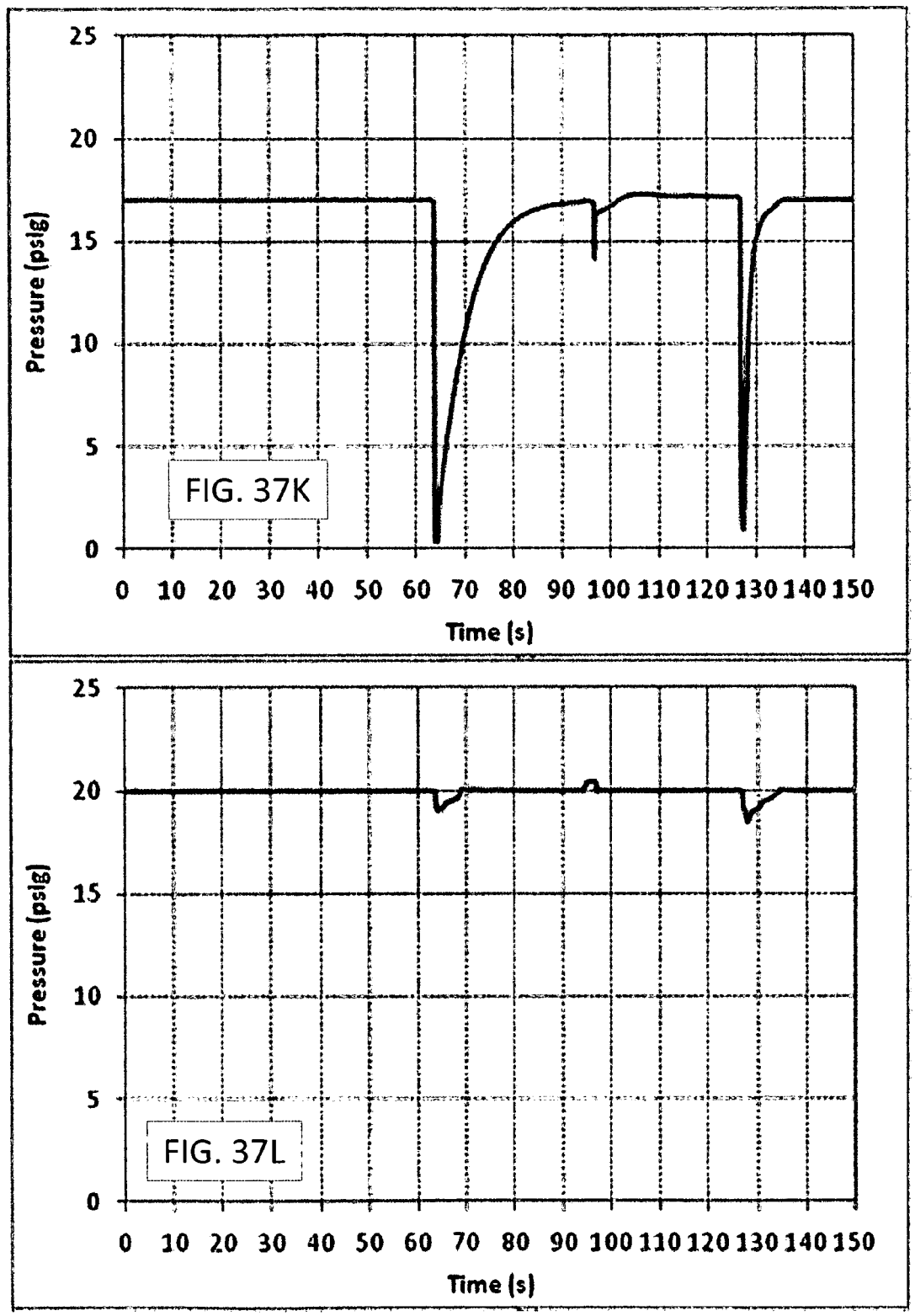

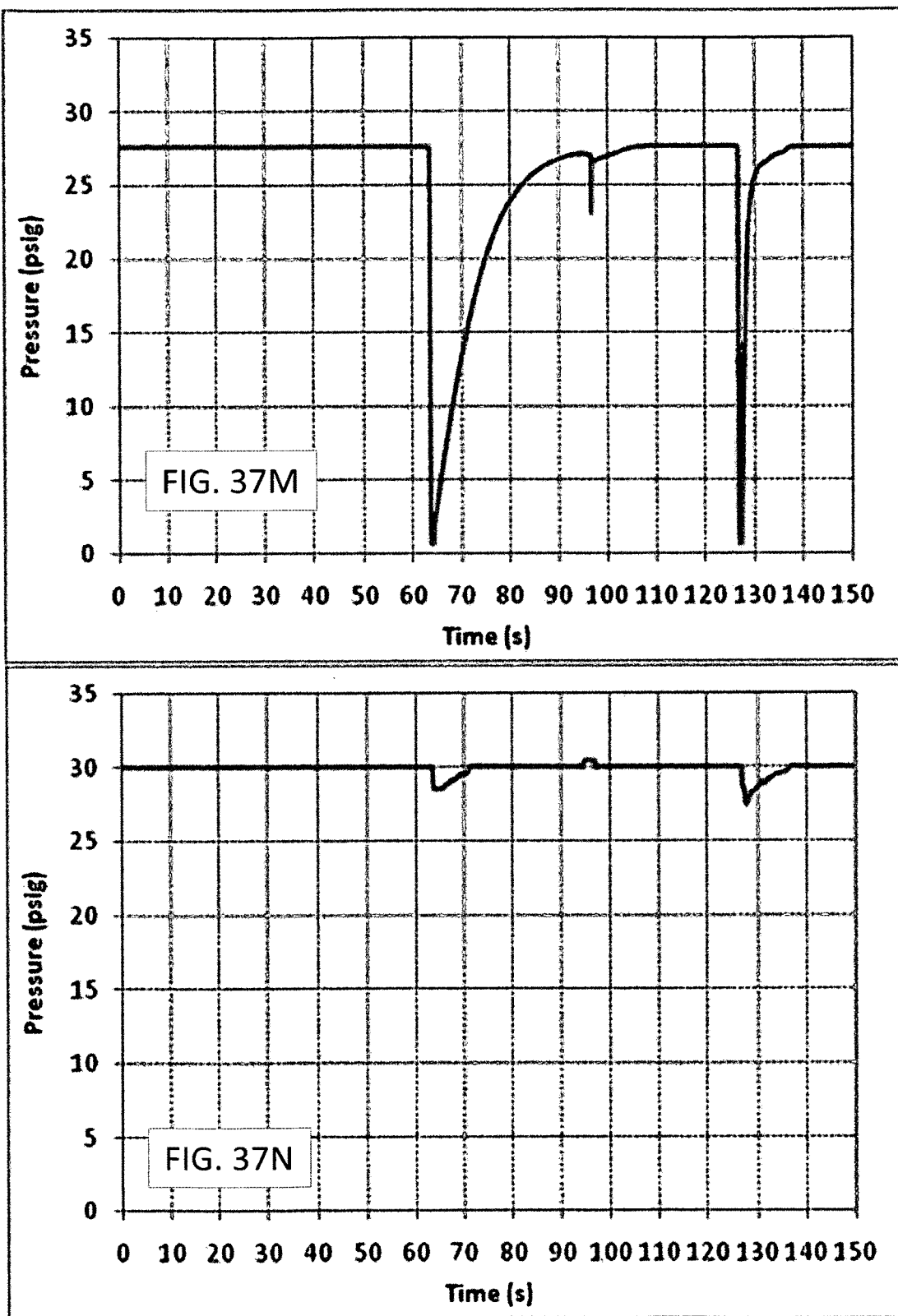

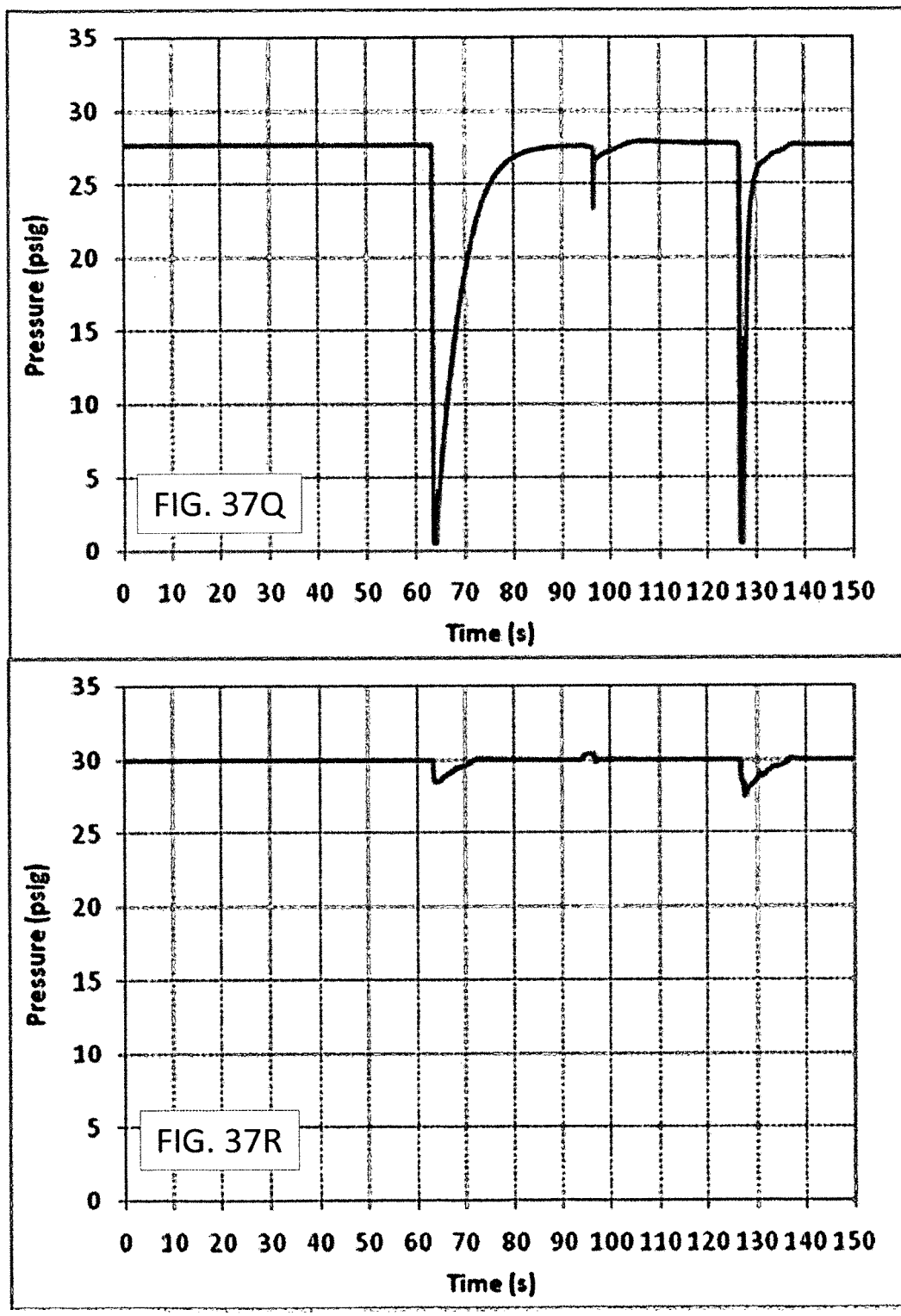

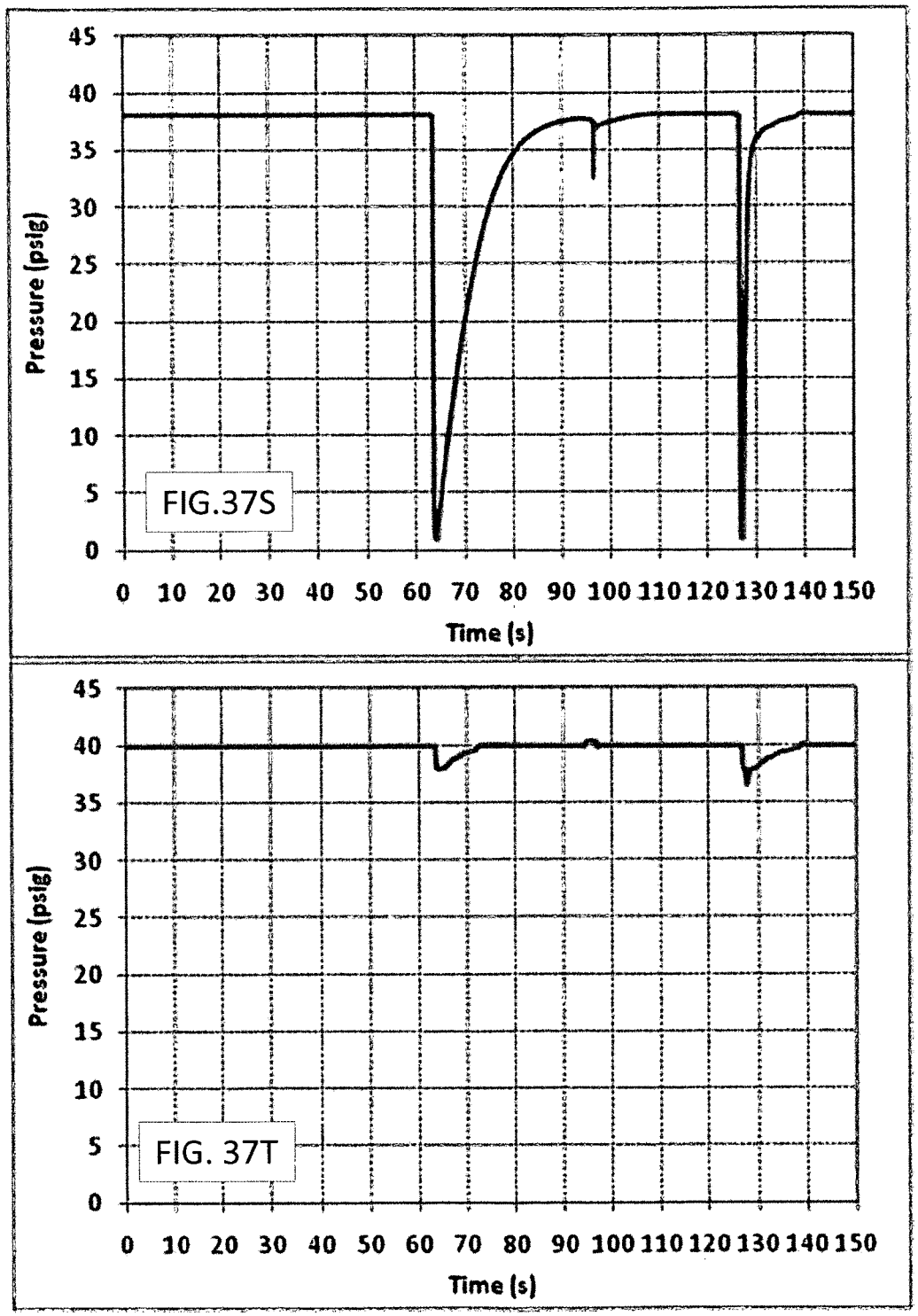

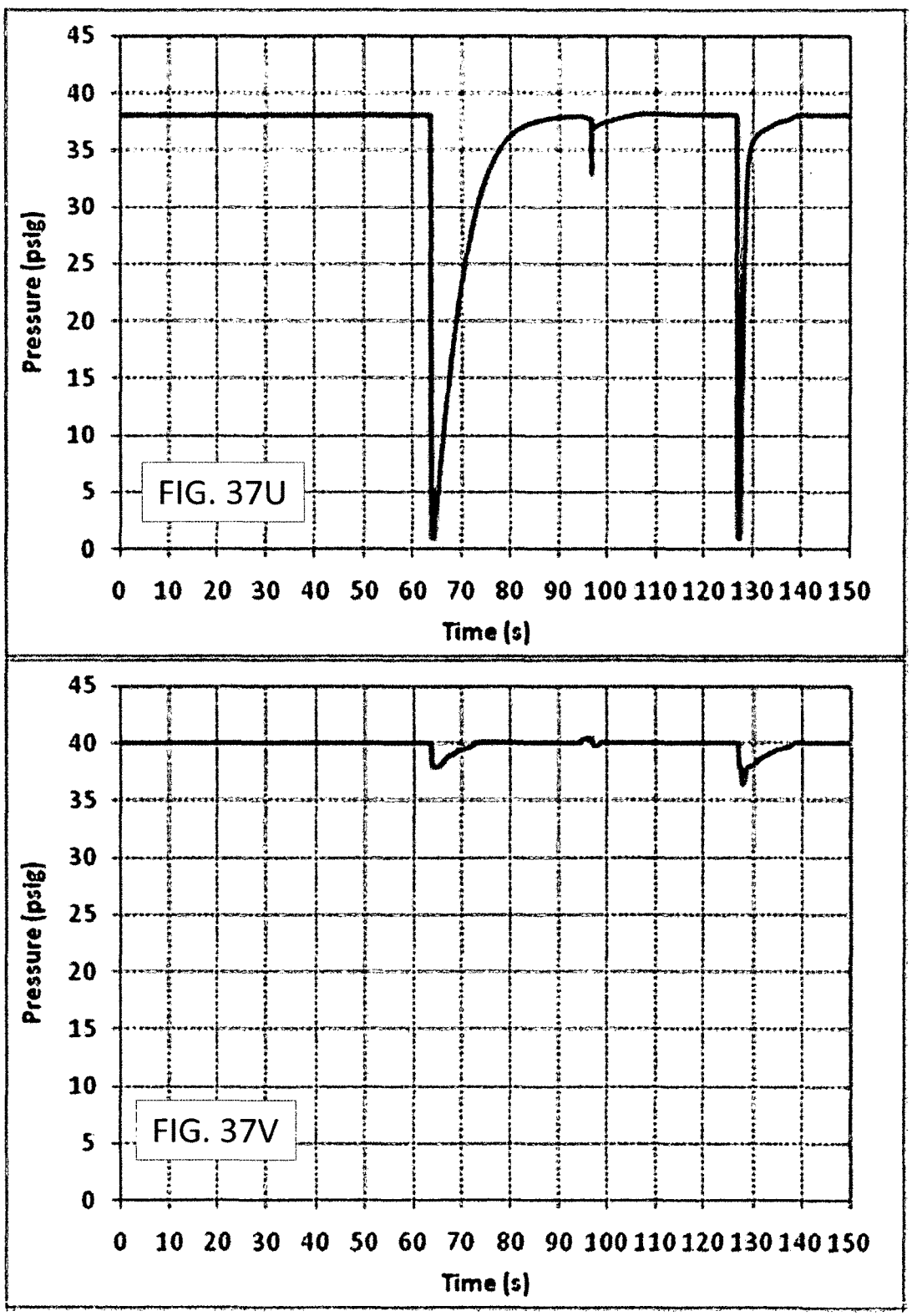

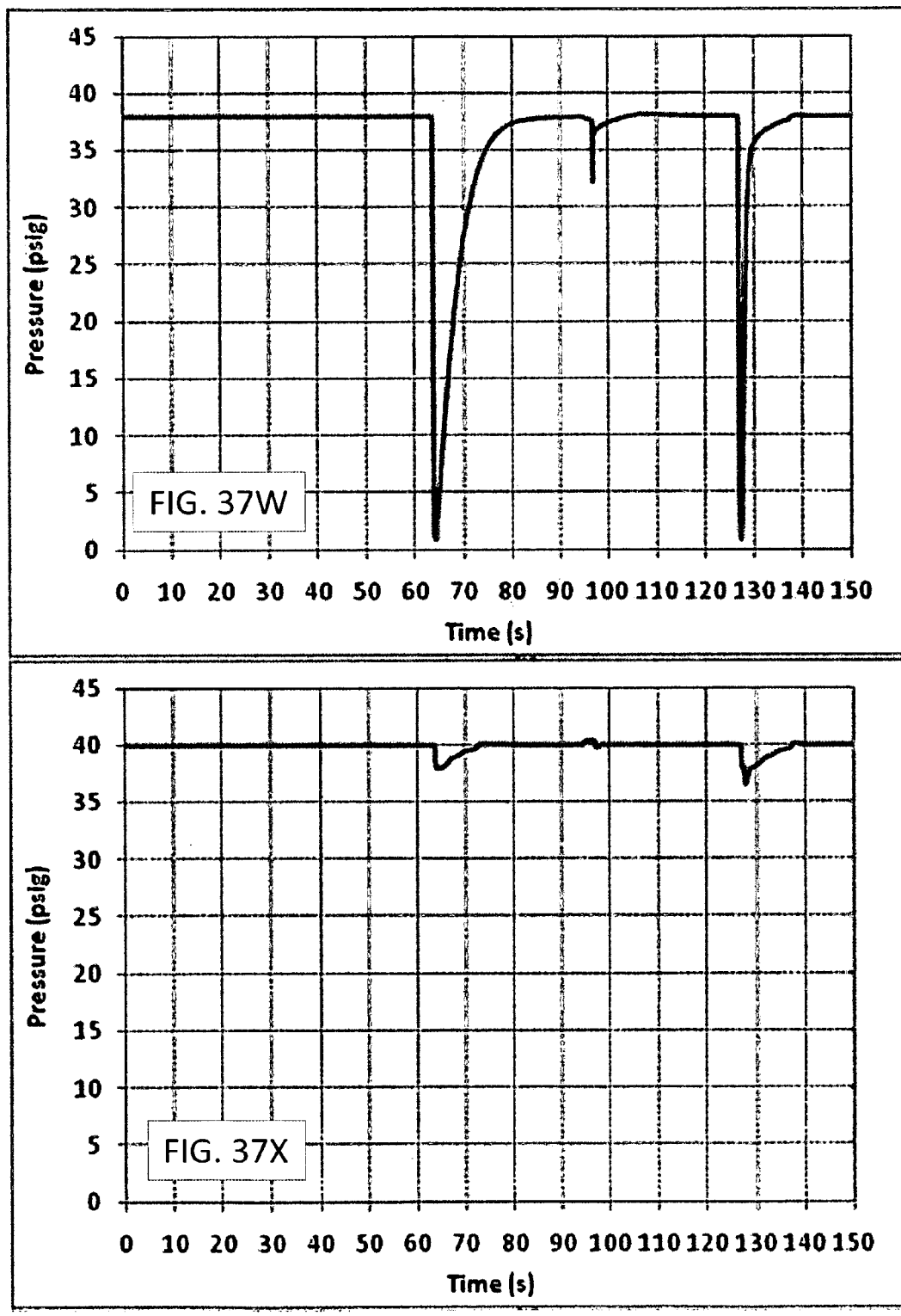

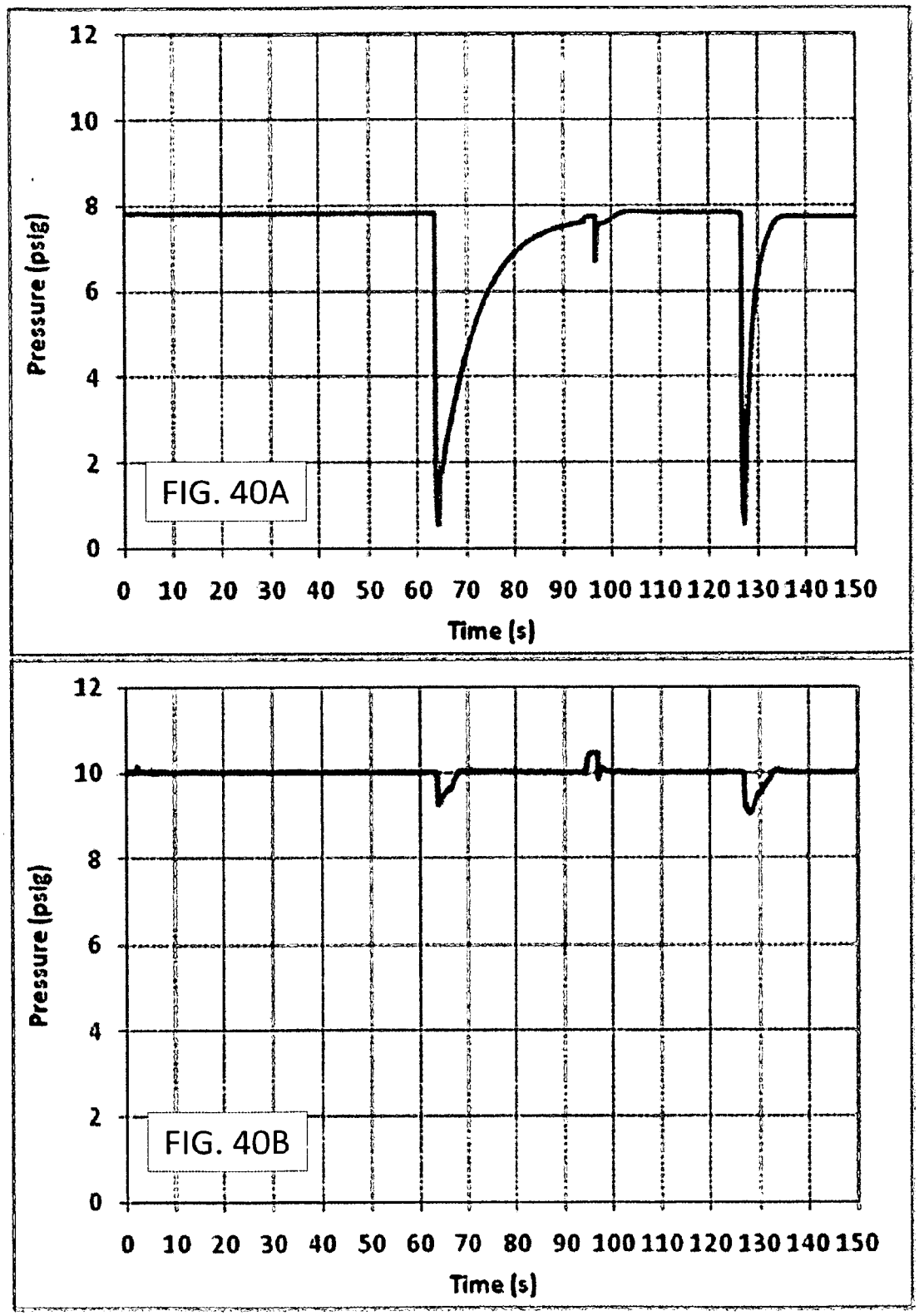

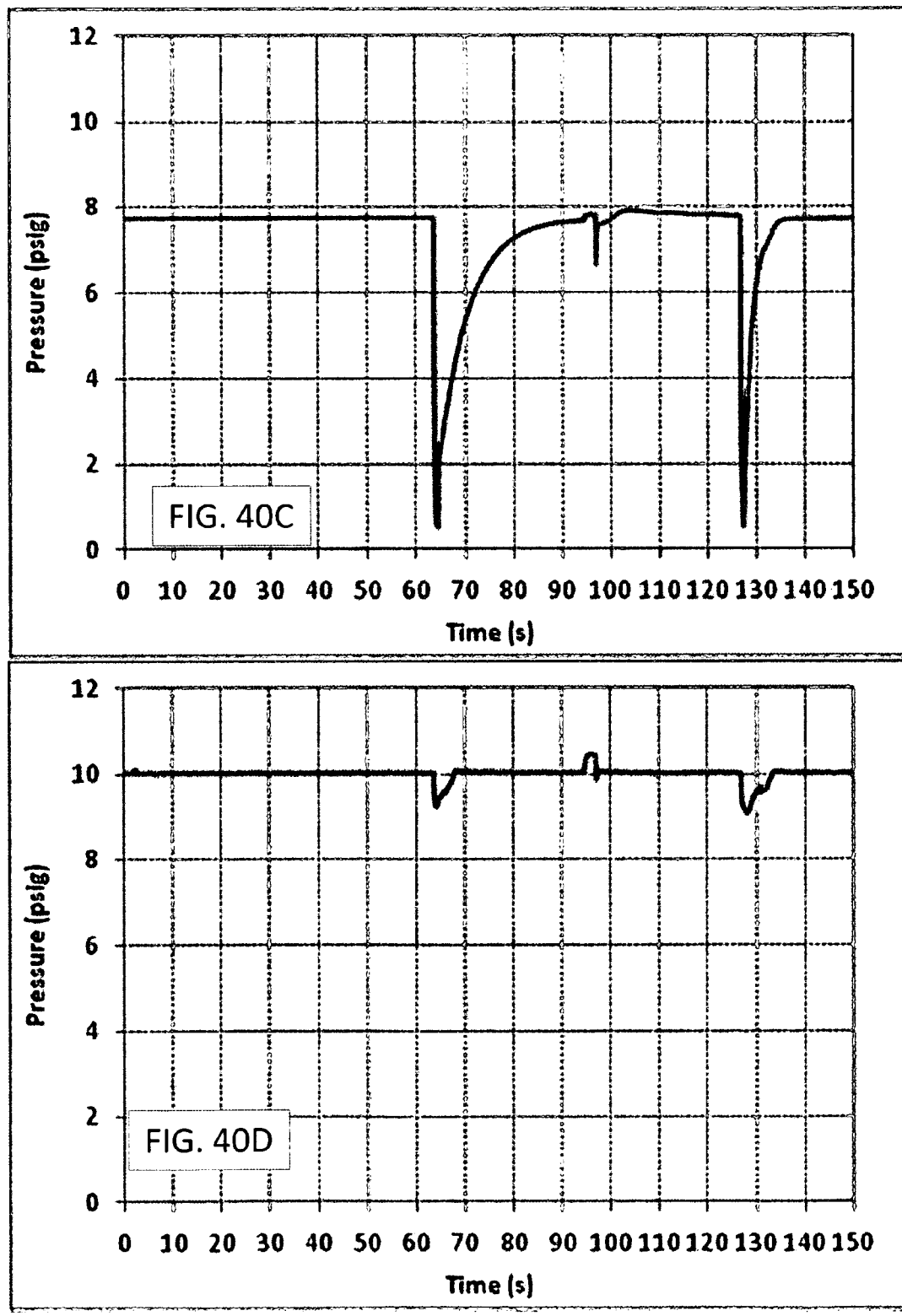

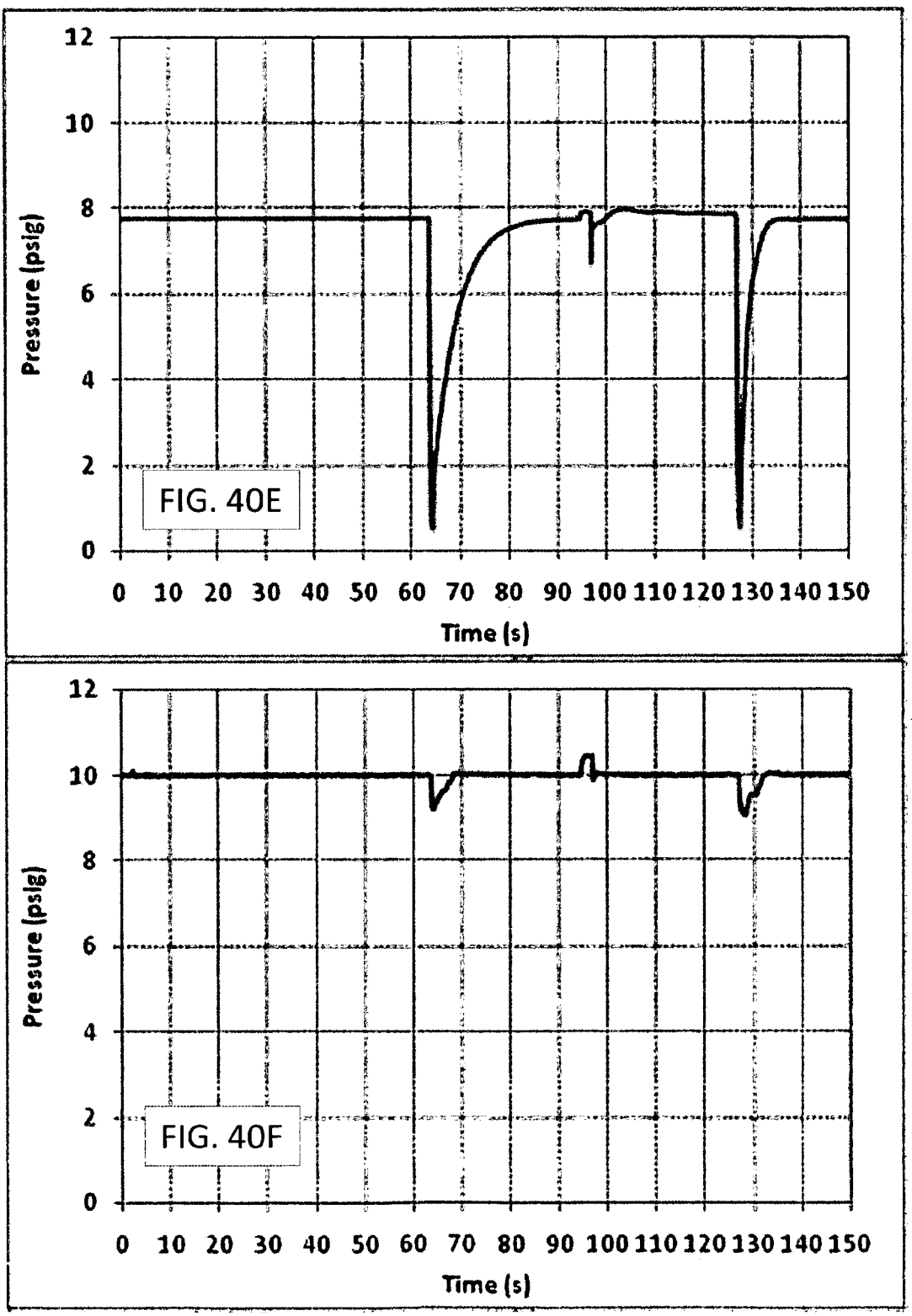

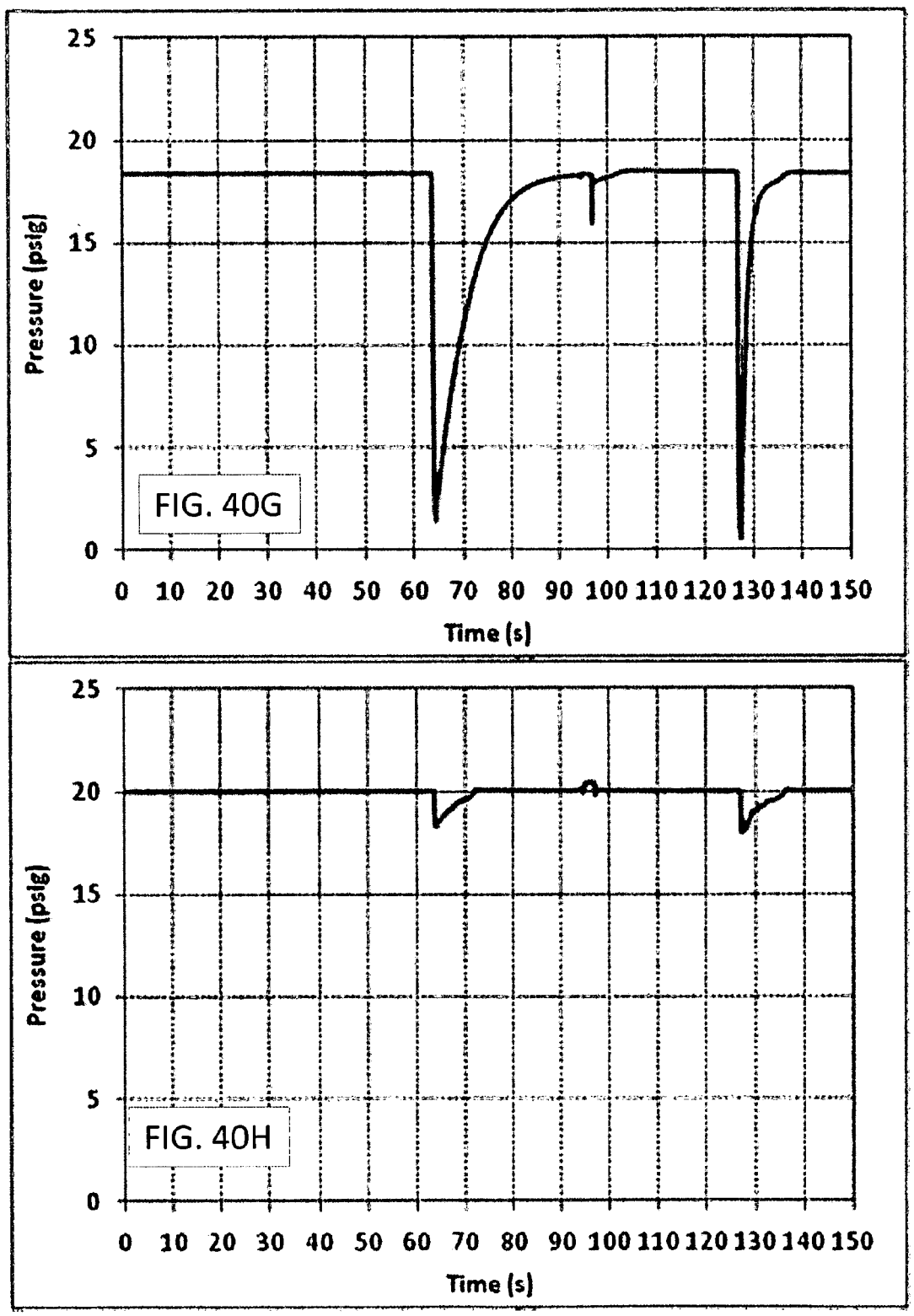

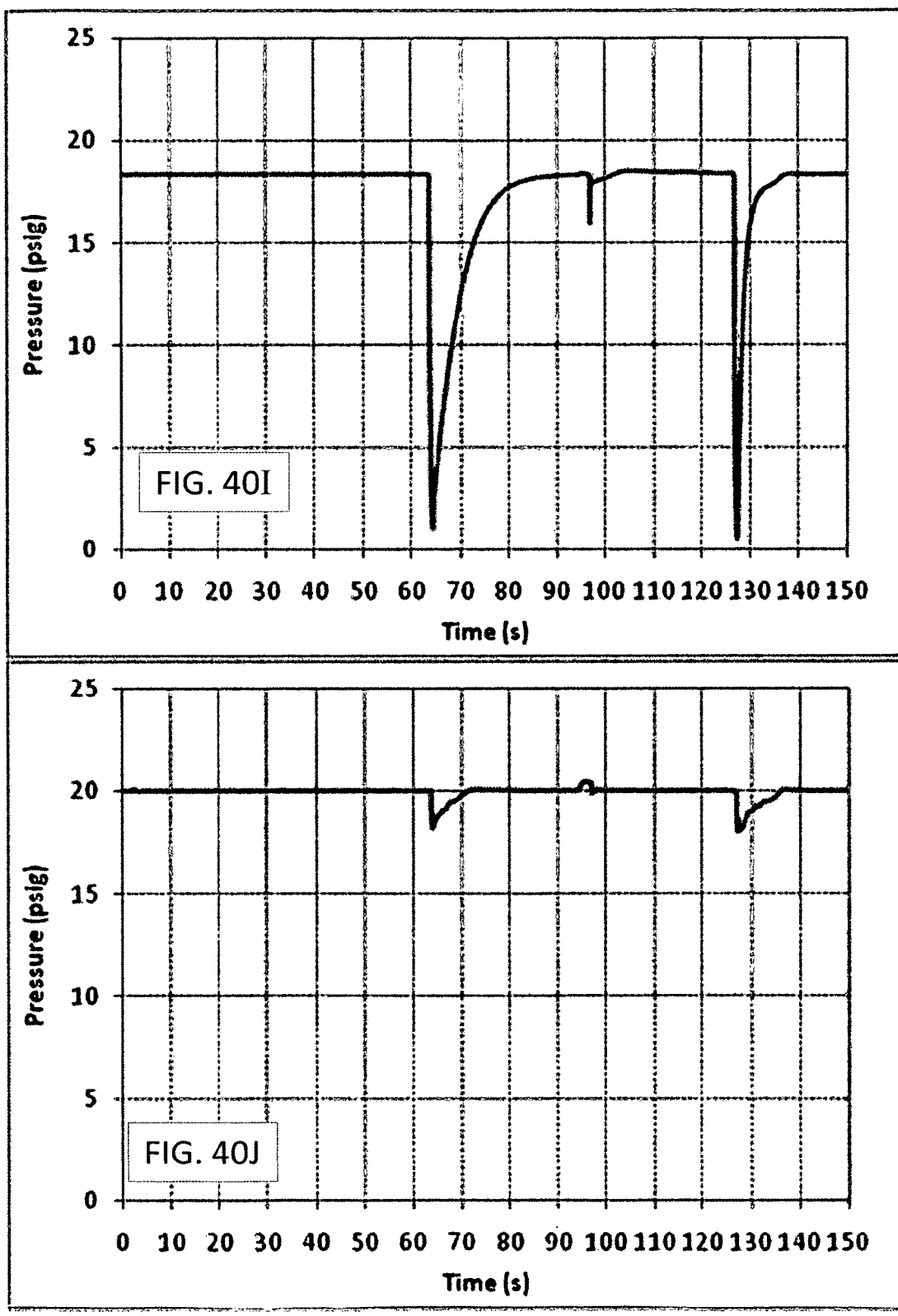

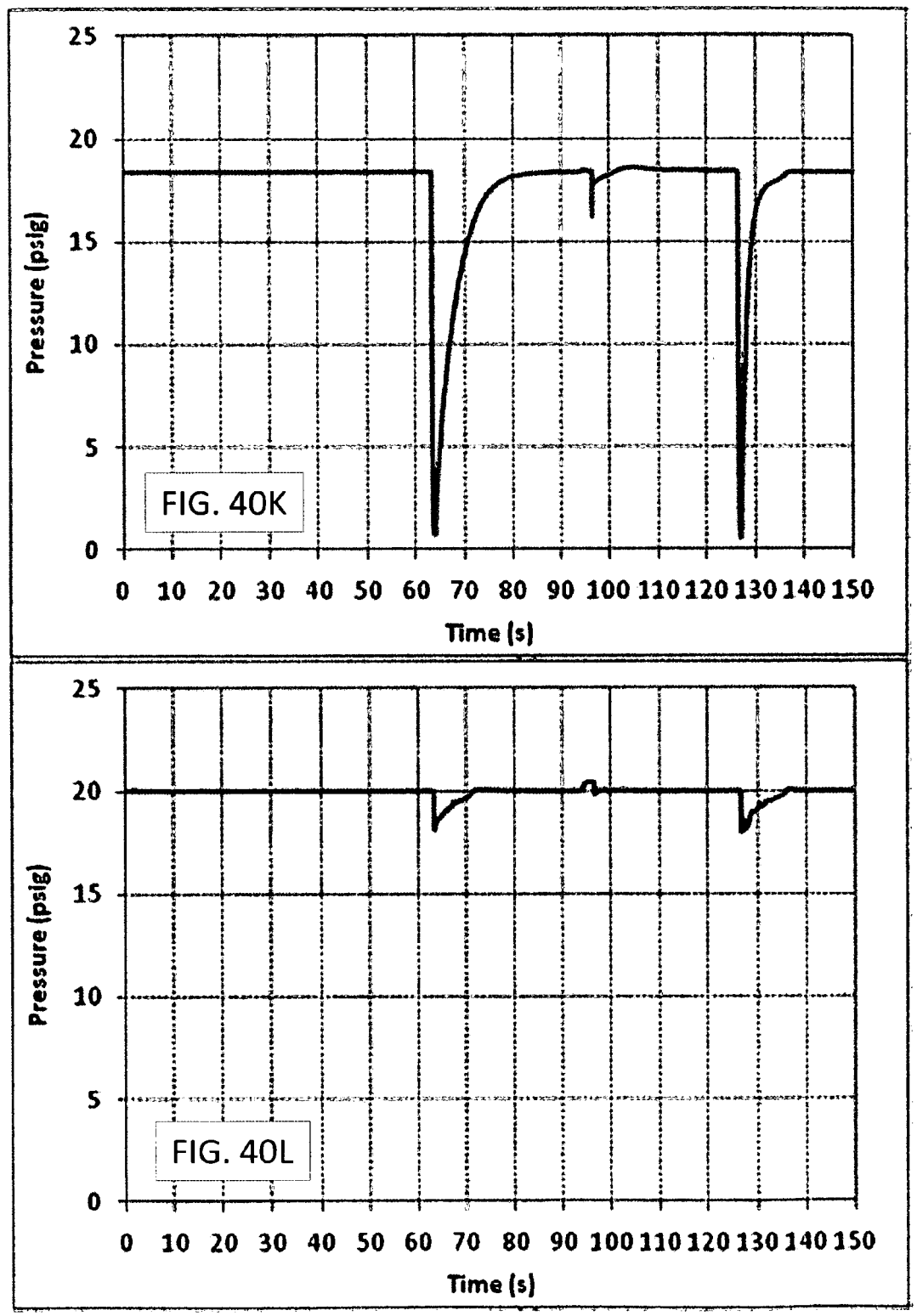

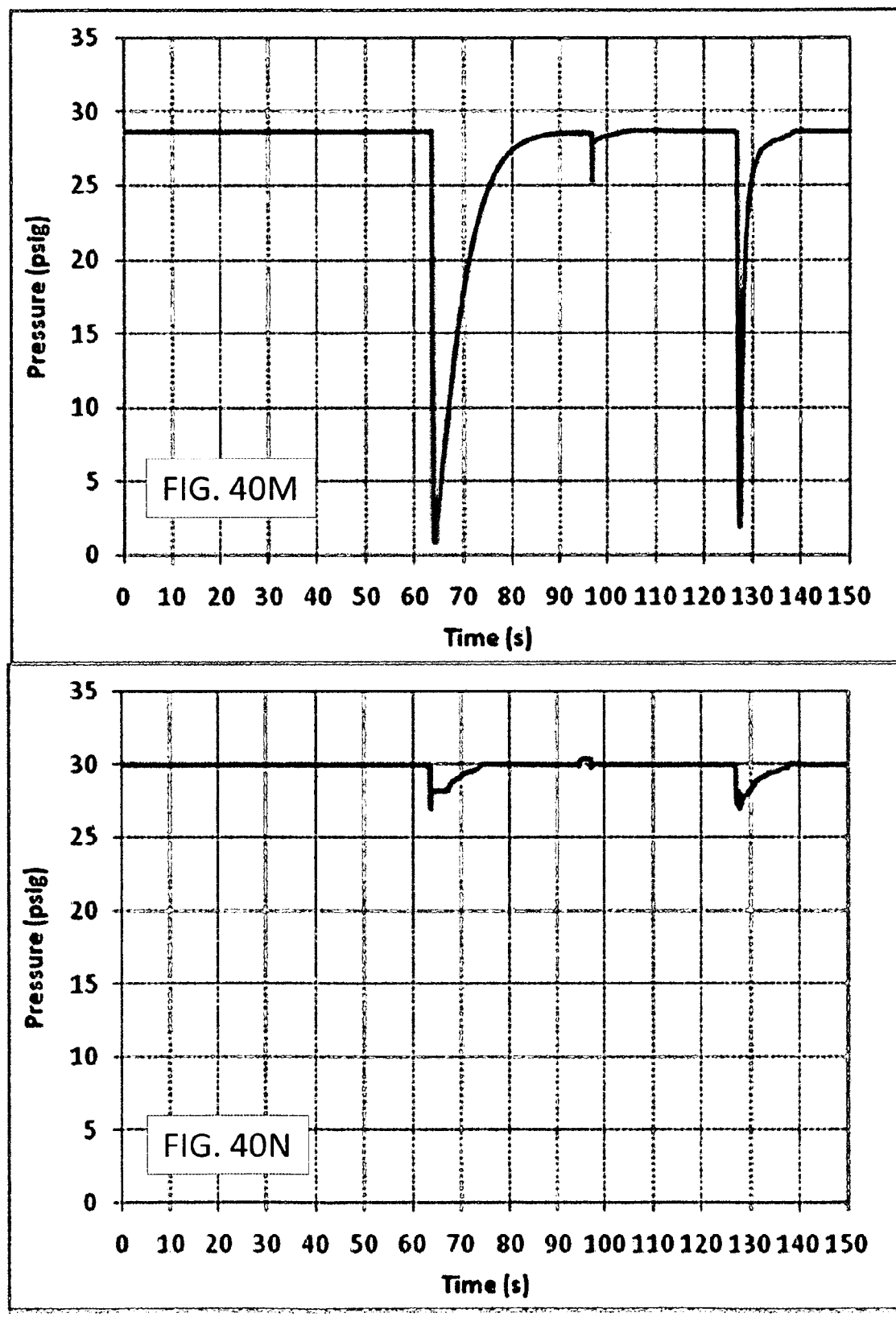

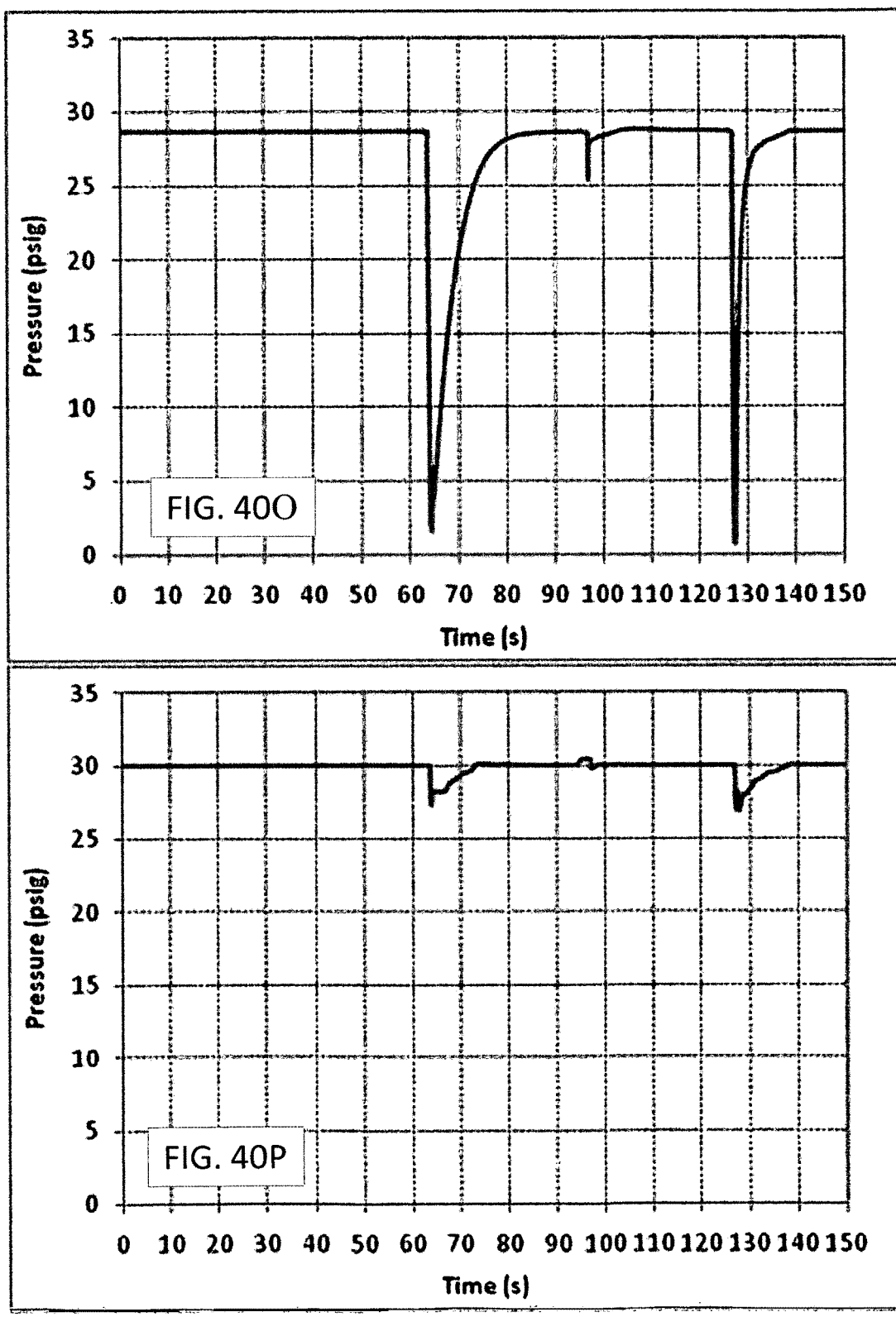

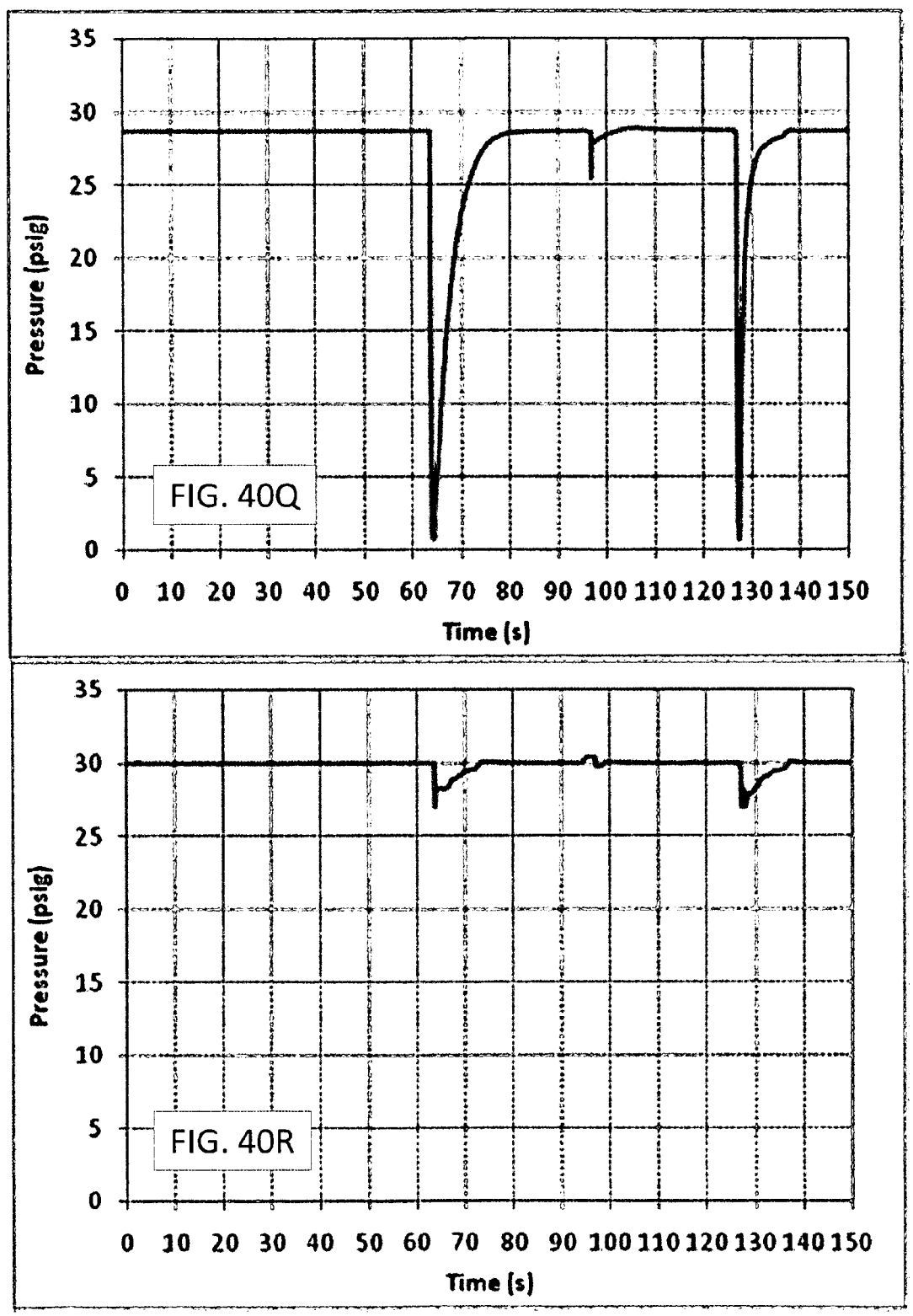

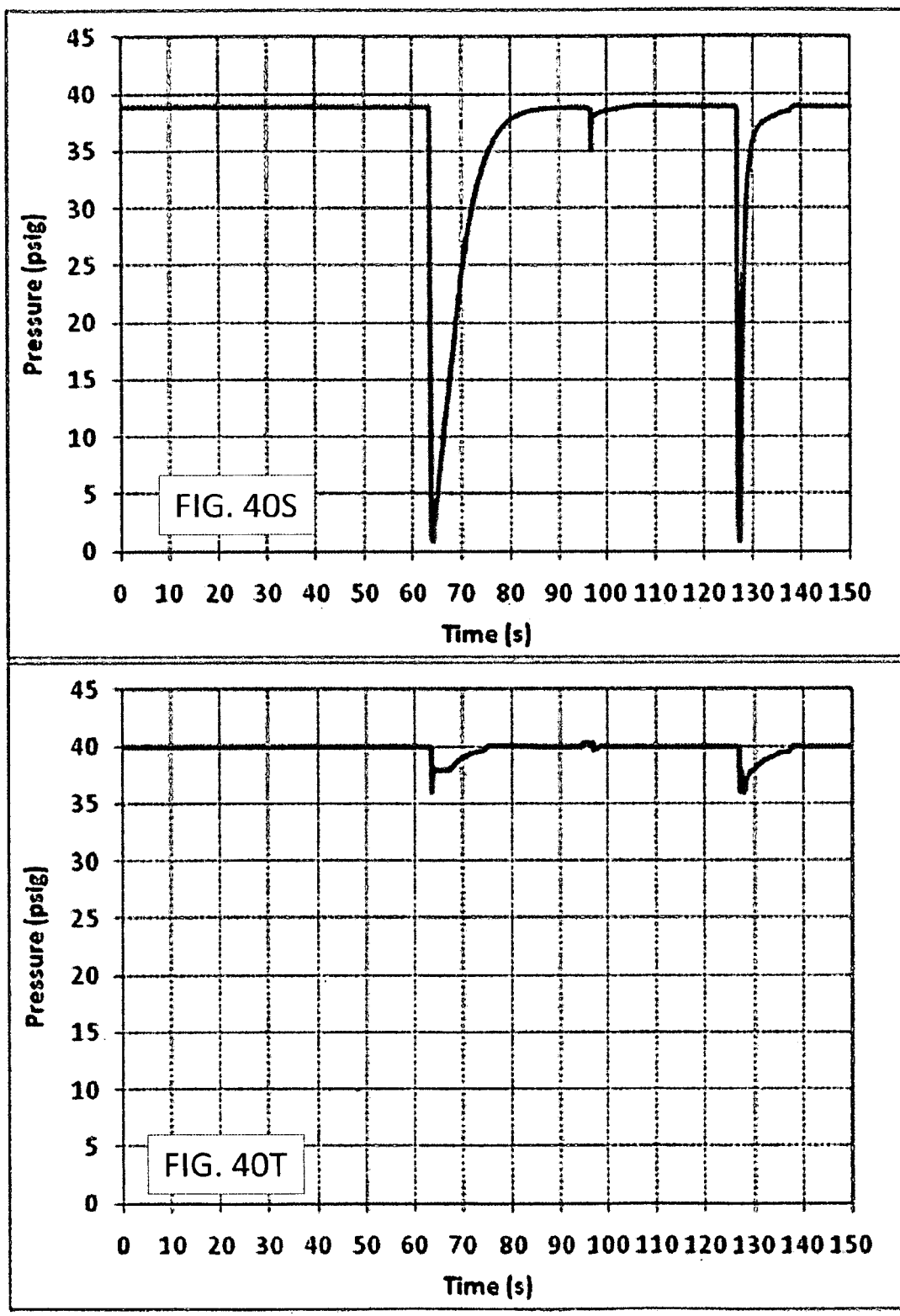

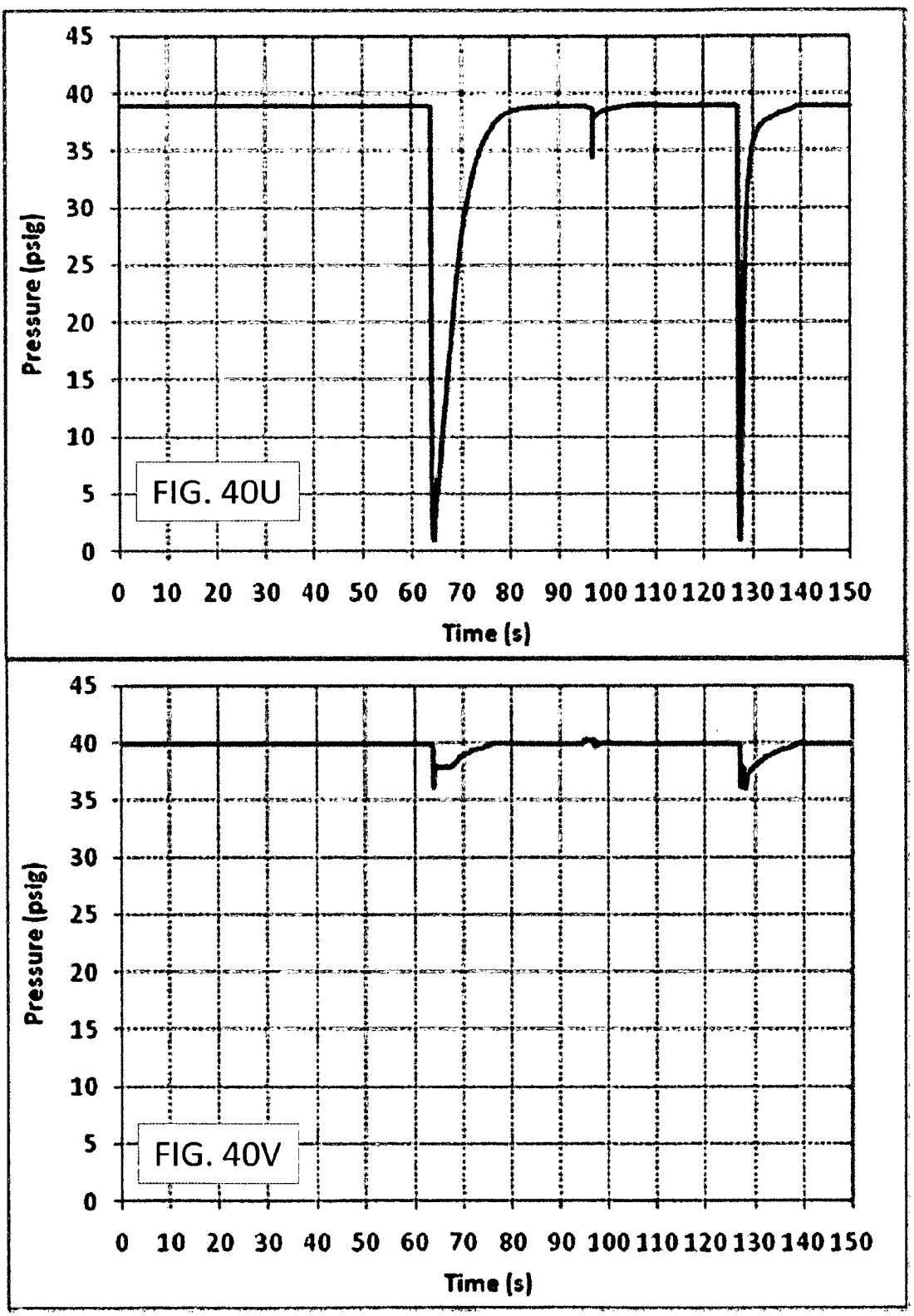

FLOW CONTROL DEVICES AND THEIR USE WITH EXPLOSIVE CARRIER GASES

PRIORITY APPLICATION

This application claims priority to, and the benefit of, U.S. Provisional Application No. 61/433,783 filed on Jan. 18, 2011, the entire disclosure of which is hereby incorporated herein by reference for all purposes.

TECHNOLOGICAL FIELD

This application is related to systems configured to permit chromatographic operations using an explosive carrier gas. In particular, certain embodiments described herein are directed to devices and methods for sampling vapors using an explosive carrier gas.

BACKGROUND

Chromatography systems use a mobile phase to transfer sample from component to another and as part of the separation. In gas chromatography (GC), the sample is vaporized and carried into a chromatographic column using a carrier gas. To maintain the sample in the vapor phase, high temperatures are often used in GC systems.

SUMMARY

In a first aspect, a sampling system configured to sample headspace vapor is provided. In certain embodiments, the system comprises a carrier gas fluid line and a flow control device coupled to the carrier gas fluid line. In some configurations, the flow control device can be configured to provide release of explosive carrier gas provided by the carrier gas fluid line in less than an explosive amount to void space in the sampling system.

In certain examples, the flow control device can be configured as a sampling device comprising a longitudinal shaft and an effective inner diameter to provide release of the explosive carrier gas in less than the explosive amount to void space in the sampling system. In certain instances, the effective internal diameter can be about 0.15 mm or less, e.g., 0.15 mm or less or 0.14 mm or less. In some examples, the sampling device comprises a variable inner diameter with at least some portion comprising an effective inner diameter of about 0.15 mm or less, e.g., 0.15 mm or less or 0.14 mm or less. In other examples, the flow control device can be configured as an inline restrictor between the carrier gas source and a sampling assembly, in which the restrictor is configured to provide release of the explosive carrier gas provided by the carrier gas fluid line in less than the explosive amount to void space in the sampling system. In certain embodiments, the flow control device can be configured as a mass flow controller positioned between the carrier gas source and a sampling assembly, in which the mass flow controller is operative to control the flow rate of explosive carrier gas to provide release of the explosive carrier gas provided by the carrier gas fluid line in less than the explosive amount to void space in the sampling system. In some examples, the system can include a fluid transfer line comprising an inner diameter effective to transfer sample to a chromatography column from the sampling device without substantial release of an explosive amount of the explosive carrier gas to void space in the sampling system. In additional examples, the effective inner diameter of the transfer line provides a pressure 15-20 psig at an explosive carrier gas flow rate of 15-20 mL/minute. In some examples, the effective inner diameter of the transfer line can be between about 0.2 mm and about 0.25 mm. In certain embodiments, the sampling system can include at least one active component in the void space of the sampling system, the at least one active component capable of causing explosion of the explosive carrier gas when released in an explosive amount. In other embodiments, the sampling system can include a detector fluidically coupled to the carrier gas fluid line and operative to use carrier gas from a carrier gas source fluidically coupled to the carrier gas fluid line as a gas source for detector operation.

In another aspect, a vapor sampling system comprising a sampling device effective to provide release of an explosive carrier gas in less than an explosive amount to void space in the vapor sampling system is described.

In certain embodiments, the sampling device comprises an effective internal diameter to provide the release of the explosive carrier gas in less than an explosive amount to the void space in the vapor sampling system. In some embodiments, the effective internal diameter can be about 0.15 mm or less, e.g., 0.15 mm or less or 0.14 mm or less. In other embodiments, the sampling device comprises a variable inner diameter with at least some portion comprising an effective inner diameter of about 0.15 mm or less, e.g., 0.15 mm or less or 0.14 mm or less. In certain examples, the vapor sampling system can include a fluid transfer line fluidically coupled to the sampling device and an injector, the fluid transfer line comprising an inner diameter effective to transfer sample from the sampling device without a substantial pressure drop. In some configurations, the effective inner diameter of the transfer line provides a pressure of 15-20 psig at an explosive carrier gas flow rate of 15-20 mL/minute. In other configurations, the effective inner diameter of the transfer line can be between about 0.2 mm and about 0.25 mm. In some embodiments, the vapor sampling system can include at least one active component in the void space of the vapor sampling system, the at least one active component capable of causing explosion of the explosive carrier gas when released by the sampling device in an explosive amount. In other embodiments, the vapor sampling system can be configured for use with use hydrogen as an explosive carrier gas, whereas in other examples explosive gases other than hydrogen could instead be used. In some embodiments, the system can be configured to reduce sample run time by at least 40% using hydrogen as a carrier gas when compared to using helium as a carrier gas. In other embodiments, the vapor sampling system can include a detector fluidically coupled to the sampling device.

In an additional aspect, a sampling device comprising a longitudinal shaft and an effective inner diameter to provide release of an explosive carrier gas in less than an explosive amount to void space in a vapor sampling system is disclosed.

In certain examples, the longitudinal shaft comprises the same effective inner diameter along its entire length. In other examples, the longitudinal shaft comprises a variable inner diameter with the effective inner diameter at some portion of the longitudinal shaft. In additional examples, the effective inner diameter can be present at a terminal end of the sampling device or may be present between two or more ports on the longitudinal shaft of the sampling device. In some examples, the effective inner diameter is about 0.15 mm or less, e.g., 0.15 mm or less or 0.14 mm or less. In other examples, the length of the longitudinal shaft is between 100 mm and 200 mm. In certain examples, the sampling device can be configured for use with a transfer line comprising an effective inner diameter to transfer sample from the sampling device without a substantial pressure drop. In certain embodiments, the effective inner diameter of the transfer line can be about 0.2 mm to about 0.25 mm. In some embodiments, the effective inner diameter of the transfer line provides a pressure of 15-20 psig at an explosive carrier gas flow rate of 15-20 mL/minute. In certain examples, the sampling device comprises a plurality of sections each comprising an effective inner diameter to provide release of the explosive carrier gas in less than an explosive amount to void space in the vapor sampling system. In some examples, the plurality of sections can be coupled to each other to provide a single sampling device. In other examples, a user can select a desired number of sections and couple them to each other to provide a sampling device.

In another aspect, a sampling system comprising a carrier fluid line configured to provide fluidic coupling between a carrier gas source and a sampling assembly, the system further comprising a restrictor in the carrier fluid line and between the carrier gas source and the sampling assembly, the restrictor configured to provide release of an explosive carrier gas in less than an explosive amount to void space in a sampling system is described.

In certain embodiments, the restrictor can be configured as a fixed restrictor. In other embodiments, the restrictor can be configured as a variable restrictor. In additional embodiments, the sampling system can also include a sampling device fluidically coupled to the restrictor, the sampling device in the sampling assembly and comprising a longitudinal shaft and an effective inner diameter to provide release of an explosive carrier gas in less than an explosive amount to void space in the sampling system. In other embodiments, the effective inner diameter of the sampling device is about 0.15 mm or less, e.g., 0.15 mm or less or 0.14 mm or less.

In an additional aspect, a sampling system comprising carrier fluid line configured to provide fluidic coupling between a carrier gas source and a sampling assembly, the system further comprising a flow controller in the carrier fluid line and between the carrier gas source and the sampling assembly, in which the flow controller is operative to provide a carrier gas flow rate effective to release an explosive carrier gas in less than an explosive amount to void space in a sampling system is provided.

In certain examples, the flow controller can be configured to control flow of explosive carrier gas up to about 450 mL per minute of explosive gas and up to an applied pressure of about 40 psig. In some embodiments, the system can also include a restrictor in the carrier fluid line and between the carrier gas source and the sampling assembly, the restrictor configured to provide release of an explosive carrier gas in less than an explosive amount to void space in a vapor sampling system. In other examples, the system can also include a sampling device fluidically coupled to the restrictor, the sampling device in the sampling assembly and comprising a longitudinal shaft and an effective inner diameter to provide release of an explosive carrier gas in less than an explosive amount to void space in the sampling system. In further examples, the effective inner diameter of the sampling device is about 0.15 mm or less, e.g., 0.15 mm or less or 0.14 mm or less.

In an additional aspect, a sampling system configured for use with an explosive carrier gas, the system comprising a sampling inlet and means for controlling release of the explosive carrier gas in a non-explosive amount to void space in the sampling system during introduction of sample into the sampling inlet is disclosed. In some embodiments, the means for controlling comprises a sampling device comprising a longitudinal shaft and an effective inner diameter to provide release of an explosive carrier gas in less than an explosive amount to void space in the sampling system. In other embodiments, the means for controlling comprises a restrictor fluidically coupled to a carrier gas source and the sampling inlet, the restrictor configured to provide release of an explosive carrier gas in less than an explosive amount to void space in the sampling system. In additional embodiments, the means for controlling comprises a mass flow controller fluidically coupled to a carrier gas source and the sampling inlet, the mass flow controller operative to provide a carrier gas flow rate effective to release an explosive carrier gas in less than an explosive amount to void space in the sampling system.

In another aspect, a sampling system configured to sample headspace vapor, the system comprising carrier gas fluid line and flow control means coupled to the carrier gas fluid line, the flow control means for releasing carrier gas provided by the carrier gas fluid line in less than an explosive amount to void space in the sampling system. In some embodiments, the flow control means comprises a sampling device comprising a longitudinal shaft and an effective inner diameter to provide release of an explosive carrier gas in less than an explosive amount to void space in the sampling system. In other embodiments, the flow control means comprises a restrictor fluidically coupled to a carrier gas source and the sampling inlet, the restrictor configured to provide release of an explosive carrier gas in less than an explosive amount to void space in the sampling system. In additional embodiments, the flow control means comprises a mass flow controller fluidically coupled to a carrier gas source and the sampling inlet, the mass flow controller operative to provide a carrier gas flow rate effective to release an explosive carrier gas in less than an explosive amount to void space in the sampling system.

In an additional aspect, a gas chromatography system comprising a temperature regulated column space configured to receive a chromatography column, a sampling system fluidically coupled to the column space and configured to provide sample to the chromatography column in the column space, the sampling system comprising a flow control device configured to provide release of explosive carrier gas provided by a carrier gas fluid line in less than an explosive amount to void space in the sampling system, and a detector fluidically coupled to the column space and configured to receive analyte from the chromatography column.

In certain embodiments, the sampling system and the detector are each configured to receive gas from the same carrier gas source. In other embodiments, the detector is configured as a flame detector. In some examples, the flame detector is a flame ionization detector. In other examples, the detector is configured as a plasma detector. In additional examples, the flow control device can be configured as a sampling device comprising a longitudinal shaft and an effective inner diameter to provide release of the explosive carrier gas in less than the explosive amount to void space in the sampling system. In some examples, the effective internal diameter is about 0.15 mm or less, e.g., 0.15 mm or less or 0.14 mm or less. In other examples, the sampling device comprises a variable inner diameter with at least some portion comprising an effective inner diameter of about 0.15 mm or less. In further examples, the flow control device can be configured as an inline restrictor between a carrier gas source and the sampling system, in which the restrictor is configured to provide release of the explosive carrier gas in less than the explosive amount to void space in the sampling system. In some embodiments, the flow control device can be configured as a mass flow controller between a carrier gas source and the sampling system, in which the mass flow controller is operative to control the flow rate of explosive carrier gas to provide release of the explosive carrier gas in less than the explosive amount to void space in the sampling system. In additional embodiments, the GC system can also include a fluid transfer line comprising an inner diameter effective to transfer sample to the chromatography column from the sampling system without release of an explosive amount of the explosive carrier gas to void space in the sampling system. In further embodiments, the effective inner diameter of the transfer line provides a pressure 15-20 psig at an explosive carrier gas flow rate of 15-20 mL/minute. In other embodiments, the effective inner diameter of the transfer line can be about 0.2 mm to about 0.25 mm. In additional embodiments, the system can include at least one active component in the void space of the sampling system, the at least one active component capable of causing explosion of the explosive carrier gas when released in an explosive amount. In some examples, the GC system can include an explosive carrier gas vent fluidically coupled to the sampling system, the vent configured to provide release of explosive carrier gas from void space in the sampling system to the atmosphere.

In another aspect, a method of facilitating use of an explosive carrier gas in a chromatography instrument, the method comprising providing a flow control device configured to provide release of explosive carrier gas provided by a carrier gas fluid line in less than an explosive amount to void space in a sampling system is provided.

In some embodiments, the method can include configuring the flow control device as a sampling device comprising a longitudinal shaft and an effective inner diameter to provide release of the explosive carrier gas in less than the explosive amount to void space in the sampling system. In other embodiments, the method can include configuring the effective inner diameter to be about 0.15 mm or less, e.g., 0.15 mm or less or 0.14 mm or less, for at least some portion of the longitudinal shaft. In certain embodiments, the method can include configuring the flow control device as an inline restrictor for insertion between a carrier gas source and a sampling assembly, in which the restrictor is configured to provide release of the explosive carrier gas in less than the explosive amount to void space in the sampling system. In some examples, the method can include configuring the flow control device as a mass flow controller for insertion between a carrier gas source and a sampling assembly, in which the mass flow controller is operative to control the flow rate of explosive carrier gas to provide release of the explosive carrier gas in less than the explosive amount to void space in the sampling system.

In an additional aspect, a kit comprising a flow control device configured to provide release of explosive carrier gas provided by a carrier gas fluid line in less than an explosive amount to void space in a sampling system, and instructions for using the flow control device with an explosive carrier gas to perform a chromatographic operation is provided. Illustrative chromatographic operations include sample injection, sample vial pressurization, sample separation and combinations thereof and other operations commonly performed using a GC system.

In certain embodiments, the flow control device can be configured as a sampling device comprising a longitudinal shaft and an effective inner diameter to provide release of the explosive carrier gas in less than the explosive amount to void space in the sampling system. In some examples, the effective inner diameter is about 0.15 mm or less, e.g., 0.15 mm or less or 0.14 mm or less. In other examples, the sampling device comprises a variable inner diameter. In additional examples, the kit can include a plurality of sampling devices each comprising a longitudinal shaft and an effective inner diameter to provide release of the explosive carrier gas in less than the explosive amount to void space in the sampling system. In some embodiments, the plurality of sampling devices can be configured to couple to each other to provide the flow control device. In other embodiments, at least two of the plurality of sampling devices comprise a different inner diameter. In certain embodiments, the flow control device can be configured as an inline restrictor for insertion between a carrier gas source and a sampling assembly, in which the restrictor is configured to provide release of the explosive carrier gas in less than the explosive amount to void space in the sampling system. In other embodiments, the flow control device can be configured as a mass flow controller for insertion between a carrier gas source and a sampling assembly, in which the mass flow controller is operative to control the flow rate of explosive carrier gas to provide release of the explosive carrier gas in less than the explosive amount to void space in the sampling system. In some examples, the kit can include at least one transfer line comprising an inner diameter effective to transfer sample to a chromatography column from the sampling system without release of an explosive amount of the explosive carrier gas to void space in the sampling system. In other examples, the kit can include a plurality of transfer lines. In some examples, at least two of the plurality of transfer lines comprise different inner diameters.

Additional features, aspect, examples and embodiments are described in more detail below.

BRIEF DESCRIPTION OF THE FIGURES

Certain embodiments are described with reference to the accompanying figures in which:

FIG. 40A-40X are pressure profiles obtained using the system of FIG. 39, in accordance with certain examples.

Figure 1:
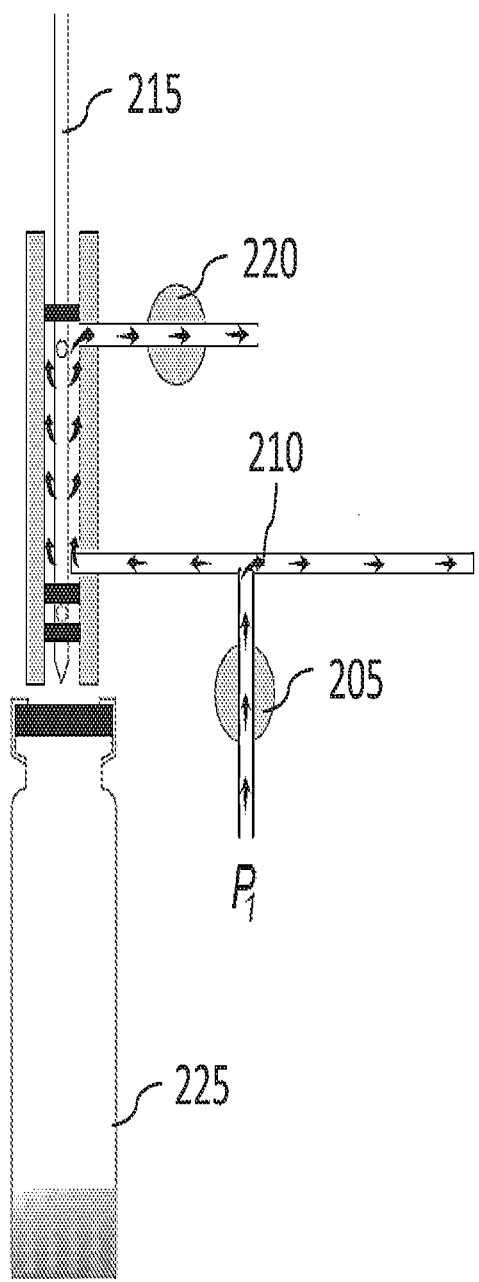
FIG. 1 is a schematic of a sampling system, in accordance with certain examples.

It will be recognized by the person of ordinary skill in the art, given the benefit of this disclosure, that certain dimensions or features in the figures may have been enlarged, distorted or shown in an otherwise unconventional or non-proportional manner to provide a more user friendly version of the figures. Where dimensions or values are specified in the description below, the dimensions or values are provided for illustrative purposes only. In addition, the particular coupling arrangement shown in certain figures is exemplary and one component in the figures can be positioned between different components if desired. Components which are described below as being fluidically coupled or where fluidic coupling is provided by a component refers to the ability of a fluid to pass between the components in at least one condition or arrangement but not necessarily all conditions and arrangements.

DETAILED DESCRIPTION

Certain embodiments are described below with reference to singular and plural terms in order to provide a user friendly description of the technology disclosed herein. These terms are used for convenience purposes only and are not intended to limit the devices, systems and methods as including or excluding certain features unless otherwise noted as being present in a particular embodiment described herein.

Certain examples described herein are directed to a system for sampling vapors. In some configurations, the system can include one or more components designed to limit or control release of an explosive carrier gas into internal void space of the system. Internal void space refers to the air space within an instrument housing (or the housing of a sampling system) or some portion thereof that is typically not used in the chromatographic operation but exists between instrument components and the instrument housing panels. In some examples such void space may receive heat from hot components or may convey fluids from one area to another that may cause an explosion, e.g., may be able to convey an explosive gas from one area to an open flame of a detector which can cause an explosion.

In certain embodiments, the systems, devices and methods described herein can be used with headspace sampling. In a typical headspace sampling operation, sample is placed into a vial, which is closed, equilibrated and pressurized. In headspace analysis, the vapor above the solid/liquid sample in the vial is sampled. The sample is typically present in a vapor tight vial that is placed in an oven and heated to a preset temperature. When equilibrium is reached between the solid/liquid phase and the vapor phase, the sample includes the volatile material in equilibrium between the solid/liquid sample and the vapor. An aliquot is then withdrawn from the closed vial and transferred to a gas chromatography (GC) system or pre-concentrated using a trap. Programmed pneumatic control (PPC) is typically used to provide electronic control of pressures and flow for carrier gases and other gases used in the system. This PPC control provides a pneumatic pressure balanced system. The headspace sample is introduced into a column without using a syringe, which avoids fractionation due to pressure changes in the syringe. Instead, a needle is present in the HS sampler and used to provide the sample to the GC column.

Figure 2:
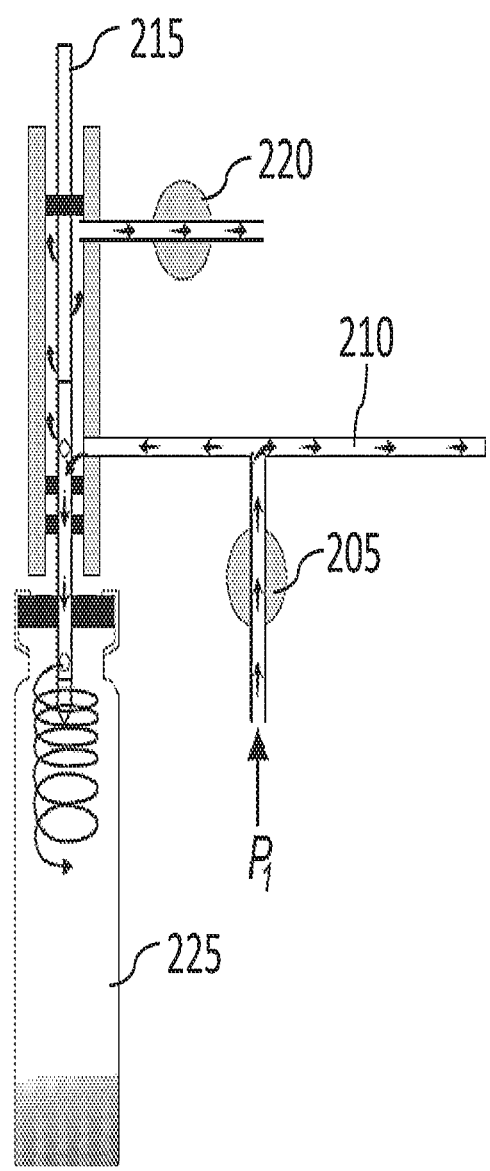
FIG. 2 is a schematic of the system of FIG. 1 with a sampling device inserted into a vial, in accordance with certain examples.
Figure 3:
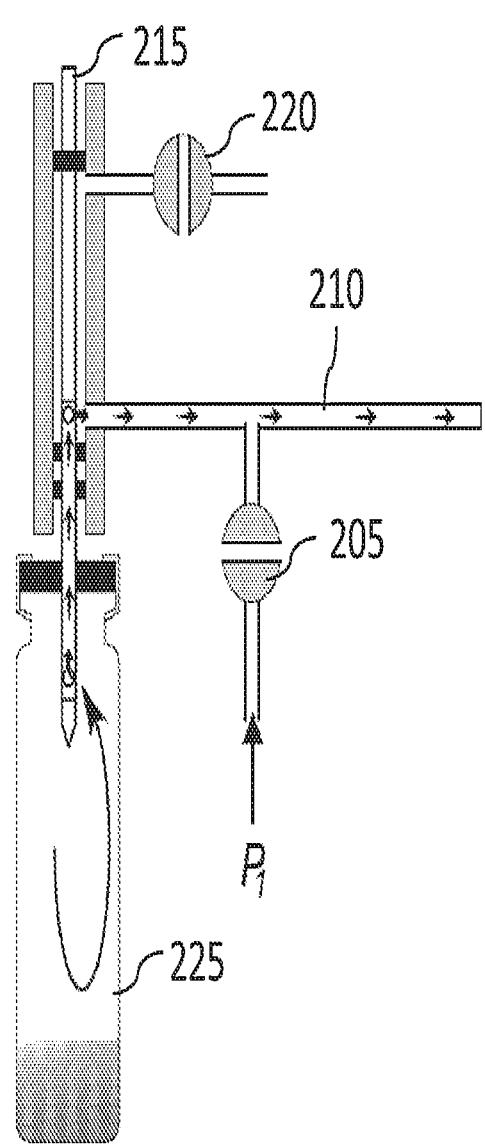
FIG. 3 is a schematic of the system of FIG. 2 in a configuration that permit sample to flow from the vial through a transfer line, in accordance with certain examples.

In certain embodiments, sample injection in HS analysis generally includes three steps. In a first step, also referred to as the standby step, the sampling needle is in an upper position. Carrier gas typically flows through a solenoid valve 205 (see FIG. 1) to the column (not shown) through a transfer line 210. At the same time, the needle cylinder 215 is purged by a small cross flow vented through a solenoid valve 220 and optionally a needle valve (not shown). This cross flow is typically used to prevent carry over between injections. The PPC controller (not shown) sets a pressure $P_1$ such that carrier gas flows in the direction of the arrows shown in FIG. 1. A vial 225 comprising vapor sample is shown in FIG. 1 for reference purposes only. In the second step, also referred to as the pressurization step, the sampling needle 215 moves to its lower position (see FIG. 2) piercing a septum of the sample vial 225. Carrier gas flows into the vial headspace, pressurizing it to equal the sampling head pressure $P_1$. In the third step (FIG. 3), also referred to as the injection phase, the solenoid valves 205 and 220 are closed, which stops the carrier gas flow. The pressurized gas in the vial flows onto the column or trap through the transfer line 210. After a pre-selected injection time, the solenoid valves 205 and 220 are re-opened which completes the sampling phase. Carrier gas will flow directly into the column and branches to the sample vial 225, which prevents additional sample vapor from reaching the column. The needle 215 is withdrawn from the vial 225, and a new vial (not shown) may be put or rotated into place (or the needle 215 may be rotated to the new vial), and the sampling process can begin again. In some embodiments, a trap may be present that is used to concentrate the sample prior to entry to the column. In certain configurations, sample adsorbs to the trap for a specified period and is then desorbed and provided to the column.

In certain embodiments, a typical head space sampler has several areas at high temperature. These include, but are not limited to, the oven, sampling needle, and transfer lines and trap if present. In some instances, the temperatures may exceed 200° C. or even up to 400° C. for the trap. These temperatures are high enough to promote explosion if explosive gases contact or are near these high temperature components. In a typical configuration, the needle temperature and transfer line temperature are each set about 5-10° C. higher than the oven temperature. In some instances the HS sampler can include suitable couplings to provide fluidic coupling to a carrier gas, which is typically a non-combustible has such as helium. The HS sampler may also include, or be used with, a heated transfer line which fluidically couples the sampling head of the HS to a GC. The sample moves through the sample line from the vial to the GC column. If desired, one or more components of the system can be split. For example, a split injector or split transfer line can be implemented such that only a portion of the sample is provided to the GC column.

Figure 4:
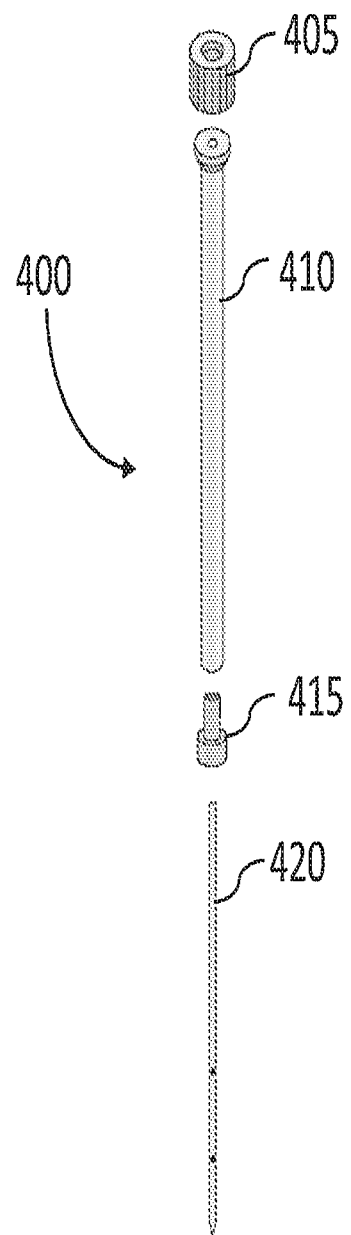
FIG. 4 is an illustration of a sampling device, in accordance with certain examples.

In certain embodiments, the sampling needle used with a conventional HS sampler is typically present in a needle assembly as shown in FIG. 4. The assembly 400 comprises a nut 405, a needle holder 410, a securing nut 415 and a needle 420. The needle assembly 400 is typically accessed through a door or cover on the instrument. To remove the needle assembly 400 from the instrument, the nut 405 is first removed. The needle holder 410 can then be lifted out of a rack. The securing nut 415 may then be loosened and the needle 420 can then be removed. In a typical configuration, the conventional needle 420 is about 140-145 mm long and has an internal diameter of about 0.50 microns.

In certain embodiments, it may be desirable to use an explosive carrier gas, e.g., hydrogen, as explosive gases such as hydrogen can provide desirable attributes including reduced run time, low viscosity and other attributes that are useful as a mobile phase in chromatographic separations. Illustrative explosive gases that can be used as carrier gases include, but are not limited to, hydrogen, oxygen, nitrous oxide and combinations thereof. Explosive carrier gases also include organic gases such as methane, ethane, propane and other hydrocarbon based gases. Use of a standard needle with an explosive carrier gas can present an explosive hazard. Referring again to FIGS. 2 and 3, as the needle 215 is inserted into the vial 225 (FIG. 2), carrier gas can escape as the needle 215 punctures the septum of the vial 225. Similarly, when the needle 215 is withdrawn from vial 225, carrier gas can escape from the needle 215. This carrier gas will vent into the internal void spaces of the vapor sampler. Depending on the particular carrier gas used, the flow rate of transfer may be on the order of liters per minute, which can result in very rapid build-up of explosive carrier gas within the instrument housing and/or the sampling system. The high needle, oven and transfer line temperatures may be high enough to cause combustion or explosion of an explosive carrier gas. In addition, active components such as motors, solenoid valves and the like may arc or spark which could result in explosion of the carrier gas built up in the void space.

While the systems, devices and methods described herein desirably are configured for use with an explosive gas, the carrier gas need not be comprised entirely of the explosive gas. For example, the carrier gas may be present as a mixture of an explosive gas and a non-explosive gas which might be capable of an explosion if exposed to the right conditions, e.g., hot system components, arc, sparks or open flames. Where a mixture of gases are used as a carrier gas, the devices, systems and methods described herein can be configured such that the explosive component of the mixture of gases is released in less than an explosive amount to void space in the vapor sampling system.

Figures 5, 6, 7:
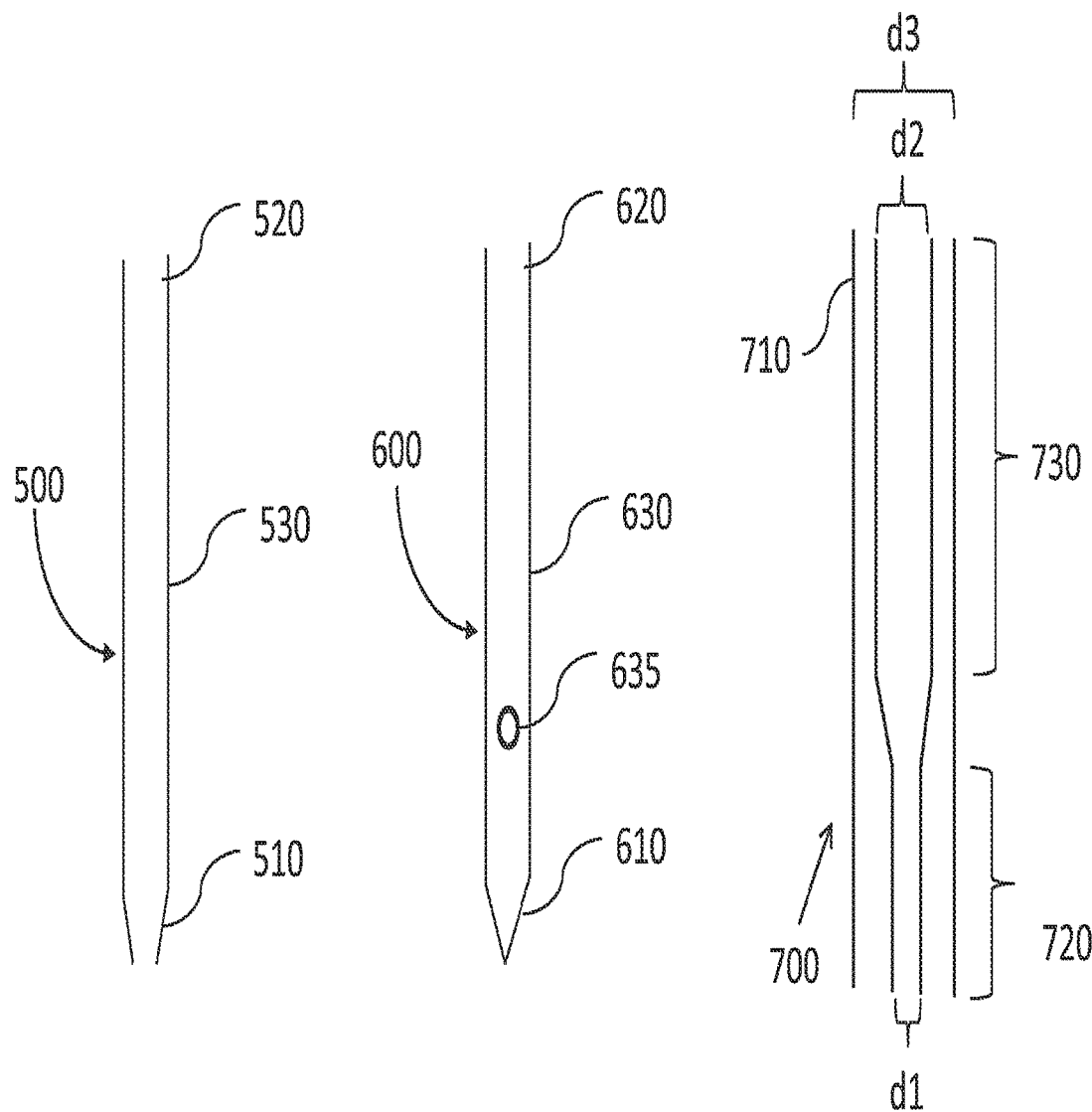
FIG. 5 is an illustration of a sampling device comprising an opening at a terminal end, in accordance with certain examples.
FIG. 6 is an illustration of a sampling device comprising an opening along the longitudinal shaft, in accordance with certain examples.
FIG. 7 is an illustration of a sampling device comprising a variable inner diameter, in accordance with certain examples.

In certain examples, a sampling device comprising an effective inner diameter to provide release of an explosive carrier gas in less than an explosive amount to void space in a vapor sampling system is provided. In some instances, the sampling device may comprise a substantially uniform diameter along its length, whereas in other examples one or more regions of smaller diameter, e.g., restrictions, may be present in the sampling device. In some examples, the sampling device can be used with one or more additional devices present in the sampling system. For example, a restrictor or flow controller can be used in a transfer line or in a fluid line between the carrier gas and the needle such that additional control of explosive carrier gas can be obtained. Referring to FIG. 5, a sampling device 500 configured as a needle comprising an effective inner diameter to provide release of an explosive carrier gas in less than an explosive amount to void space in a vapor sampling system is shown. The sampling device comprises a first end 510, a second end 520 and a longitudinal shaft 530 between the first end 510 and the second end 520. The first end 510 can be configured for insertion into a vial to pressurize the vial with the carrier gas. For example, the first end 510 can be tapered such that it can pierce a septum within the cap of a vial. In the configuration shown in FIG. 5, the needle 500 comprises an opening at the first end 510 to permit passage of carrier gas through the opening 510. If desired, the opening or openings can be positioned along the longitudinal shaft of the needle instead. For example and referring to FIG. 6, as sampling device 600 comprising a first end 610, a second end 620, and a longitudinal shaft 630 between the first end 610 and the second end 630 is shown. The first end 610 is closed such that carrier gas passing through the sampling device 600 does not exit at the first end 610. Instead, an aperture or opening 635 in the longitudinal shaft of the sampling device 600 is present to permit exiting of carrier gas through the sampling device 600. In some embodiments, two or more openings can be present along the longitudinal shaft, and the openings may be sized similarly or may be sized differently. In operation, the sampling device 600 would be inserted into a vial at a sufficient depth such that the opening 635 would be within the vial. If desired, the sampling device 600 can include more than a single opening in the longitudinal shaft 630. Also, the sampling device 600 can be configured such that one or more openings are present in the longitudinal shaft 630 and an opening may be present at the first end 610. By selecting the diameter of the openings and their locations, the flow rate of carrier gas to void spaces within an instrument can be better controlled.

In some embodiments and referring to FIGS. 5 and 6 again, the inner diameter of the sampling devices 500 and 600 can be selected such that release of an explosive carrier gas by the sampling device is provided at less than an explosive amount to void space in a vapor sampling system. By selecting an inner diameter that is substantially smaller than the inner diameter of conventional needles used in headspace sampling systems, the amount of explosive gas released to the void space can be reduced below levels needed to support an explosion. In conventional systems, sampling devices with such small diameters have not been used as they can easily plug or become clogged. In some embodiments, the inner diameter of the sampling device, or some portion thereof, may be about 0.15 mm or less, more particularly about 0.14 mm or less, e.g., about 0.125 mm or less.

In certain examples, the sampling device need not have the same diameter along the length of the longitudinal shaft. For example, one or more selected portions of the longitudinal shaft may comprise an effective inner diameter such that release of an explosive carrier gas by the sampling device is provided at less than an explosive amount to void space, whereas other portions or sections of the sampling device may have a larger inner diameter. In some instances it may be difficult to provide sampling devices having small uniform, inner diameters along their entire length. As such, a sampling device comprising one or more sections comprising an effective inner diameter such that release of an explosive carrier gas by the sampling device is provided at less than an explosive amount to void space can be assembled with higher reproducibility. Referring to FIG. 7, a sampling device 700 configured as a needle comprises a longitudinal shaft 710 comprising a variable inner diameter is shown. At a first portion 720, the longitudinal shaft may comprise an effective diameter d1 such that release of an explosive carrier gas by the sampling device is provided at less than an explosive amount to void space. At a different portion 730, the longitudinal shaft may comprise a diameter d2, which is greater than d1, such that the diameter d2 by itself generally would not be effective to provide release of an explosive carrier gas at less than an explosive amount to void space. As shown in FIG. 7, the outer diameter d3 of the sampling device 700 is substantially uniform along the longitudinal shaft 710, but if desired, the outer diameter d3 may also be varied as well. Where ports are present along the longitudinal shaft 710, at least one port can be positioned within the first portion 720.

In certain examples, the narrower portion 720 of the longitudinal shaft 710 can be positioned at a terminal end of the sampling device 700, e.g., an end that either couples to the carrier gas or is inserted into a vial. In some embodiments, the narrower portion 720 can be present at a central portion of the sampling device 700 that is between the terminal ends of the sampling device 700. In other configurations, more than one narrower portion 720 may be present, e.g., 2, 3, 4 or 5 sections can be present each having an inner diameter that is narrower than the largest inner diameter of the sampling device. In instances where more than a single narrow section is present, the narrow sections may have the same inner diameter or may have different inner diameters. For example, a sampling device comprising two narrow sections can be present with one narrow section comprising an inner diameter of about 0.15 mm and the other section comprising an inner diameter of about 0.14 mm or less.

In certain embodiments, the narrow section 720 may have an inner diameter that is at least 0.05 mm less than the inner diameter of the section 730, more particularly the narrow section 720 has an inner diameter that is at least 0.075 mm less than the inner diameter of the section 730, e.g., the narrow section 720 has an inner diameter of 0.15 mm or less and the section 730 has an inner diameter that is greater than or equal to 0.25 mm. The length of the narrower section may vary and may be the entire length of the needle or may be a section of the needle, e.g., a section that is about 40-55 mm long, more particularly a section that is about 45-50 mm long such as, for example, 48 mm long. In certain instances, the narrow section has an inner diameter of 0.15 mm or less and the inner diameter of the section 730 is greater than 0.15 mm. In certain embodiments, the needle may comprise one or more longitudinal ports each of which can permit exit of carrier gas. In certain embodiments, the needle can be configured such that flow of carrier gas between two longitudinal ports is effective to permit release of explosive carrier gas to void space in a sampling system.

In certain examples, if desired, the sampling devices can be produced as two or more separate sections that can be coupled to each other using suitable fittings, ferrules or couplers. For example, a first section can be produced comprising an inner diameter effective to provide release of an explosive carrier gas at less than an explosive amount to void space, and a second section can be produced that has a larger internal diameter than the first section. The two sections can be coupled to each other to provide a sampling device having a suitable length for use in a headspace sampling assembly. In some instances where the sampling device has substantially the same inner diameter along its length, e.g., an inner diameter effective to provide release of an explosive carrier gas at less than an explosive amount to void space, the sampling device can be produced in a plurality of small sections which can be coupled to each other through suitable couplings. Such a plurality of sections can permit replacement of one or more sections should they become clogged without having to replace the entire sampling device. In addition, it may be easier to manufacture smaller sections with more uniform inner diameters than manufacturing a single large sampling device with a desired inner diameter.

In certain embodiments, a system for sampling vapors may include more than a single type of sampling device. For example, a first sampling device may be present and used with non-explosive carrier gases, and a second sampling device configured to provide release of an explosive carrier gas at less than an explosive amount to void space can be used with an explosive carrier gas. The sampling devices may be present in separate sampling assemblies or may be switched out by an end user as desired. In some instances, two different sampling assemblies can be present in a single instrument. For example, with selection of the particular carrier gas by an end user, the appropriate sampling assembly may be actuated and used by the instrument to sample vapors. If an explosive carrier gas is used, then a sampling assembly comprising a sampling device configured to provide release of an explosive carrier gas at less than an explosive amount to void space can be used. If a non-explosive gas is used, then a conventional sampling assembly may be used or the sampling assembly suitable for use with the explosive carrier gas could be used instead. Where two or more sampling assemblies are present, suitable valving and connectors can be implemented such that the non-active sampling assembly does not receive any carrier gas during operation of the instrument. For example, a solenoid valve can be present in fluid lines and actuated to provide carrier gas to the desired sampling assembly, e.g., a 3-way solenoid valve can be used and actuated to provide fluidic coupling between the carrier gas source and a desired sampling assembly.

Figures 8, 9:
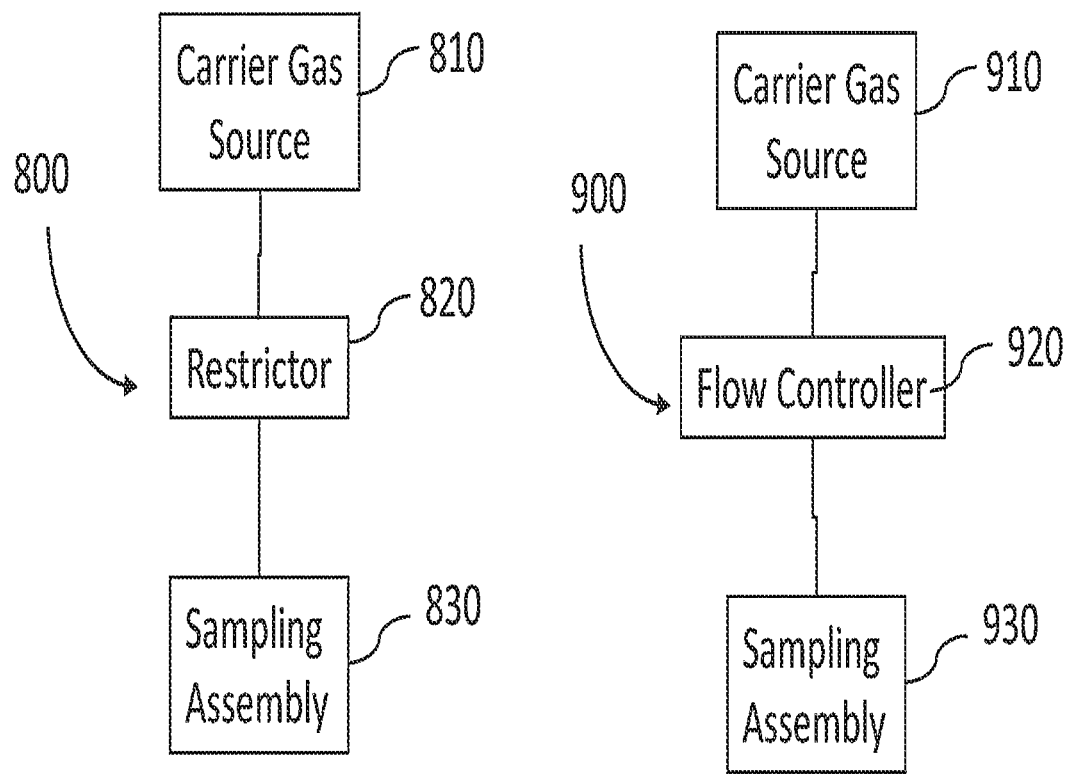
FIG. 8 is a block diagram of a system comprising a restrictor, in accordance with certain examples.
FIG. 9 is a block diagram of a system comprising a flow controller, in accordance with certain examples.

In certain embodiments, the sampling system can be configured with an inline restrictor between the carrier gas supply and the sampling assembly. For example, a fixed restrictor can be placed between the carrier gas source, e.g., a PPC manifold, and the headspace sampling assembly to control the flow of explosive gas to the headspace sampling assembly. An illustration of a system comprising a restrictor is shown in FIG. 8. The system 800 comprises a carrier gas source 810 fluidically coupled to a restrictor 820. The restrictor 820 is fluidically coupled to a sampling assembly 830, which may include a conventional sampling device or may include a sampling device as described herein, e.g., one that is configured to provide release of an explosive carrier gas at less than an explosive amount to void space.

In certain examples, the restrictor 820 can be configured as a fluid line comprising a smaller internal diameter than other fluid lines used to provide fluidic coupling between the carrier gas source 810 and the sampling assembly 830. For example, the inner diameter of the restrictor 820 can be about 20%, 30%, 40% or 50% smaller than the inner diameter of the fluid lines coupling the gas source 810 and the sampling assembly 830 to reduce the overall flow rate of carrier gas to the sampling assembly 830 and to the void space of the system. In some instances, the restrictor 820 can be configured such that a flow rate of 400 mL/minute or less is provided to the sampling assembly 830. In certain instances, the restrictor is operative to slow the flow rate of explosive carrier gas to the sampling assembly so that insertion of the needle of the sampling assembly into a vial or removal of the needle from the vial does not provide release of an explosive carrier gas in an explosive amount to void space. By selecting the inner diameter of the restrictor to be a suitable diameter, the amount of explosive carrier gas that can reach void space will be lower than the level needed to support an explosion.

In certain embodiments, the inner diameter of the restrictor 820 can be selected based on the particular type of explosive carrier gas used. For example, where hydrogen is used as a carrier gas the inner diameter of the restrictor may be different than where methane is used as an explosive carrier gas. In some embodiments, the restrictor size can be matched to the particular carrier gas to be used. For example, a kit comprising a plurality of restrictors each configured for use with a particular carrier gas can be obtained by an end user. The particular restrictor suitable for use with a selected explosive carrier gas can be selected and installed between the carrier gas supply and the sampling assembly such that explosive gas will not be provided to void space of the system in an explosive amount.

In other embodiments, the restrictor 820 can be configured as an adjustable restrictor, e.g., a needle valve or the like, such that flow through the restrictor 820 may be adjusted based on the particular sampling and/or chromatography conditions. For example, it may be desirable to use a higher flow rate with one explosive gas as compared to the flow rate used when using a different explosive gas. The opening size of the restrictor 820 can be varied, e.g., through software control or through manual adjustment, to provide a desired flow rate of the explosive carrier gas.

In certain examples, a restrictor can be used with one or more of the sampling devices described herein. For example, a sampling device comprising a longitudinal shaft and an effective inner diameter to provide release of an explosive carrier gas in less than an explosive amount to void space in a vapor sampling system can be used in combination with a restrictor to provide for better control of gas flows in the sampling system. In some embodiments, a sampling device comprising a longitudinal shaft and an effective inner diameter to provide release of an explosive carrier gas in less than an explosive amount to void space in a vapor sampling system can be used in combination with two or more restrictors to provide for better control of gas flows in the sampling system. In certain instances, more than a single sampling device can be present and each sampling device can be used with the same type of restrictor or may be used with a different type of restrictor.

In certain examples, the restrictor can be replaced with a flow controller that can be adjusted in software or adjusted mechanically by an end-user. For example and referring to FIG. 9, a sampling system 900 can include a flow controller 920 can be placed in-line between a carrier gas source 910 and a sampling assembly 930 to control the flow rate of carrier gas provided the sampling assembly 930. In some configurations, the flow controller 920 can be a mass flow controller (MFC). A typical MFC is configured to control the flow rate of a particular type of gas or gases over a desired flow rate range. Where a MFC is present, it may be a digital MFC or an analog MFC depending on the types and nature of the carrier gases that can be used with the system. A typical MFC comprises an inlet port, an outlet port, a mass flow sensor and proportional valve that can be adjusted to control the flow rate. A signal from the system is sent to the MFC, and the proportional valve can be adjusted until the mass flow sensor detects the desired flow rate. If desired, more than a single flow controller can be present in the system to provide for additional control of gas flows in the system.

In some embodiments, the flow controller, e.g., MFC, can be used in combination with a restrictor as described herein. For example, a restrictor can be placed in-line between a carrier gas source and a sampling assembly, and the restrictor can be positioned between the carrier gas source and the flow controller or can be positioned between the flow controller and the sampling assembly. In some configurations, the system can include two or more restrictors with all restrictors being between the carrier gas source and the flow controller or between the flow controller and the sampling assembly. In other configurations where two or more restrictors are present, at least one restrictor may be between the carrier gas source and the flow controller and the other restrictor can be between the flow controller and the sampling assembly. It may be desirable to use a restrictor in combination with a flow controller as the restrictor can provide for a fixed flow rate, and the overall flow rate may be further adjusted using the flow controller.

In certain examples, a flow controller can be used with one or more of the sampling devices described herein. For example, a sampling device comprising a longitudinal shaft and an effective inner diameter to provide release of an explosive carrier gas in less than an explosive amount to void space in a vapor sampling system can be used in combination with a flow controller to provide for better control of gas flows in the sampling system. In some embodiments, a sampling device comprising a longitudinal shaft and an effective inner diameter to provide release of an explosive carrier gas in less than an explosive amount to void space in a vapor sampling system can be used in combination with a flow controller and a restrictor to provide for better control of gas flows in the sampling system. In certain instances, more than a single restrictor or more than a single flow controller can also be present and used in combination with one or more of the sampling devices described herein.

In certain embodiments, the systems disclosed herein can include driers or molecular sieves to remove any water within the carrier gas. In addition, particulate filters or other filters can be present in-line to remove any suspended solids or solid materials that may interfere with the analysis or clog the sampling device. If desired, pressure regulators, pressure sensors and the like may also be present to provide for adjustment and/or feedback of carrier gas flows in the system.

In certain embodiments, the sampling systems described herein can be used with a chromatography column including wide bore columns, narrow bore columns, capillary columns and other chromatography columns. The use of an explosive carrier gas can provide desirable attributes when used with a capillary column including reduced overall run time compared to using conventional gases, e.g., helium, as a mobile phase. The chromatography column is configured to be inserted into a column space with a GC system and can be fluidically coupled to a transfer line at one end and another component, such as a detector, at another end. The chromatography column typically resides within an oven in the column space which can provide for temperature control of the column. For example, temperature programming is often used to ramp the oven temperature between two end points and induce elution of the various components of the sample from the column.

In certain embodiments, the detectors of the chromatography systems described herein can vary. In some embodiments, the detector may be a flame ionization detector (FID), a thermal conductivity detector (TCD), a thermionic detector (TID), an electron capture detector (ECD) an atomic emission detector (AED), a flame photometric detector (FPD), a mass spectrometer (MS) and other detectors and spectrometers commonly used with, or hyphenated to, gas chromatography systems. In some examples, the detector may be a plasma detector or may include a plasma such as, for example, an inductively coupled plasma (ICP) or a capacitively coupled plasma (CCP).

In certain examples, the devices described herein can be used in a GC system that includes a first gas used as a carrier gas and a second gas used as a gas source for a detector. For example, hydrogen can be used as a carrier gas and a mixture of hydrogen/oxygen can be used as a gas for the detector. The GC system can include pressure sensors, a PPC manifold, fluid lines, ferrules, fitting and other devices effective to couple components of the system to each other. In some examples, the GC system is computer controlled such that a user selects parameters through a graphical user interface (GUI) which are implemented by control boards electrically coupled to the computer.

Figure 10:
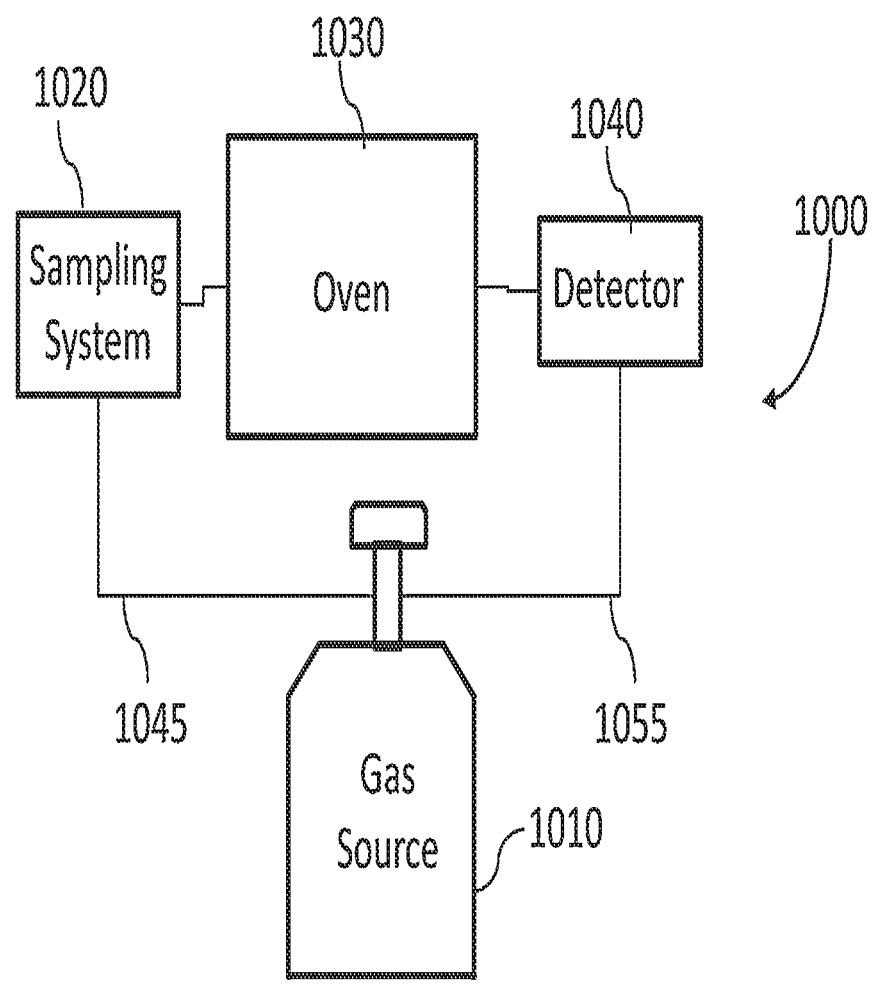
FIG. 10 is a block diagram of a GC system configured to use as gas source as a carrier gas and a gas source for a detector, in accordance with certain examples.

In some instances, the explosive carrier gas can be used both as a carrier gas and as a gas source that permits operation of the detector. For example, hydrogen gas can be used as a carrier gas and simultaneously used to provide a fuel source that permits operation of a flame ionization detector (FID). The FID typically operates by mixing hydrogen gas and air and electrically igniting the hydrogen/air mixture. Many analytes produce ions and electrons that are conductive when the analytes are exposed to the flame of an FID. The current produced by the ions and electrons can be detected using suitable electronics, e.g., a high impedance operational amplifier. One attribute of an FID is that detector response is less sensitive to changes in flow rate than other types of detectors. In addition, most FIDs are insensitive toward noncombustible gases such as water, carbon dioxide, sulfur dioxide and nitric oxides. An illustrative block diagram of a GC system that uses an explosive carrier gas as both the mobile phase and the gas source for an FID is shown in FIG. 10. The system 1000 includes a carrier gas source 1010, a sampling system 1020, an oven 1030 comprising a column space configured to receive a chromatography column, and a detector 1040. The sampling system 1020 is fluidically coupled to the carrier gas source 1010 through a fluid line 1045. The detector 1040 is fluidically coupled to the same carrier gas source 1010 through a fluid line 1055. In the system of FIG. 10 only a single gas source 1010 is present, which results in a substantial reduction of the system footprint and reduced overall operating costs. If desired, one or more additional gas sources can be fluidically coupled to either the sampling system 1020 or the detector 1040. In addition, it may be desirable to use different explosive gases as the carrier gas and as the gas used in the detector 1040. For example, the sampling system 1020 may use hydrogen as a carrier gas, and the detector 1040 may use oxygen as a gas source. Also, either fluid flow can be mixed with ambient air to provide a desired explosive gas/air mixture for use as either the carrier gas or the gas used by the detector 1040. In the system of FIG. 10, the sampling system 1020 typically comprises one or more of the flow control devices described herein, e.g., a sampling device, restrictor and/or flow controller.

In certain embodiments, the sampling system can also include an explosive carrier gas vent to further reduce the likelihood of explosion. For example, adjacent to or near the sampling head, a port, tubing or the like can be present to provide for evacuation of explosive carrier gas out of the void space of the system and to the atmosphere. If desired, the port can be coupled to a fan or vacuum to provide for positive air flow out of the void space and to the atmosphere. Removal of air from the void space can affect the temperature of the sampling head and/or transfer line, and temperature can be adjusted by the system to account for removal of air by the vent. In some embodiments, a vent fan may be started at a desired frequency, and the system is permitted to equilibrate to a desired temperature prior to injection of any samples.

In certain embodiments, the flow control devices described herein can be used in one or more chromatographic methods. For example, explosive carrier gas can be provided to equilibrate the sampling system. The sampling device can be inserted into a vial to pressurize the vial and equilibrate its pressure with the system. Sample can then be permitted to enter a transfer line fluidically coupled to a column. After separation by the column, eluted analyte can be detected using a suitable detector fluidically coupled to the column. The results can be displayed using a computer screen or more be printed out or stored.

In certain embodiments, methods of facilitating chromatography using one or more of the devices described herein are provided. For example, a method comprising providing a flow control device configured to provide release of explosive carrier gas provided by a carrier gas fluid line in less than an explosive amount to void space in a sampling system can be used to facilitate chromatography. In some embodiments, the method can include configuring the flow control device as a sampling device comprising a longitudinal shaft and an effective inner diameter to provide release of the explosive carrier gas in less than the explosive amount to void space in the sampling system. In other embodiments, the method can include configuring the effective inner diameter to be about 0.15 mm or less, e.g., 0.15 mm or less or 0.14 mm or less. In certain embodiments, the method can include configuring the flow control device as an inline restrictor for insertion between a carrier gas source and a sampling assembly, in which the restrictor is configured to provide release of the explosive carrier gas in less than the explosive amount to void space in the sampling system. In some examples, the method can include configuring the flow control device as a mass flow controller for insertion between a carrier gas source and a sampling assembly, in which the mass flow controller is operative to control the flow rate of explosive carrier gas to provide release of the explosive carrier gas in less than the explosive amount to void space in the sampling system.

In other embodiments, the devices and systems described herein can be provided or packaged in kit form such that a user may select the desire components for use in a chromatography system. For example, a kit comprising a flow control device configured to provide release of explosive carrier gas provided by a carrier gas fluid line in less than an explosive amount to void space in a sampling system can be provided. Instructions for using the flow control device with an explosive carrier gas to perform a chromatographic operation can also be provided. Illustrative chromatographic operations include sample injection, sample vial pressurization, sample separation and combinations thereof and other operations commonly performed using a GC system.

In certain embodiments, the flow control device can be configured as a sampling device comprising a longitudinal shaft and an effective inner diameter to provide release of the explosive carrier gas in less than the explosive amount to void space in the sampling system. In some examples, the effective inner diameter is about 0.15 mm or less, e.g., 0.15 mm or less or 0.14 mm or less. In other examples, the sampling device comprises a variable inner diameter. In additional examples, the kit can include a plurality of sampling devices each comprising a longitudinal shaft and an effective inner diameter to provide release of the explosive carrier gas in less than the explosive amount to void space in the sampling system. In some embodiments, the plurality of sampling devices can be configured to couple to each other to provide the flow control device. In other embodiments, at least two of the plurality of sampling devices comprise a different inner diameter. In certain embodiments, the flow control device can be configured as an inline restrictor for insertion between a carrier gas source and a sampling assembly, in which the restrictor is configured to provide release of the explosive carrier gas in less than the explosive amount to void space in the sampling system. In other embodiments, the flow control device can be configured as a mass flow controller for insertion between a carrier gas source and a sampling assembly, in which the mass flow controller is operative to control the flow rate of explosive carrier gas to provide release of the explosive carrier gas in less than the explosive amount to void space in the sampling system. In some examples, the kit can include at least one transfer line comprising an inner diameter effective to transfer sample to a chromatography column from the sampling system without release of an explosive amount of the explosive carrier gas to void space in the sampling system. In other examples, the kit can include a plurality of transfer lines. In some examples, at least two of the plurality of transfer lines comprise different inner diameters.

Certain specific examples are described to illustrate some of the novel attributes of the technology described herein.

Example 1

The flow rate of hydrogen escaping from a standard sampling needle was measured over a range of applied inlet pressures. For the testing, a spare sampling head was obtained and its inlet was connected to a mechanical pressure regulator that was connected to a hydrogen gas supply. The three outlets of the sampling head were sealed. The needle was pushed through a cylindrical piece of silicone rubber and positioned so that the lower orifice was exposed. One end of a length of ¼" soft silicone tubing was pushed over the piece of silicone rubber and the other end was connected to a flow measuring device. An electronic flowmeter of the type used for general GC purposes was inadequate. The flow rates observed were far higher than the 500 mL/min limit on these devices. A combination of a 100 mL bubble flow meter and using the water-displacement technique with an inverted 500 mL measuring cylinder filled with water in a large beaker of water were used to make the measurements in this example.

Figure 11:
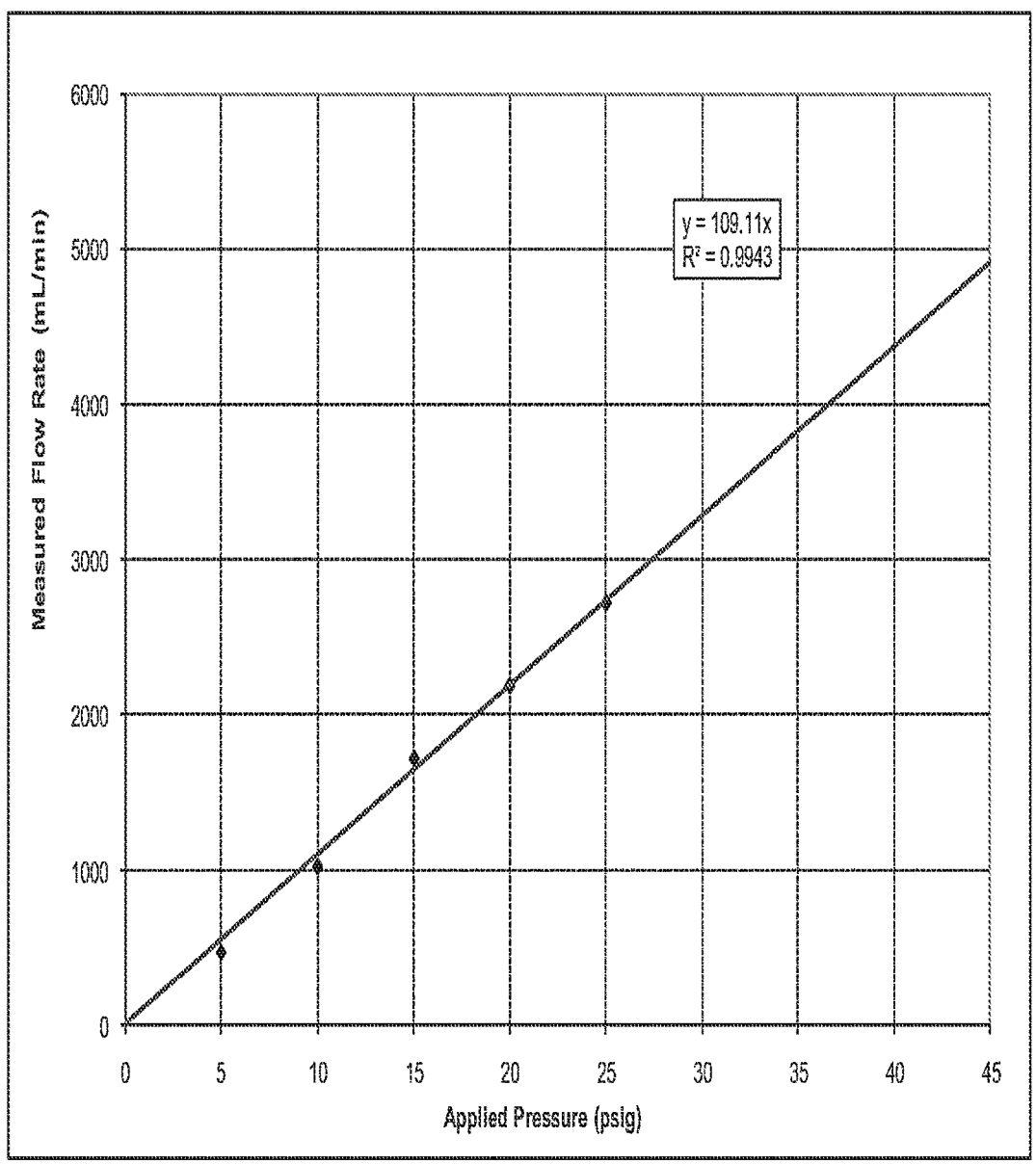
FIG. 11 is a graph of how the flow rate of escaping hydrogen varies with applied pressure, in accordance with certain examples.

Referring to FIG. 11, a graph of how the flow rate of escaping hydrogen varies with applied pressure is shown. The two lowest points were measured with the bubble flowmeter; the rest used the water-displacement method. These flow rates were much higher than expected.

Example 2

The time that the needle outlet used in Example 1 was exposed to the air inside the instrument during an analytical cycle was established. From this information, the volume of hydrogen released was calculated for each analysis. The same setup as used in Example 1 was used.

The distance between the lowest seal in the sampling head and the top of the thermostatting oven assembly was measured at 11 mm. The distance between the top of the thermostatting oven and the top of a vial inside it was 16 mm. Thus the total distance covered by the exposed needle orifice was 27 mm, 16 mm of which would be inside the thermostatting oven.

A video recording (not shown) was taken of the sampling head driving the needle up and down. From viewing the video frame by frame, it was possible to calculate the speed at which the needle moved down and up. Going down, the needle travelled 43 mm in 13 video frames at 15 frames/s which is equivalent to 43/(13/15)=50 mm/s. Coming up, the needle travelled 43 mm in 28 video frames at 15 frames/s which is equivalent to 43/(28/15)=23 mm/s. These results are summarized in Table 1.

TABLE 1

| | Exposed Time (s) | | |
|---|---|---|---|
| | Moving Down | Moving Up | Total |
| Above Vial Oven | 0.22 | 0.48 | 0.70 |
| Within Vial Oven | 0.32 | 0.70 | 1.03 |
| Total | 0.55 | 1.18 | 1.73 |

Thus for one analysis cycle, it will be expected that the hydrogen will vent for a total of about 1.73 seconds with 60% of this time venting into the heated vial oven.

Example 3

Figure 12:
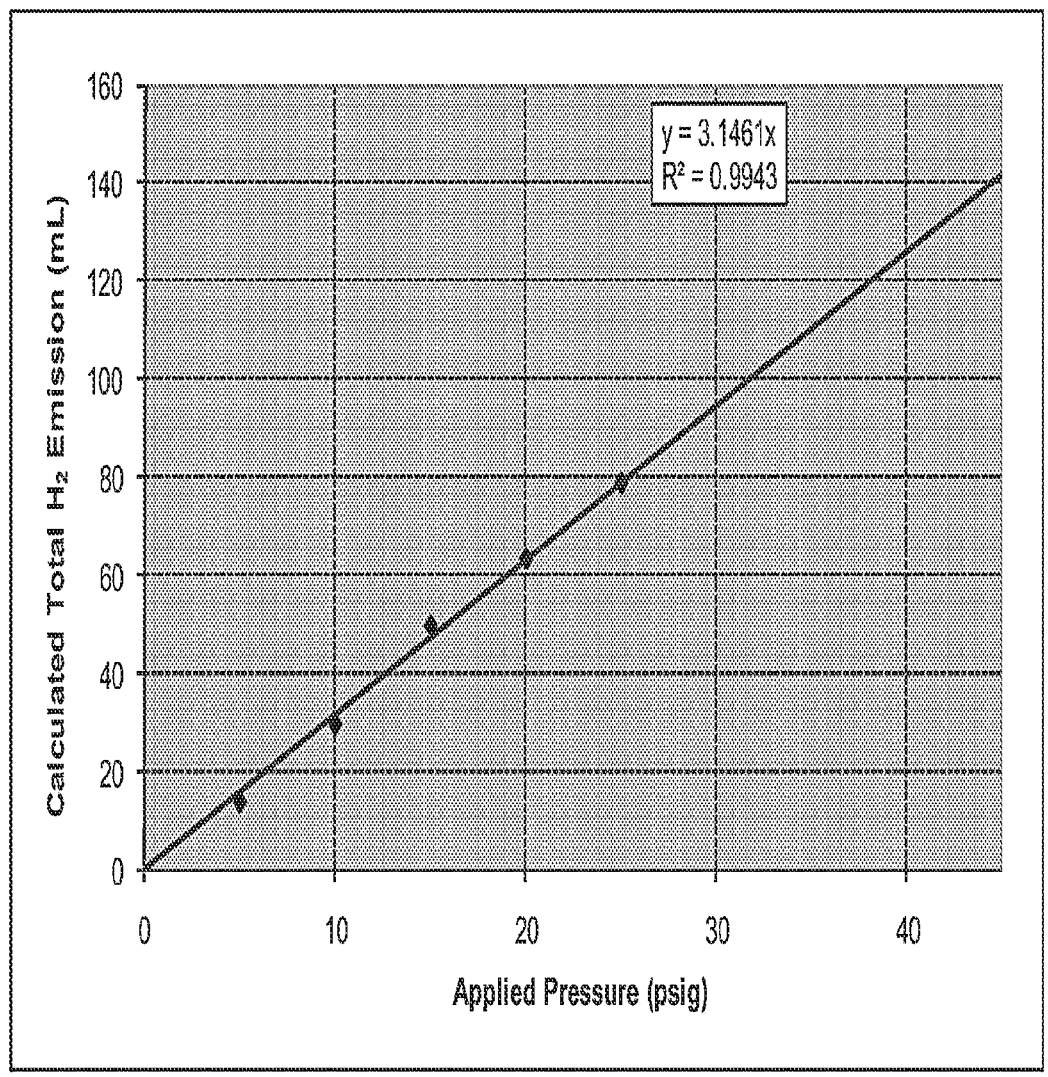
FIG. 12 is a graph showing the calculate volume of escaping hydrogen from standard head space (HS) sampling needle over a range of applied pressures, in accordance with certain examples.

From the information obtained in Examples 1 and 2, the volume of escaping hydrogen from standard head space (HS) sampling needle over a range of applied pressures for each analytical cycle was calculated. The results are shown in FIG. 12.

From the calculations, it appears that the hydrogen that would be vented from the standard sampling needle would be typically in the range of 10 to 100 mL. Approximately 60% of this would be released into the heated vial oven area and the remainder into the area above the oven. All these spaces are semi-enclosed with active electronics in the area. The minimum hydrogen concentration which will support an explosion is about 4%. The hydrogen release will occur in two stages as the needle goes down and then when it returns up—typically 1 minute apart. Each release is almost instantaneous. The second release emits the larger volume because the needle travels slower and may release 70 mL of hydrogen gas. This released hydrogen gas would need to diffuse quickly into a volume of air that is greater than 1750 mL to keep the concentration below the explosive limit. There is also the accumulation effect—each time an emission is made, unless the hydrogen is cleared from the last emission, the concentration will build up. This will be a factor of the analytical cycle time. Users using hydrogen are likely to be looking at fast analyses perhaps down to a cycle time of less than 2 minutes or even approaching 1 minute. In sum, using a standard sampling needle, hydrogen gas can be released into the void space of the instrument at a very high flow rate that can exceed several liters per minute.

Example 4

A series of sampling devices configured as needles having an inner diameter of about 0.15 mm were used to measure hydrogen release. The longitudinal shaft of the needle measured about 142 mm. The needles were constructed with an end collar designed to push into the cavity in a holder. The collar measured about 15 mm in length and 3 mm in diameter with the end of the collar being 2 mm or less in diameter. The distance to the first hold in the need was about 134 mm and the gap between holes was about 48 mm.

Figure 13:
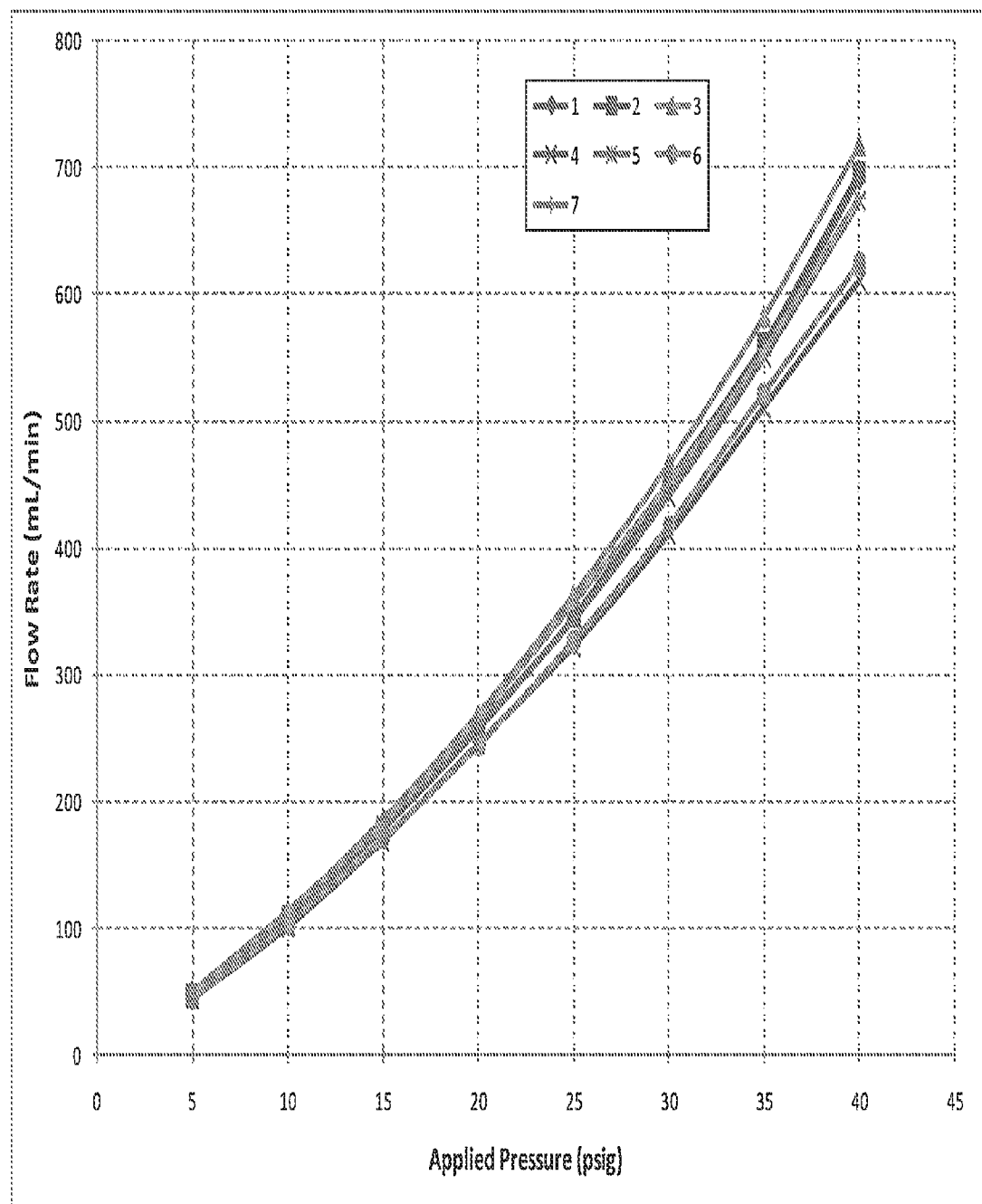
FIG. 13 is a graph showing measured hydrogen gas flow rates for various needle sampling devices at different applied pressures, in accordance with certain examples.

Each needle was mounted in a head space sampling head assembly which was connected to a manual pressure regulator connected to a hydrogen supply. The other ports on the assembly were sealed. The needle mechanism was rotated to extend the needle beyond the assembly baseplate. A silicone plug was pushed over the exposed needle tip, and an electronic flowmeter was connected to the needle through tubing. Hydrogen gas flow rates were measured for each needle at different applied pressures, and the results are shown in Table 2 and plotted graphically in FIG. 13.

TABLE 2

| Applied Pressure (psig) | Needle 1 (mL/min) | Needle 2 (mL/min) | Needle 3 (mL/min) | Needle 4 (mL/min) | Needle 5 (mL/min) | Needle 6 (mL/min) | Needle 7 (mL/min) | Mean (mL/min) | RSD % |
|---|---|---|---|---|---|---|---|---|---|
| 5 | 48.6 | 47.7 | 48.9 | 44.6 | 47.4 | 44.4 | 49.3 | 47.3 | 4.2 |
| 10 | 109 | 109 | 111 | 101 | 108 | 103 | 113 | 107.7 | 4.0 |
| 15 | 180 | 178 | 185 | 169 | 180 | 170 | 183 | 177.9 | 3.5 |
| 20 | 260 | 257 | 268 | 245 | 259 | 244 | 266 | 257.0 | 3.7 |
| 25 | 345 | 345 | 362 | 322 | 343 | 326 | 356 | 342.7 | 4.2 |
| 30 | 449 | 452 | 465 | 410 | 441 | 417 | 451 | 440.7 | 4.5 |
| 35 | 557 | 561 | 582 | 510 | 550 | 522 | 555 | 548.1 | 4.5 |
| 40 | 691 | 696 | 717 | 610 | 673 | 624 | 676 | 669.6 | 5.8 |

These flow rates are slightly greater than expected (~650 mL/min instead of ~550 mL/min) but are still of the right order. It would be expected that about 19 mL of hydrogen would be released from each analysis cycle. It is very difficult to control these flow rates because of the 4th-order dependency on the internal diameter. What is extremely impressive is how reproducible these flow rates are between the seven different needles—the relative standard deviation for all the flow rates is only 4 to 5%.

Figure 14:
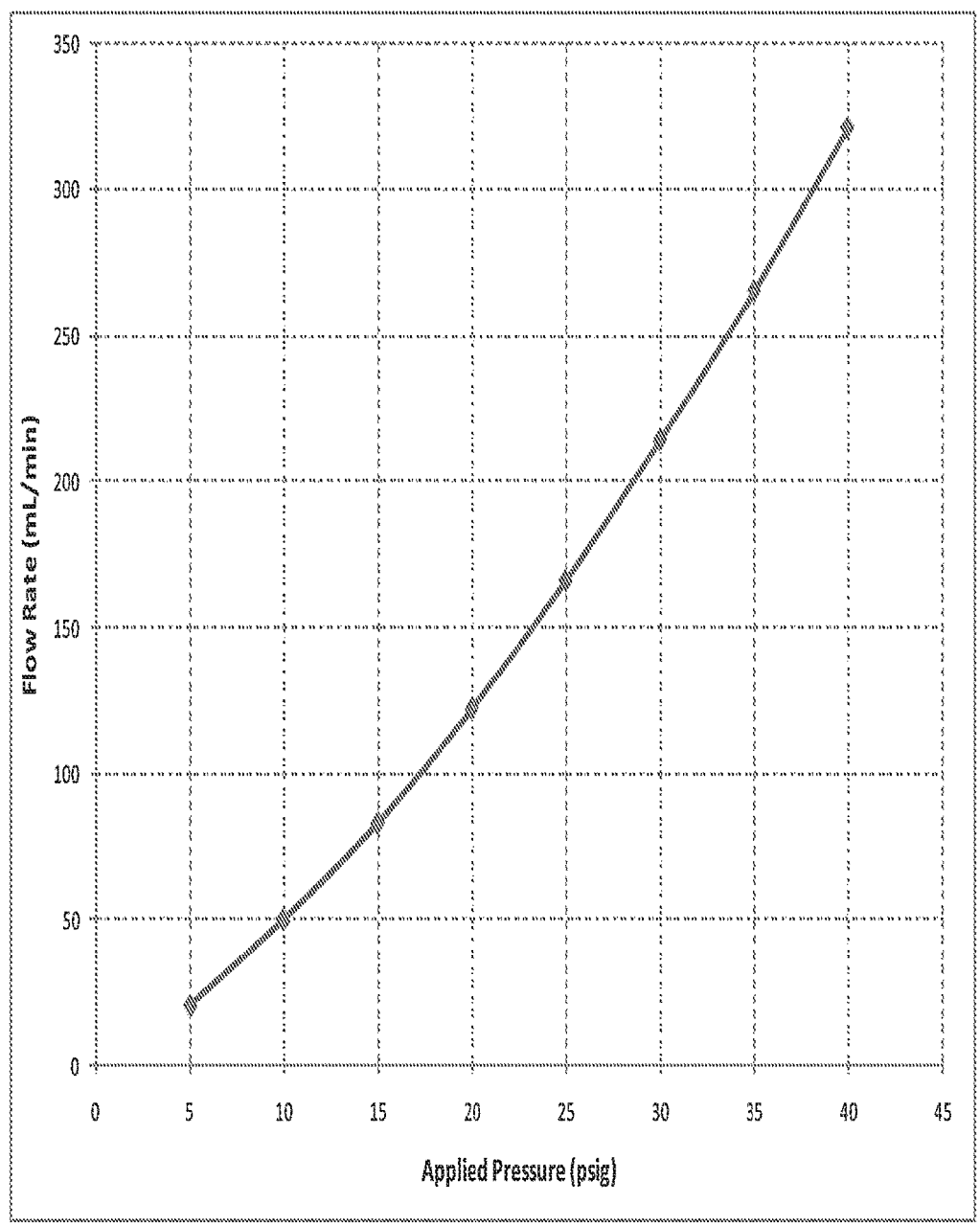
FIG. 14 is a graph showing measured helium flow rates with applied pressure, in accordance with certain examples.

Needle #5 was chosen for the further tests as its flow characteristics were closest to the mean of the seven needles tested. For reference, Needle #5 was tested with helium, and the results are shown in Table 3 and in FIG. 14.

TABLE 3

| Applied Pressure (psig) | Needle 5 (mL/min) |
|---|---|
| 5 | 20.3 |
| 10 | 50 |
| 15 | 83 |
| 20 | 122 |
| 25 | 166 |
| 30 | 214 |
| 35 | 265 |
| 40 | 321 |

The flow rates with helium using the needles of this example are much slower (about half) than those for hydrogen.

The needles tested in this example delivered hydrogen about 8x less than a standard needle as used in Examples 1-3. With a total needle venting time of about 1.7 seconds (see Table 1), only about 19 mL of hydrogen gas would be released with the needles of this example compared to 125 mL or more with the standard needle.

Example 5

The more restrictive needles of Example 1 can also affect the flow rate of carrier gas into sample vials during the pressurization step prior to sampling. The pressurization times will be longer and may need a change to the pressurization set in the head space method.

Figure 15:
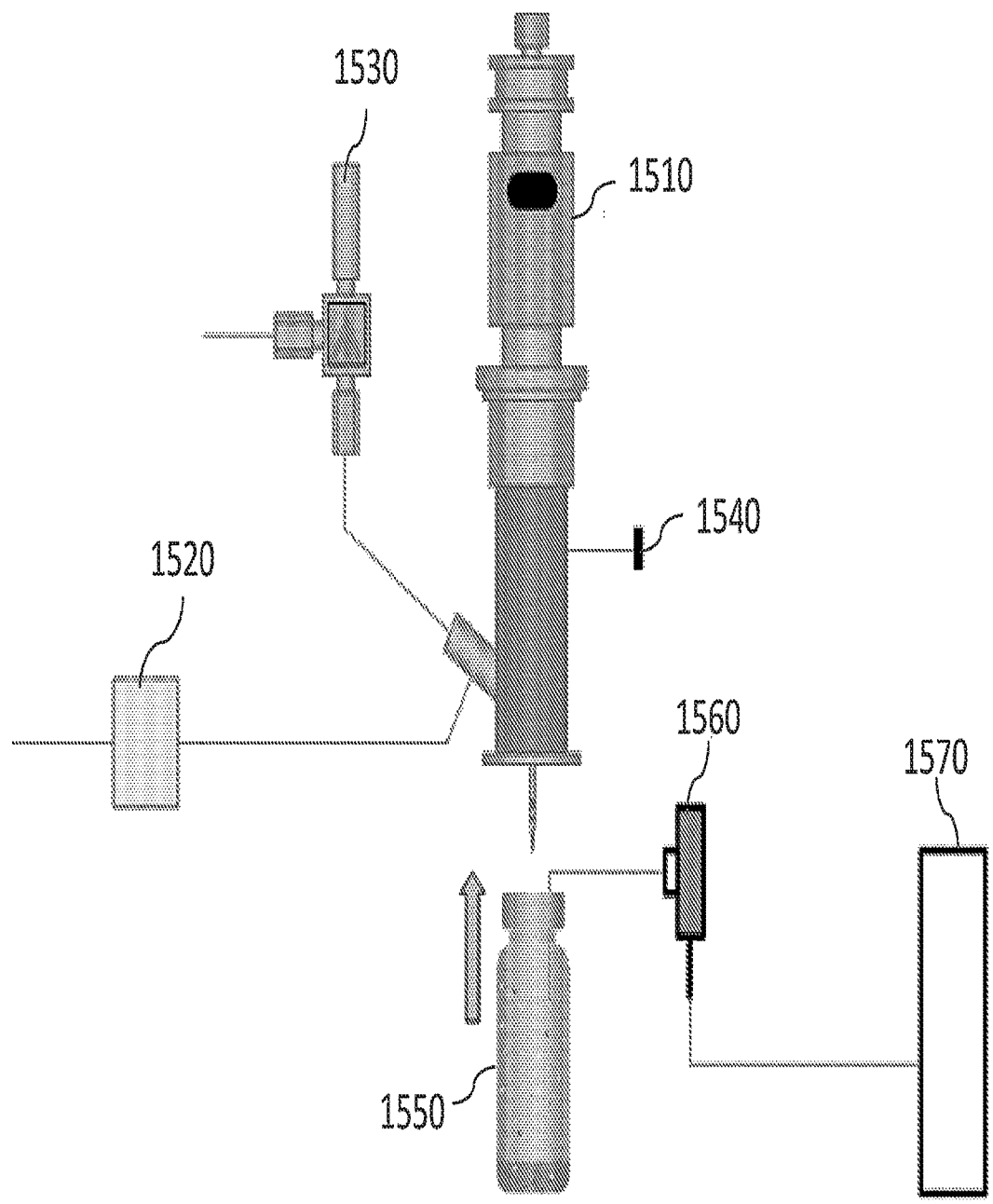
FIG. 15 is a schematic of a system used to test various flow control devices, in accordance with certain examples.

A system was assembled as shown in FIG. 15. A spare sampling head 1510 was mounted on a clamp-stand (i.e. no headspace instrument was involved). A manual pressure regulator 1520 was connected to the gas input line. A needle valve 1530 was connected to the output (column/transfer line) port. The vent line was capped with a plug 1540. A short narrow length of stainless steel tubing was pushed through the seal of the sample vial 1550. The other end of this tube was connected to a Freescale MPX1000 0-100 psig pressure sensor 1560. The analog output of the sensor was fed into a TotalChrom NCI interface 1570 for data collection at 25 Hz.

To record the vial pressurization profile, the following method was used: (1) The needle was withdrawn into the sampling head to seal it; (2) The manual pressure regulator was adjusted to the pressure required for the test; (3) The needle valve was adjusted to vent 15±2 mL/min of the carrier gas; (4) the needle was extended from the bottom of the sampling head by about 2 cm to expose the lower orifice; (5) TotalChrom was set up to collect data from the NCI box and a run was initiated; and (6) After about 0.5 minutes, the vial was pushed onto the exposed needle and the change in pressure inside the vial was recorded over a 3-minute period. A cloth was used to handle the vial at this point because heat from a hand changed the internal vial pressure. These tests were conducted at ambient temperature (~23° C.). The gas viscosity will increase with temperature and so these timings would increase.

Figure 16:
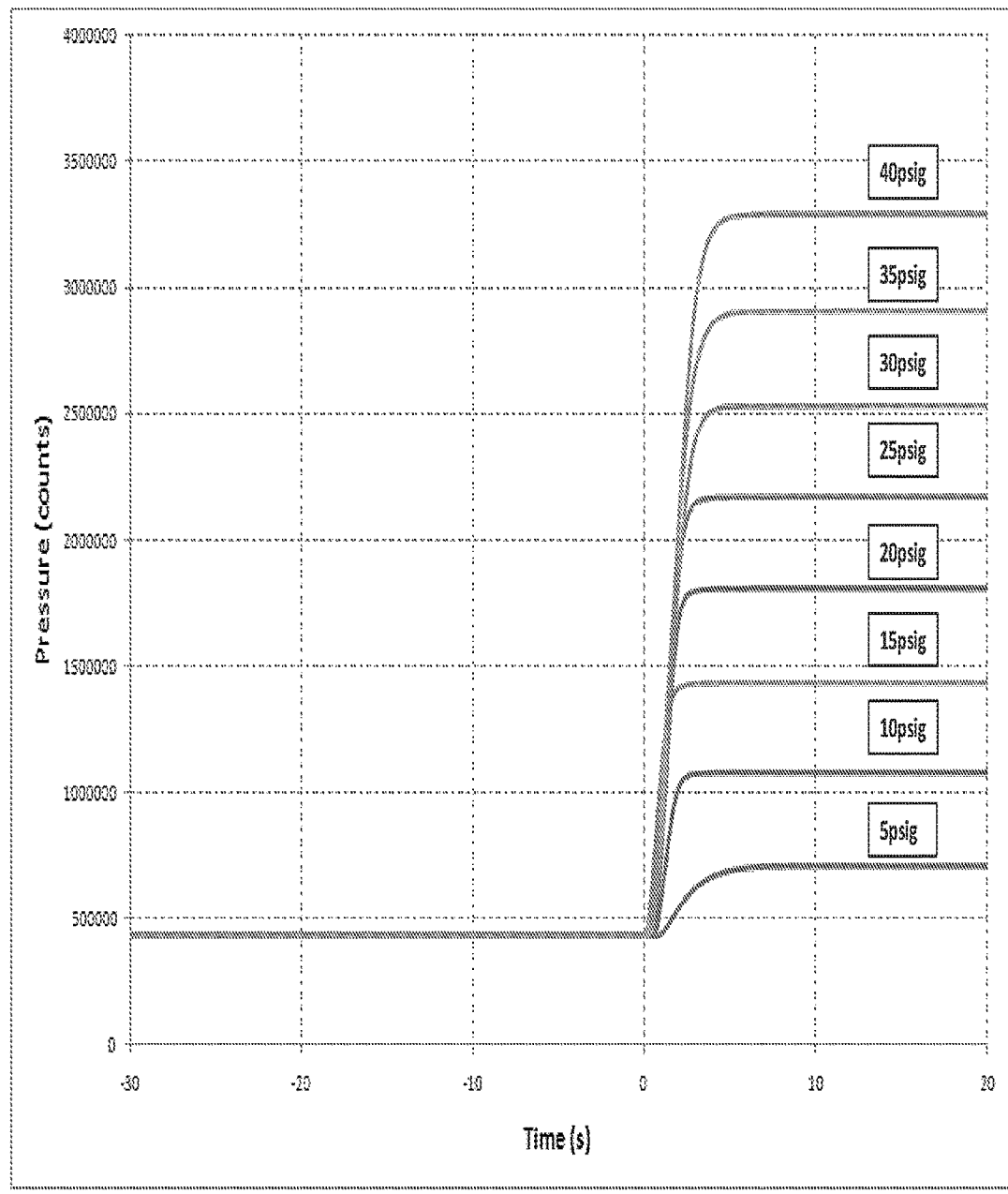
FIG. 16 is graph showing pressure versus time for a standard headspace needle and using helium as a carrier gas, in accordance with certain examples.
Figure 17:
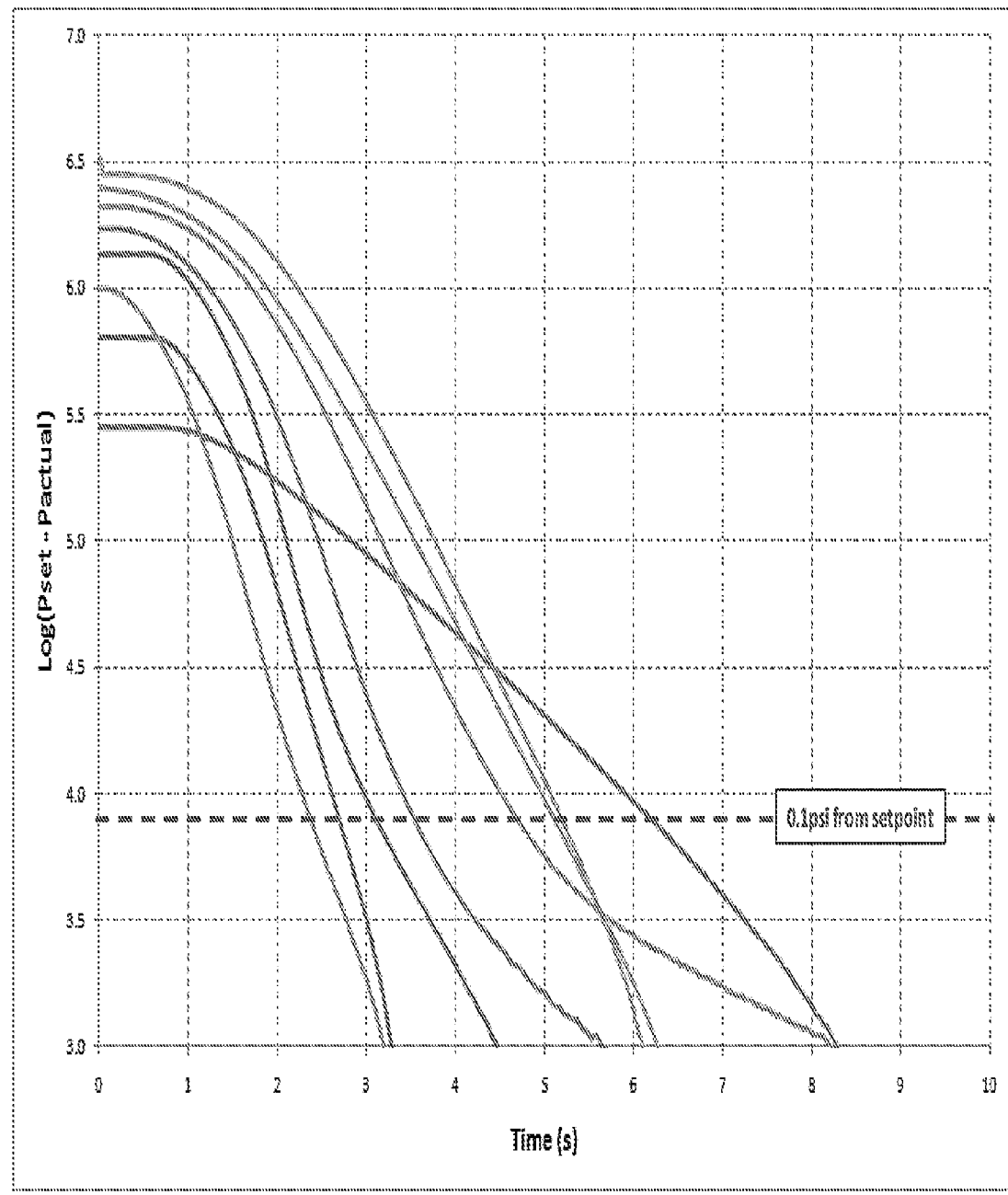
FIG. 17 is a semi-log plot of the data from FIG. 16, in accordance with certain examples.

To benchmark the pressurization tests, a standard HS needle was tested with helium has as shown in FIG. 16. To better establish the pressurization times, log(set-pressure-actual-pressure) was plotted against elapsed time as shown in FIG. 17. If the pressurization profile matched theory, these plots would be linear. Using this sensor, the pressure would be within 0.1 psi of the set pressure once the value of log(set-pressure-actual-pressure) had decayed to a value of 3.85 as indicated by the dashed line in FIG. 17. Thus for helium with the standard needle, the pressurization takes a maximum of around 5 seconds.

Figure 18:
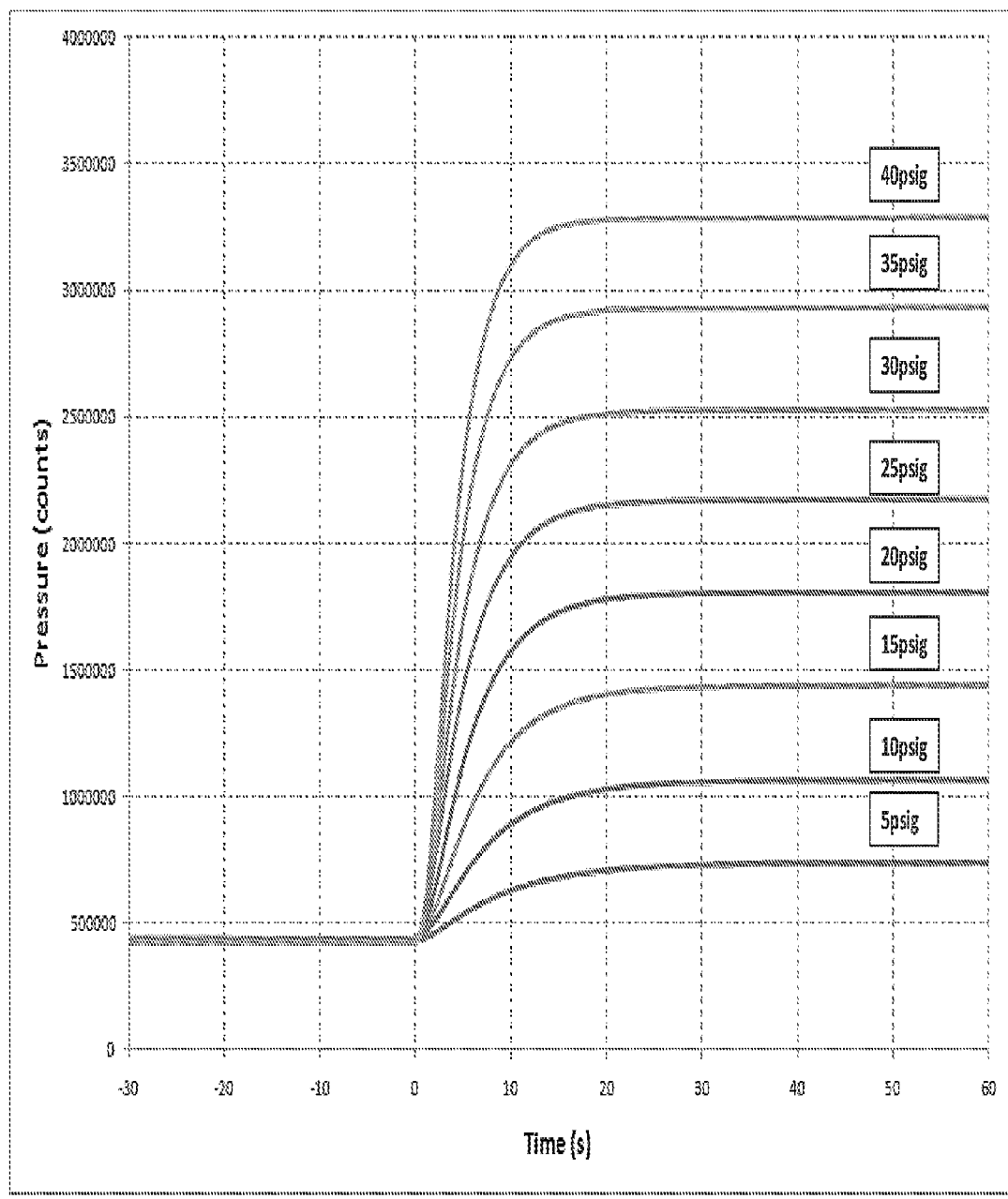
FIG. 18 is graph showing pressure versus time for a new sampling device and using hydrogen as a carrier gas, in accordance with certain examples.
Figure 19:
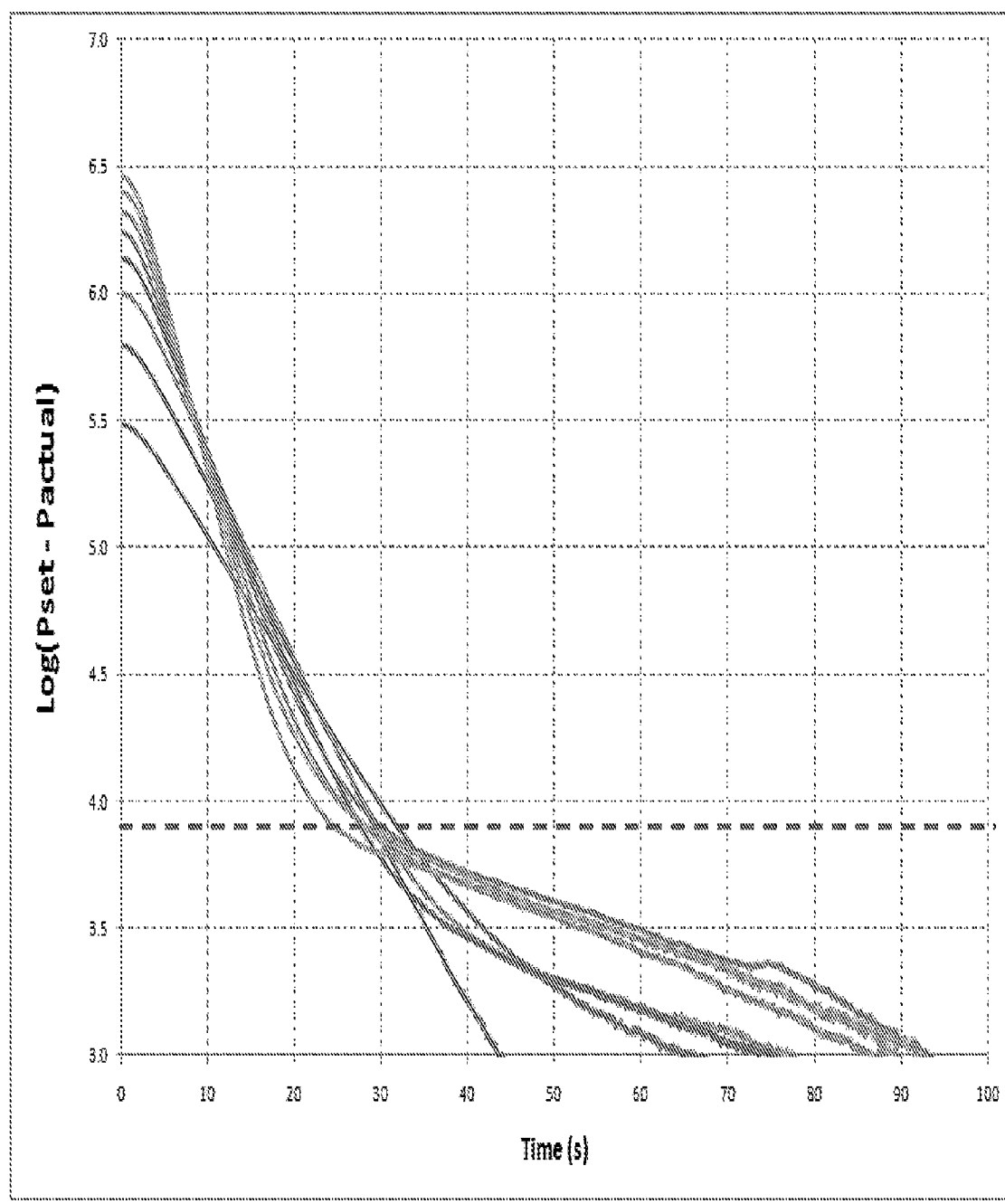
FIG. 19 is a semi-log plot of the data from FIG. 18, in accordance with certain examples.
Figure 20A:
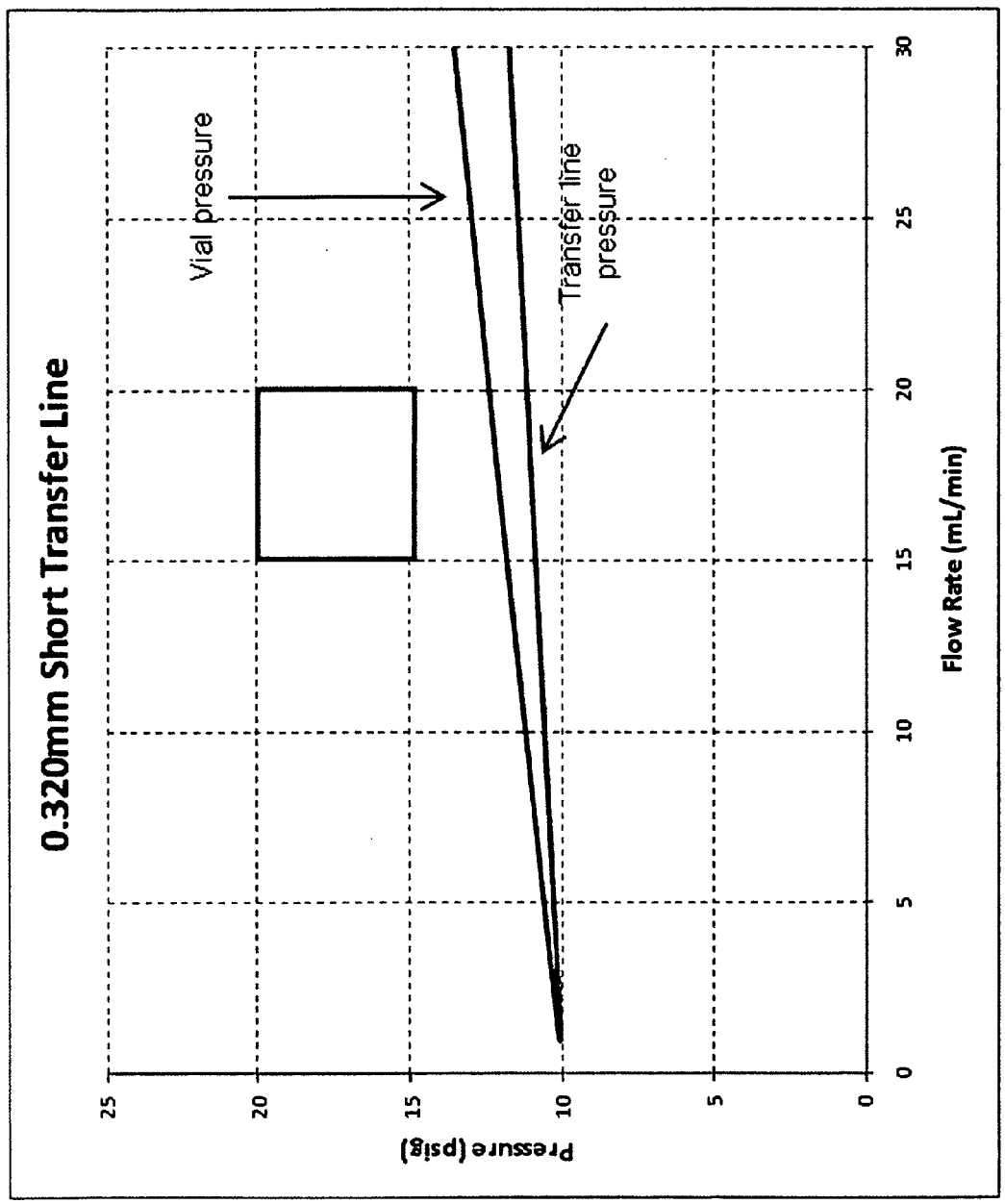
FIGS. 20A-23B show flow versus applied pressures for four transfer line internal diameters and using short length transfer lines (101 mm) and long length transfer lines (166 mm), in accordance with certain examples.
Figure 20B:
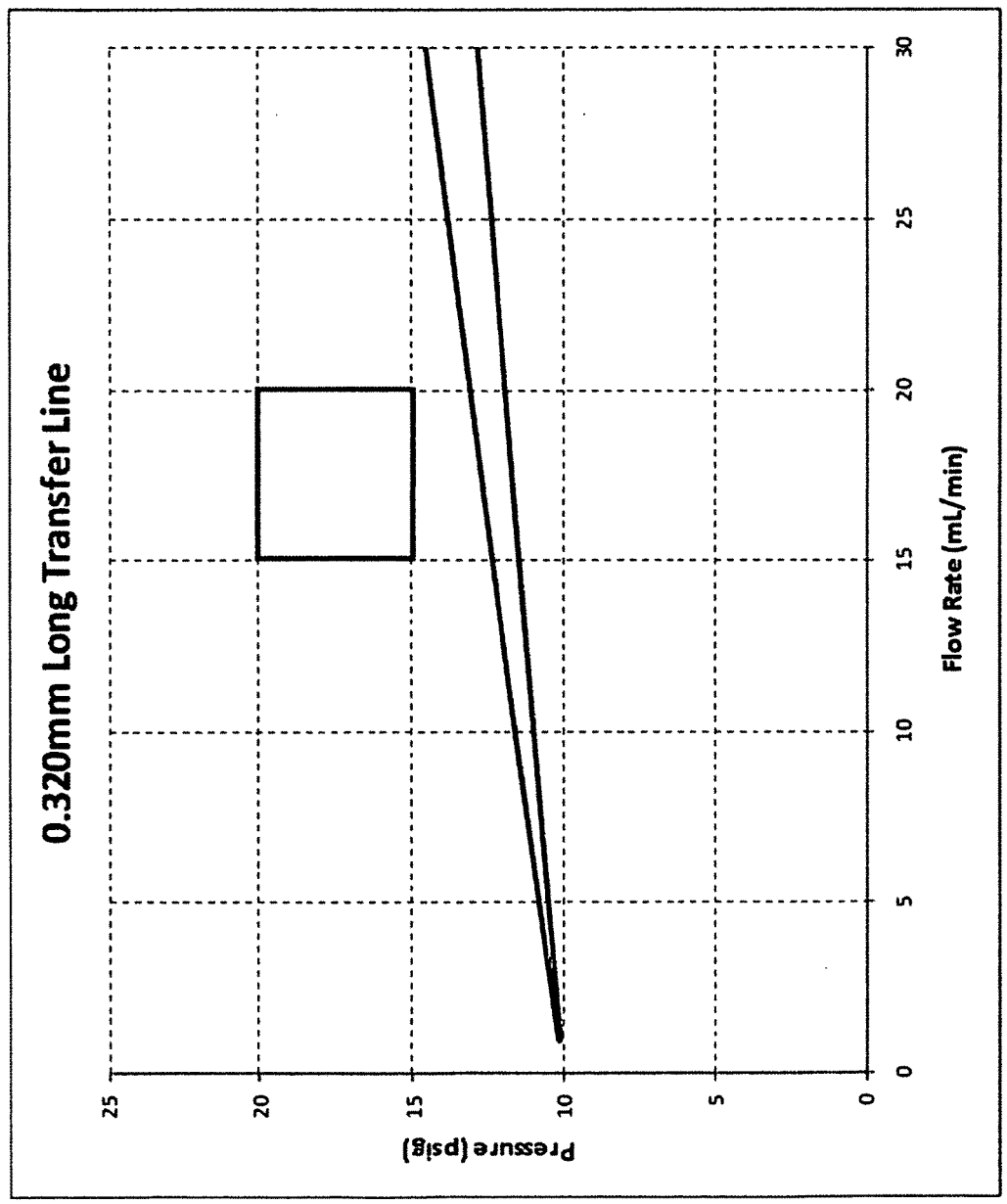
Figure 21A:
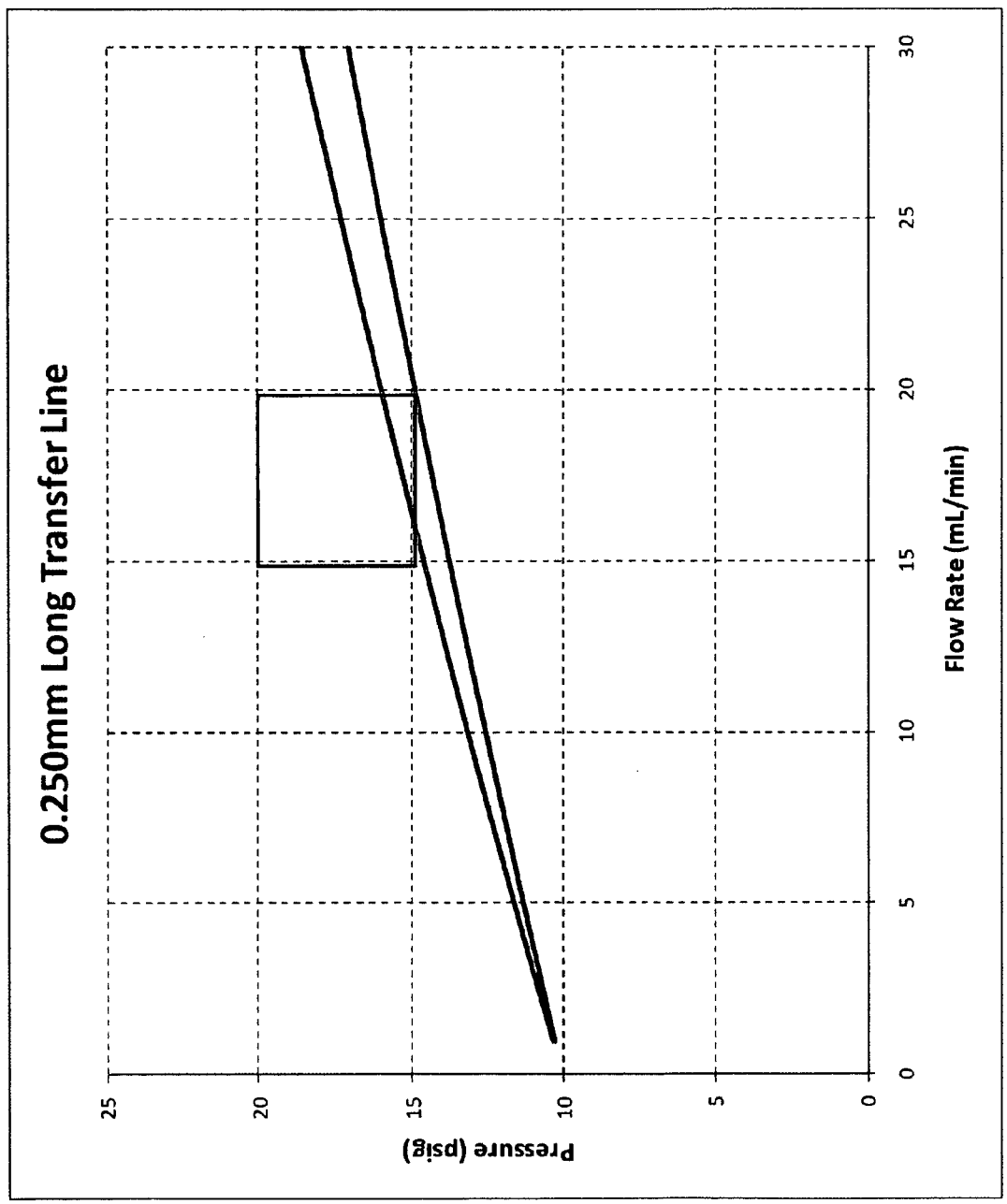
Figure 21B:
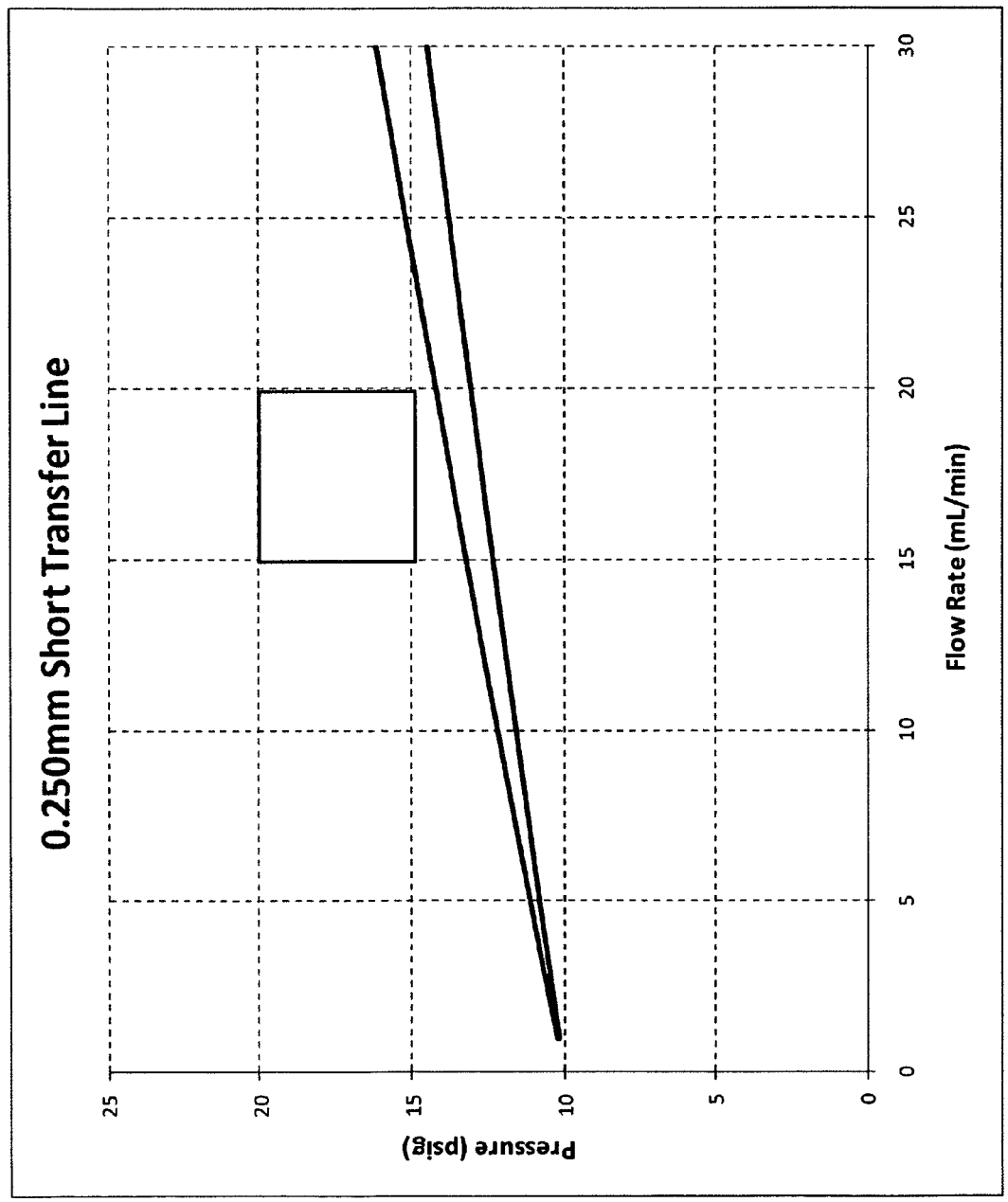
Figure 22A:
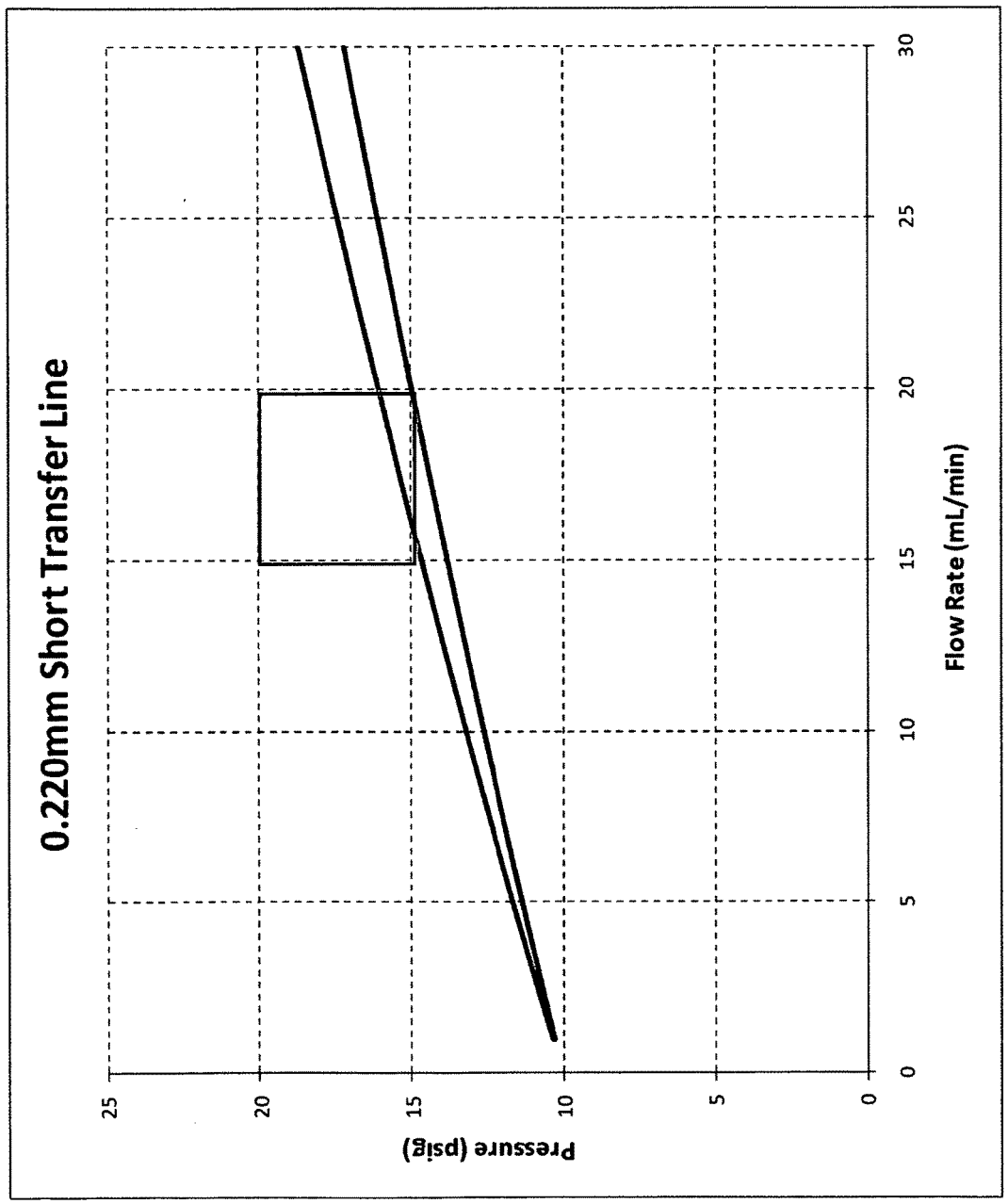
Figure 22B:
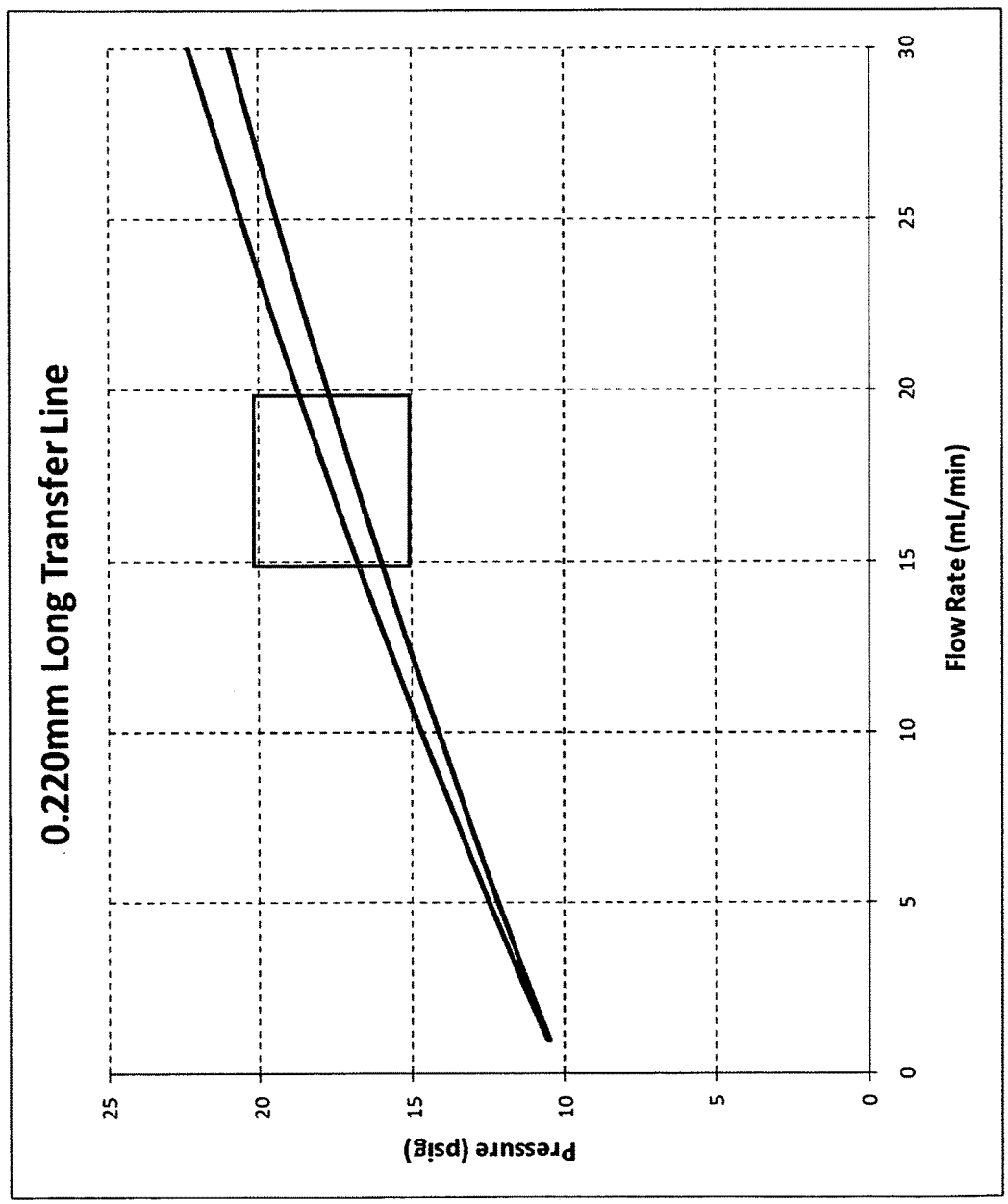
Figure 23A:
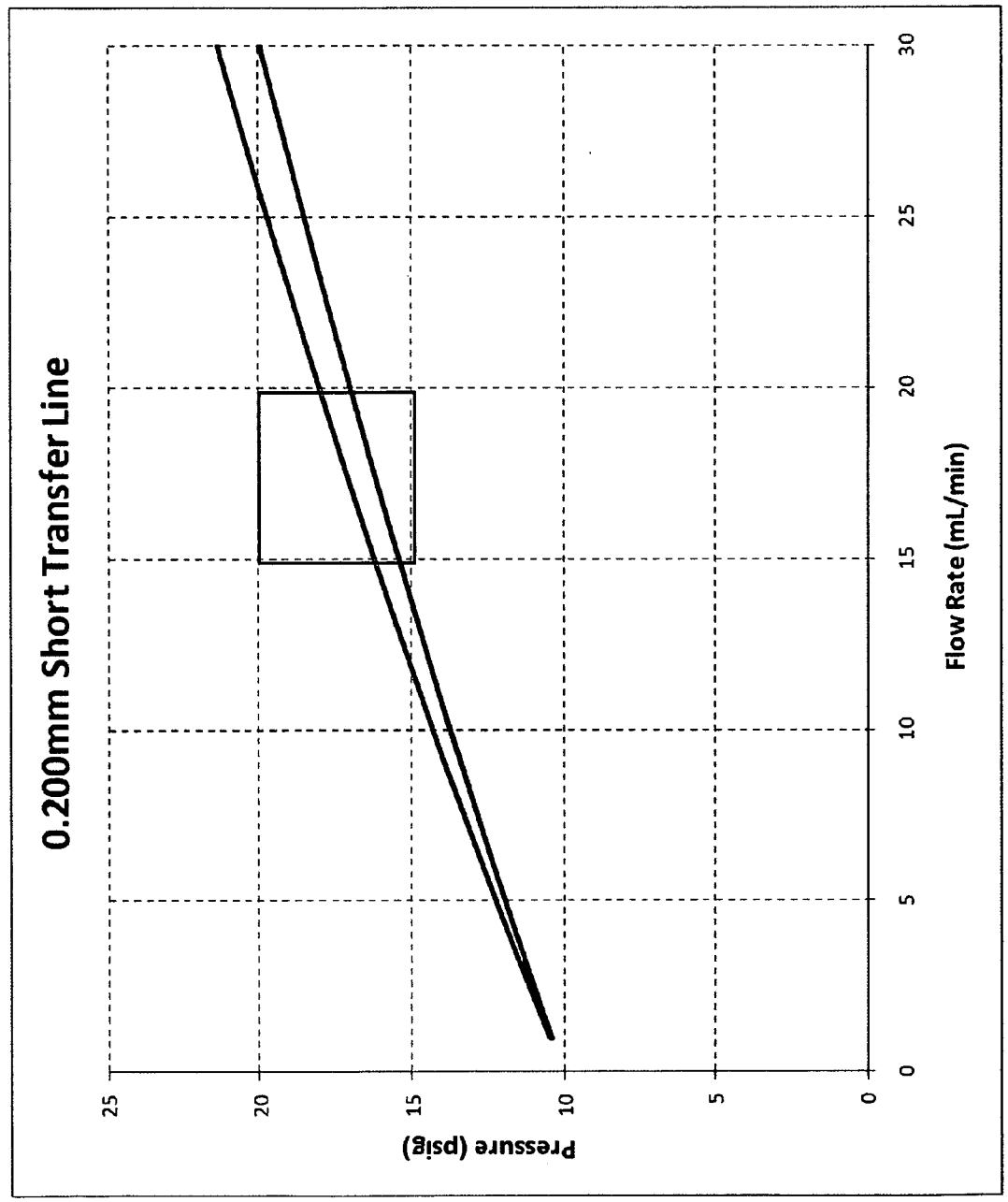
Figure 23B:
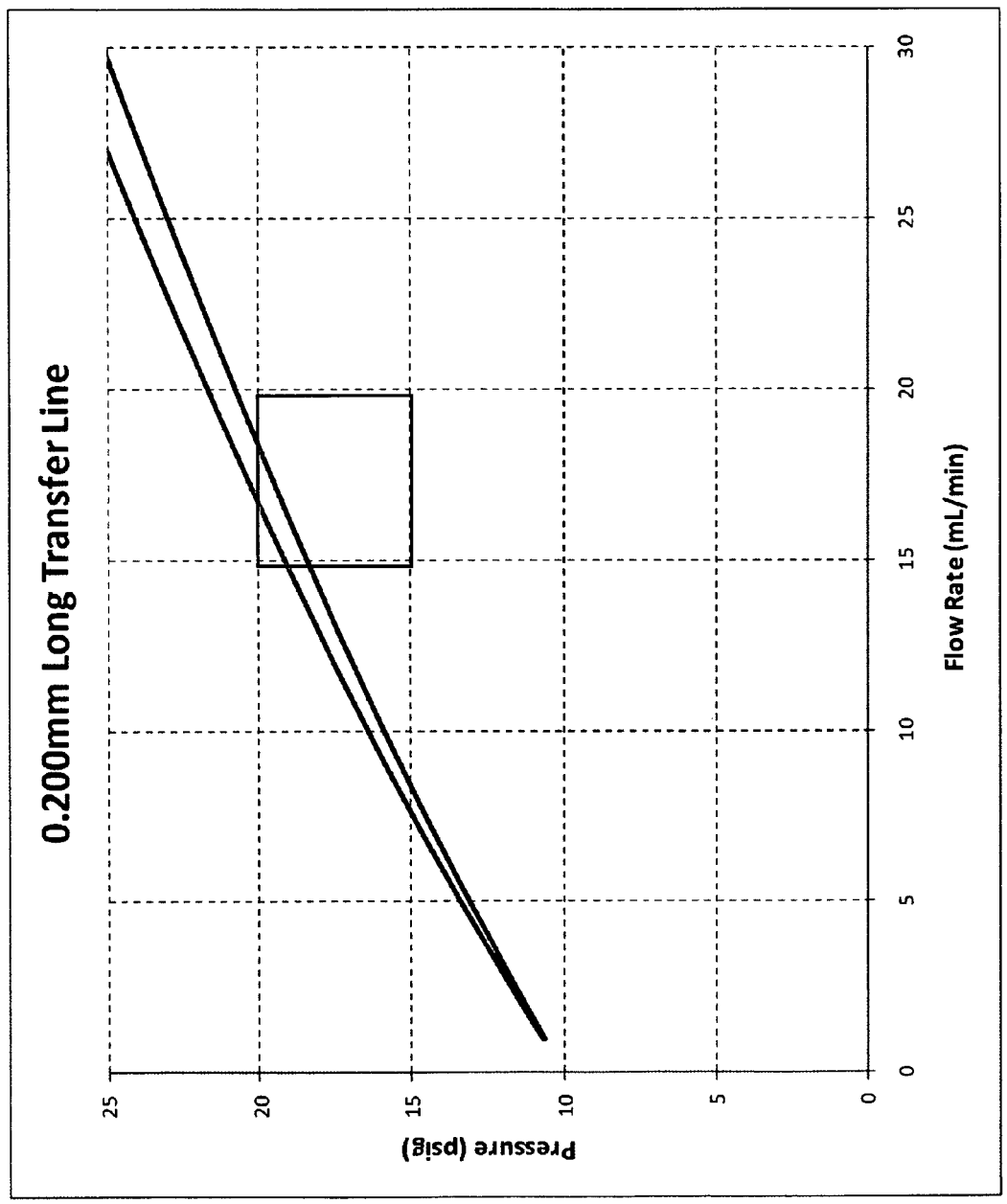

The newer needle as described in Example 4 was tested with hydrogen and the setup shown in FIG. 15. The results are shown in FIGS. 18 and 19 (log plot). The new needle appeared to pressurize empty vials (i.e. worst case) within about 30 seconds at all applied pressures. Most methods have a pressurization time of 1 to 2 minutes and so, although using the newer needle is slower than with the current needle (even with helium), 30 seconds is acceptable. With the new needle, all the pressurization curves are truly asymptotic—there is no overshoot of the pressure inside the vial. This means that during the pressurization process, the pressure inside the vial will never exceed the pressure upstream of the needle. This should make the system highly immune from pre-injection effects that are reported time to time by users of these systems—especially with PPC regulators.

Example 6

Another aspect of the new needle that was evaluated was its effect on the flow rate of headspace vapor out of the sample vial and down a transfer line at 15 to 20 mL/min during the injection process. If the new needles impede the flow of this vapor, then this result will have a very direct effect on the amount of vapor entering the GC column and the analytical precision of the analysis. It is difficult to check this flow rate experimentally as the outlet of the transfer line will be inside an injector at elevated temperature and pressure and the sampling time will be very short—just a few seconds. It is possible, however, to model the flow behavior of vapor from a pressurized vial, through a restrictive needle and then through a transfer line. The temperatures and pressures along the flow path would be known. The predictive model used is that developed for the thermal desorption flow control algorithm (U.S. Pat. No. 7,219,532B2, the entire disclosure of which is hereby incorporated herein by reference). This model is represented by Equation 1.

$$F_o = \frac{\pi \cdot T_o}{256 \cdot p_o} \cdot \frac{(p_i^2 - p_0^2)}{\left(\frac{T_t + \eta_t \cdot L_t}{d_t^4}\right) + \left(\frac{T_n \cdot \eta_n \cdot L_n}{d_n^4}\right)} \quad \text{Eqn 1}$$

In equation 1, $F_o$ is the flow rate at the transfer line outlet, $d_n$ is the needle internal channel diameter, $d_t$ is the transfer line internal diameter, $L_n$ is the length of the needle internal channel, $L_t$ is the length of the transfer line, $\eta_n$ is the viscosity of the headspace vapor within the needle, $\eta_t$ is the viscosity of the headspace vapor within the transfer line, $T_n$ is the absolute temperature of the needle, $T_t$ is the absolute temperature of the transfer line, $T_o$ is the absolute temperature of the transfer line outlet inside the injector, $p_i$ is the absolute pressure of the headspace vapor in the sample vial, and $p_o$ is the absolute pressure at the outlet of the transfer line inside the injector.

Using Equation 1 it is possible to predict the effect of the needle bore on the flow rate of headspace vapor into the GC injector. The intent is to deliver a flow rate of carrier gas of between 15 and 20 mL/min with a pressure drop between the vial and GC injector/column inlet of 5 to 10 psi. The first consideration is the diameter of the transfer line tubing. With the newer needles, e.g., those of Example 4, a wider-bore transfer line will produce a bigger pressure drop across the needle and so the needle may become the primary flow limiting factor.

Equation 1 was applied to a range of common transfer line geometries for both short and long lengths (101 mm and 166 mm respectively) and plots were produced showing flow rates of hydrogen for applied pressures. The standard conditions used in these calculations are given in Table 4.

TABLE 4

| Setting | Value |
| --- | --- |
| Transfer line temperature, ° C. | 60 |
| Needle temperature, ° C. | 80 |
| Injector/column pressure, psig | 10 |

FIGS. 20A-23B show flow versus applied pressures for four transfer line internal diameters. The target range for flows and pressures are indicated by the boxes on each graph. The top line in each figure represents the vial pressure and the bottom line in each figure represents the transfer line pressure.

The 0.320 mm i.d. transfer line was not suited for use with hydrogen and the new needle. The pressures will be too low or the flow rates too high for correct operation. The pressure drop across the needle (difference between vial pressure and pressure at transfer line inlet) is high which will also impact performance. The profiles for the 0.250 mm i.d. transfer line tubing are better than the ones for the 0.320 mm i.d. transfer line. The profiles for the 0.220 mm i.d. transfer line tubing look very suitable—they cross the target ranges nicely. Similarly, the profiles for the 0.200 mm i.d. transfer line tubing are acceptable.

Figure 24A:
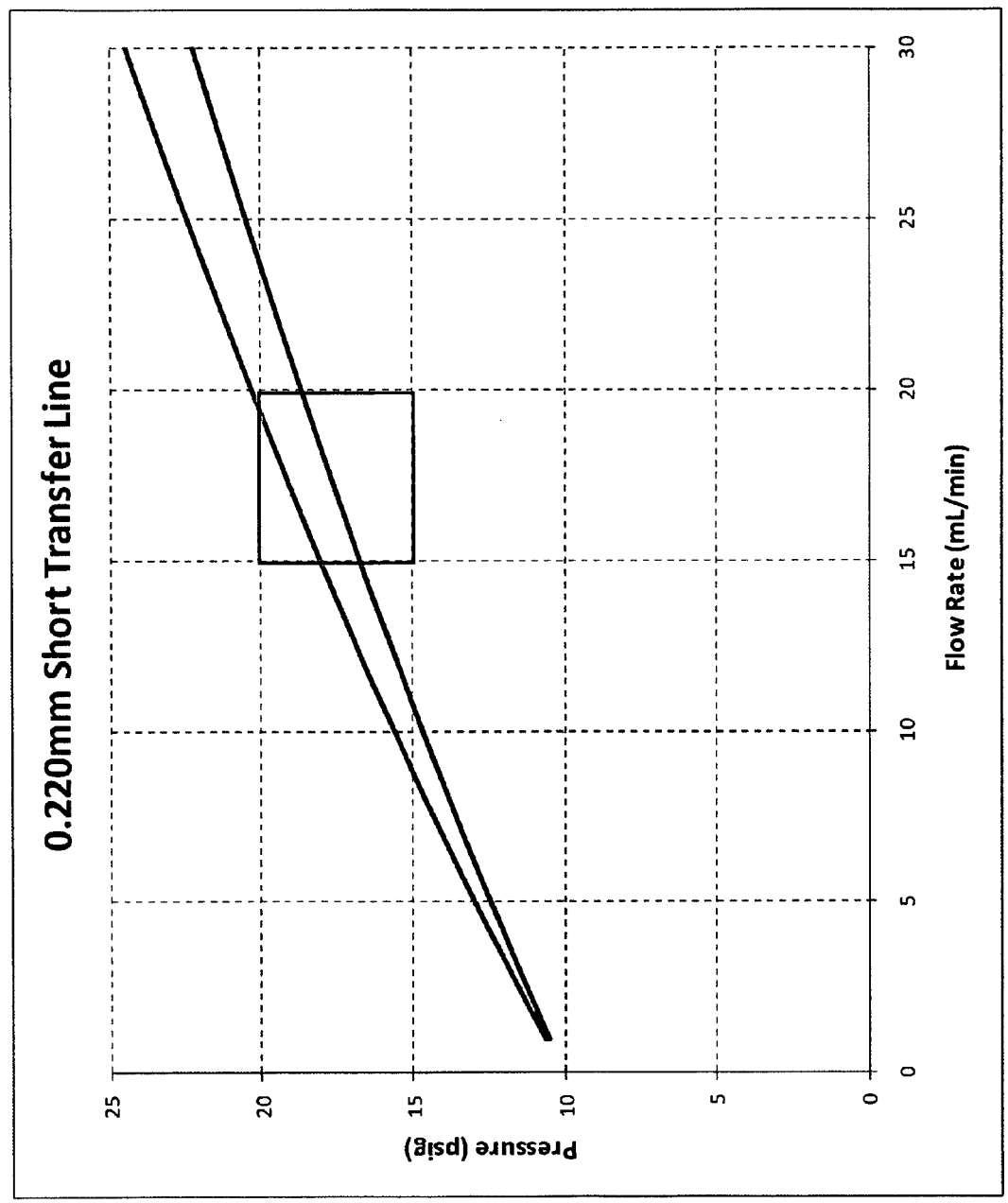
FIGS. 24A-26B are graphs of hydrogen flow rates for the 0.220 mm i.d. transfer line tubing at different injector/column pressures and different temperatures, in accordance with certain examples.
Figure 24B:
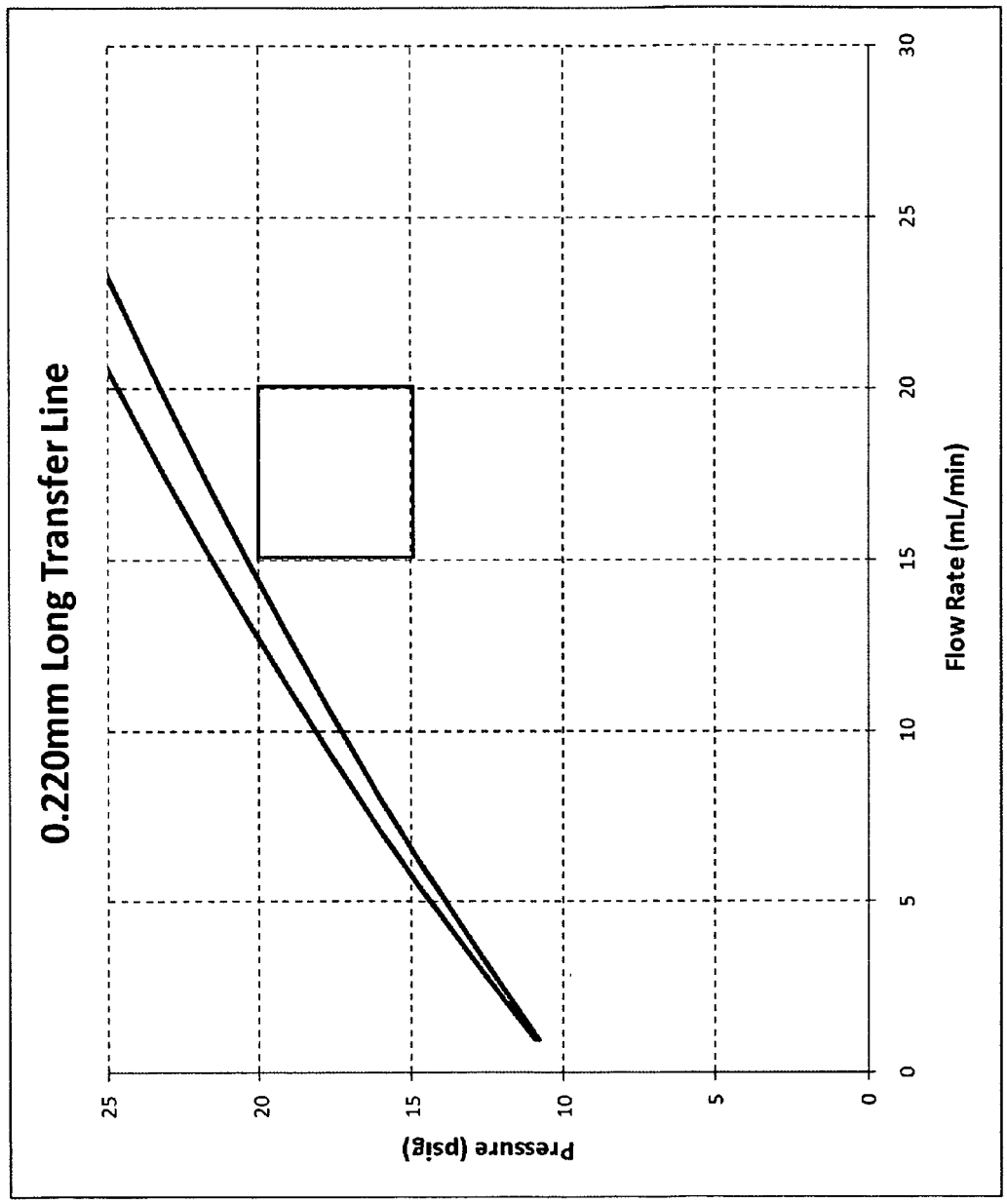
Figure 25A:
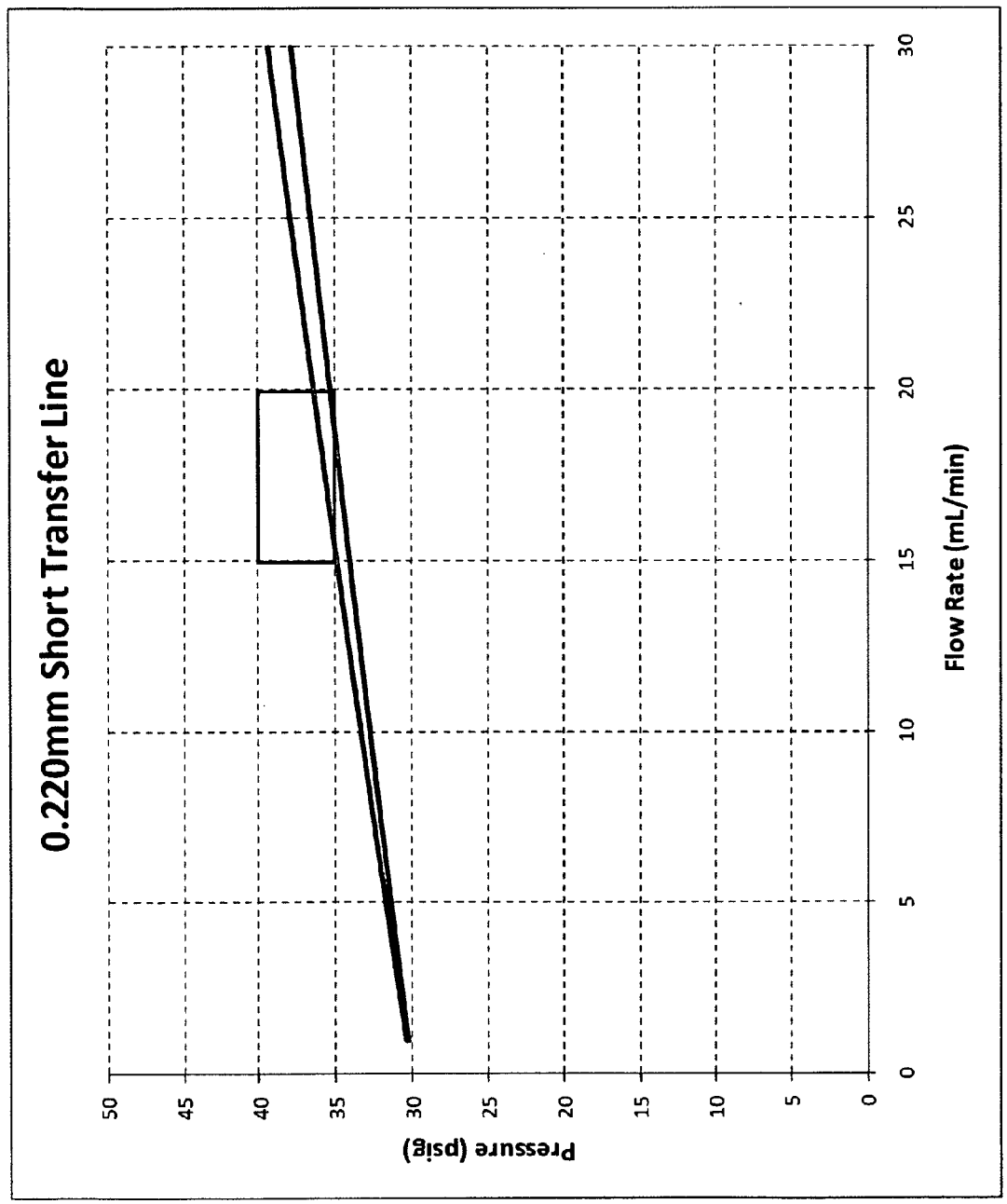
Figure 25B:
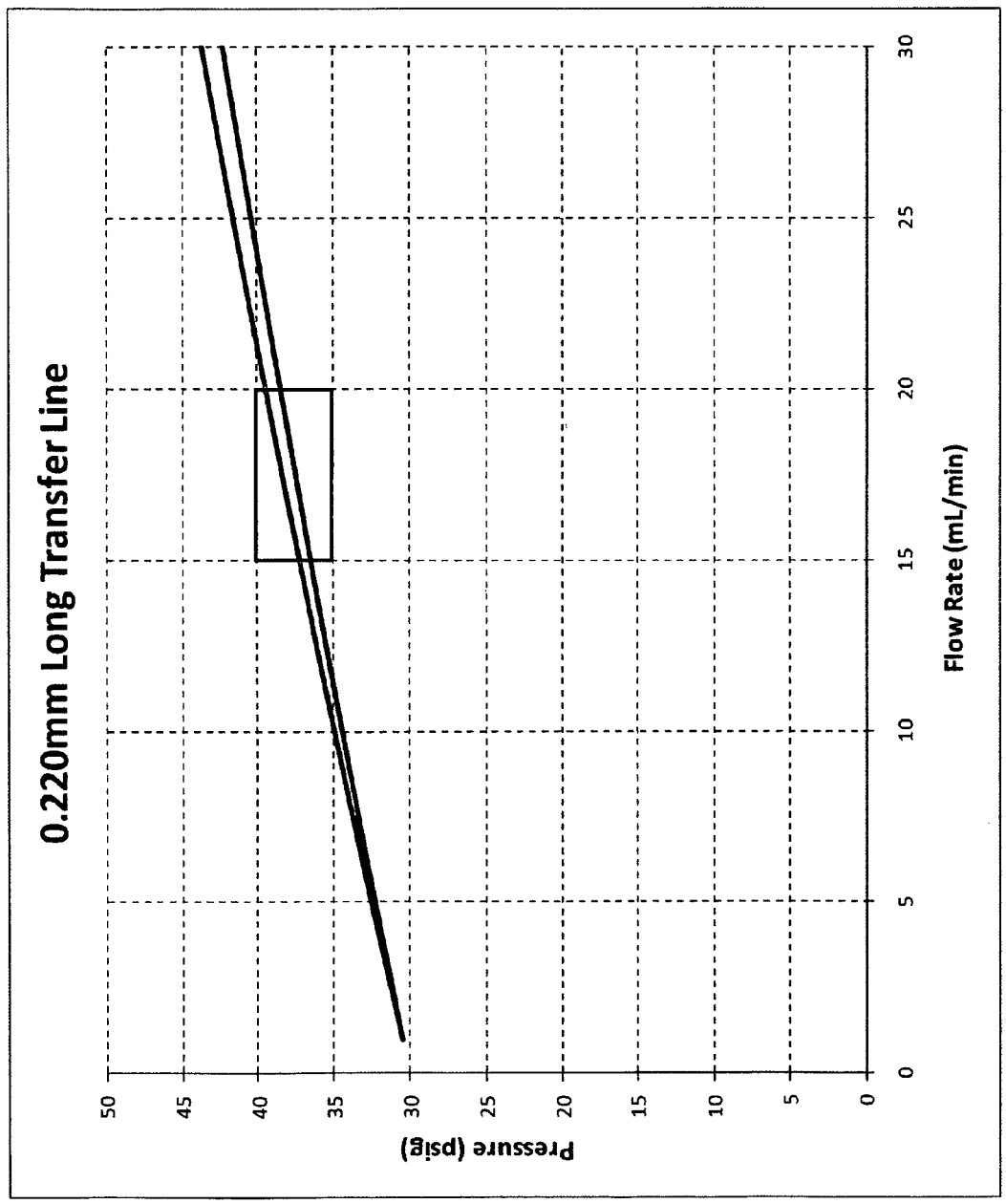
Figure 26A:
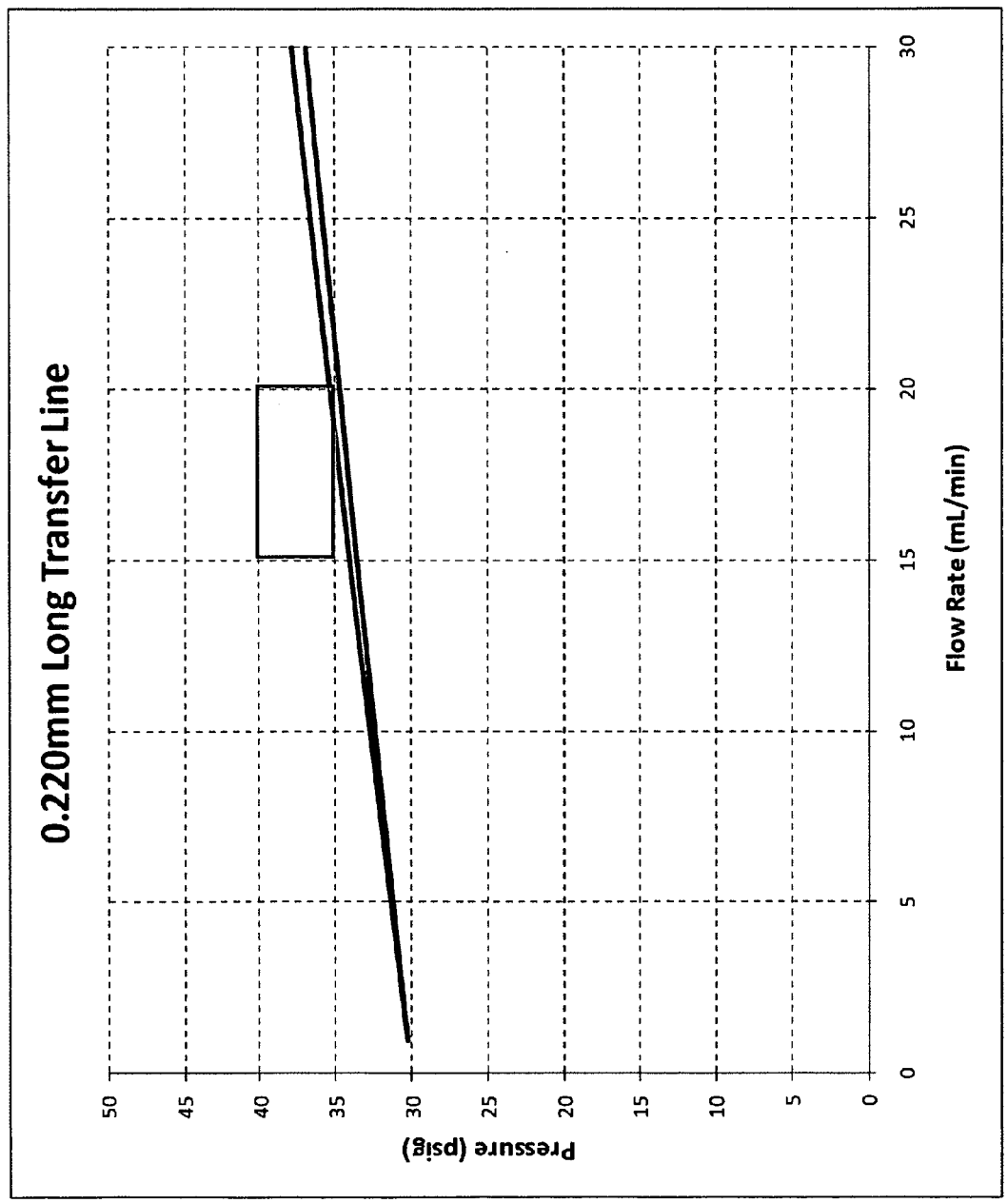
Figure 26B:
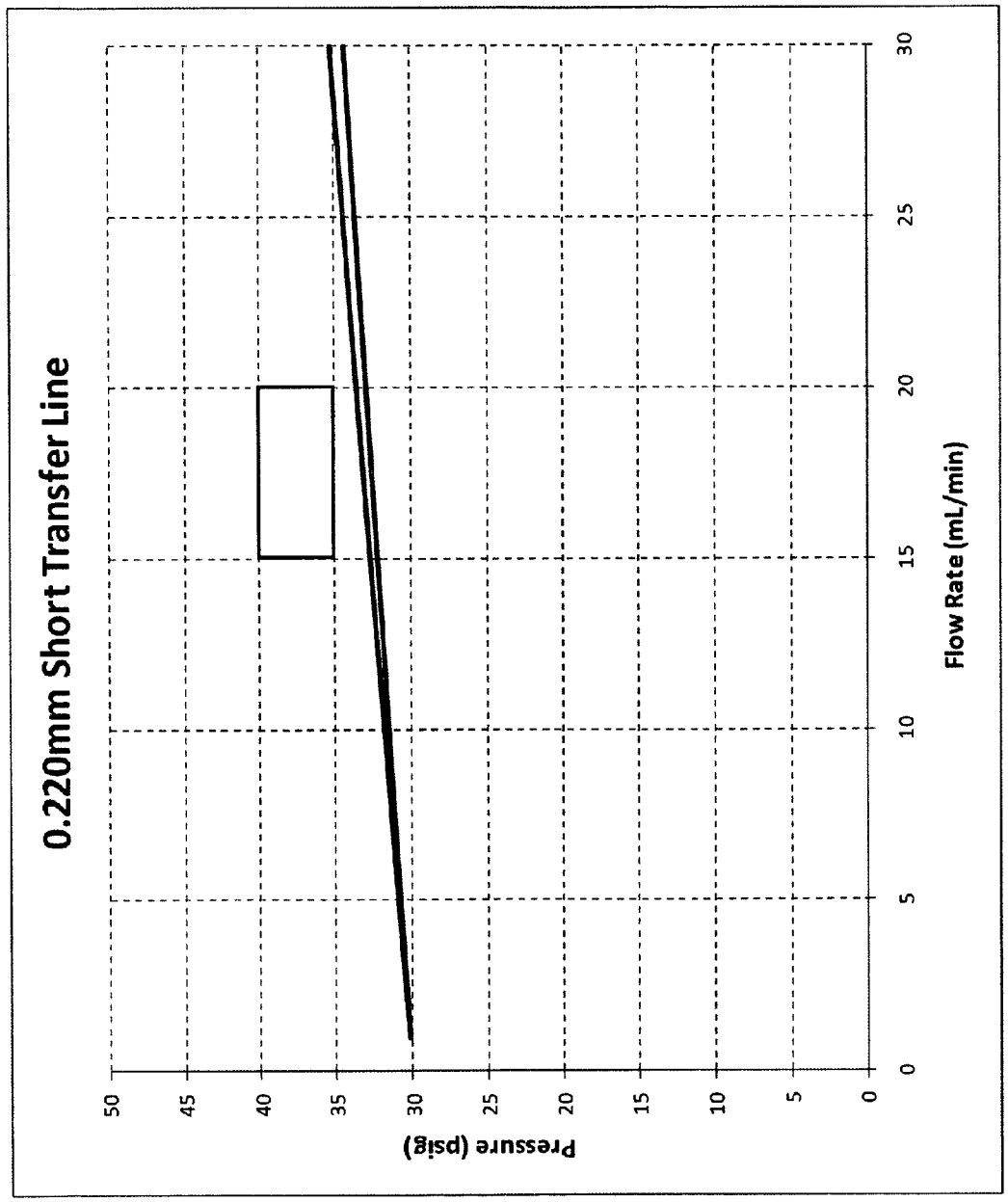
Figure 27:
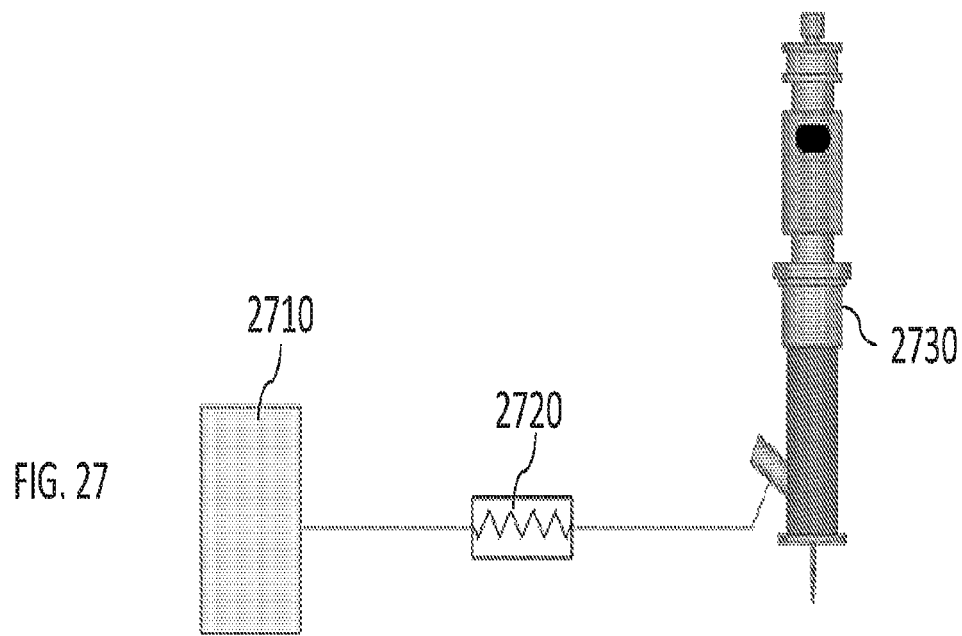
FIG. 27 is a schematic of a system including a restrictor between the carrier gas and the sample head, in accordance with certain examples.

Additional graphs of hydrogen flow rates for the 0.220 mm i.d. transfer line tubing were produced for different injector/column pressures and different temperatures as shown in FIGS. 24A-26B. In FIGS. 24A and 24B, the injector/column pressure used was 30 psig and the vial and needle temperatures were both 210° C. In FIGS. 25A and 25B, the injector/column pressure used was 10 psig and the vial and needle temperatures were both 210° C. In FIGS. 26A and 26B, the injector/column pressure used was 30 psig and the vial and needle temperatures were 60° C. and 80° C. respectively. These plots shows that for most chromatographic situations, the 0.220 mm i.d. transfer line tubing would provide acceptable performance. The pressure drop across the needle with the 0.220 mm i.d tubing seems to represent only 4 to 6% of the total pressure drop between the vial and the column inlet, which is indicative of acceptable performance.

Example 7

While Examples 5-6 use a modified needle, other configurations can be provided that permit the use of an explosive carrier gas with a standard needle. One such configuration is shown in 27 where a system has been modified to include a flow limiter 2720 between a PPC manifold 2710 and a sampling head 2730. The sampling head has a purge line that is used to keep it clean when not actively sampling. It should have a nominal flow rate of 15 mL/min with helium. The flow rate of the vent varied with pressure as shown in Table 5.

TABLE 5

| Pressure (psig) | He (mL/min) | H$_2$ (mL/min) |
|---|---|---|
| 5 | 17.0 | 34.6 |
| 10 | 16.5 | 33.7 |
| 15 | 16.3 | 33.2 |
| 20 | 16.1 | 32.7 |
| 25 | 15.8 | 32.2 |
| 30 | 15.5 | 31.7 |
| 35 | 15.2 | 31.0 |
| 40 | 15.0 | 30.7 |
| 45 | 14.8 | 30.7 |

As shown in Table 5, when the flow valve is adjusted to deliver 15 mL/min of helium, this flow rate doubles when hydrogen is connected. It is important to take this flow rate into account when performing dynamic pressure measurements.

Figure 28:
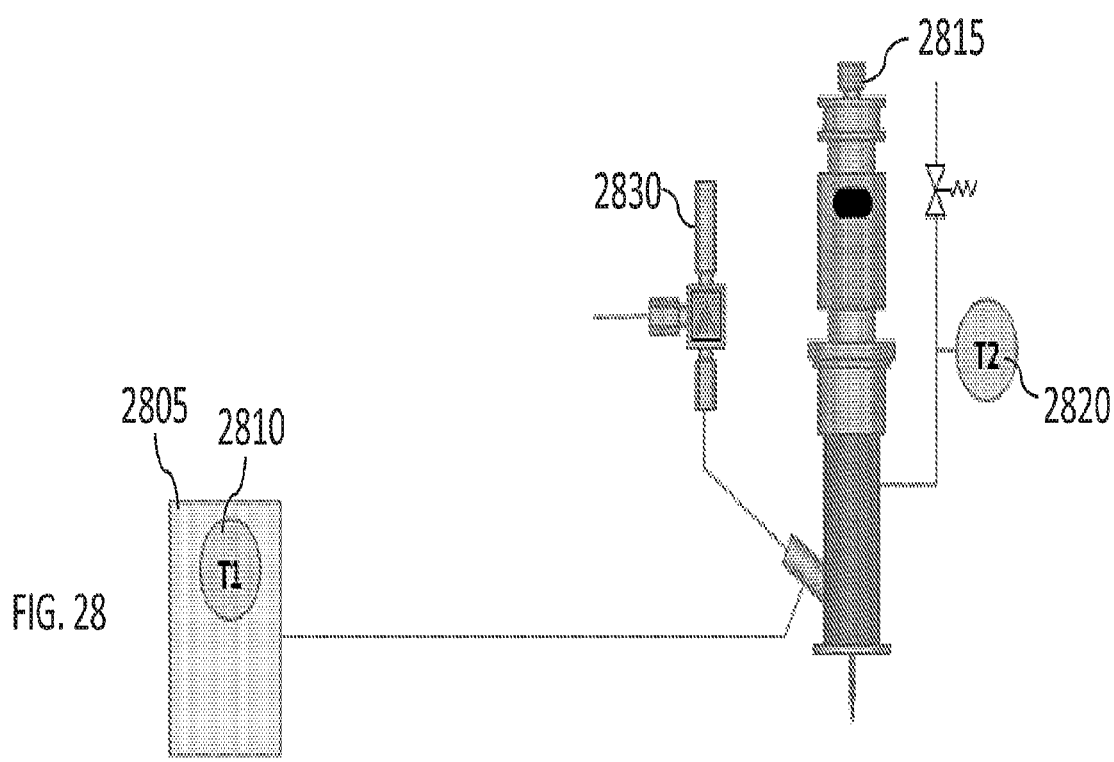
FIG. 28 is a schematic of a test setup including pressure sensors that were to measure pressures at various points in the system, in accordance with certain examples.
Figure 29:
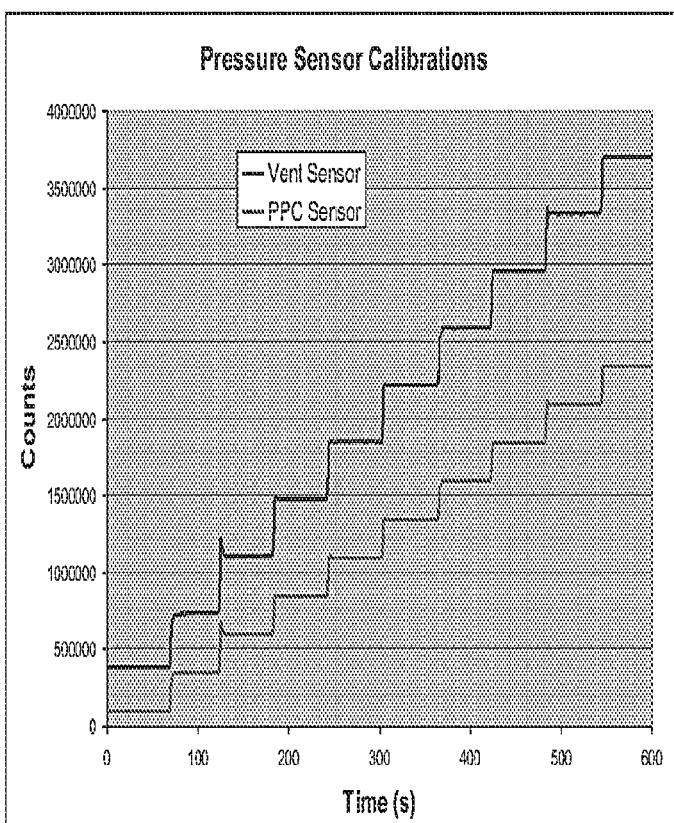
FIG. 29 is a graph showing the counts at the pressure sensors of FIG. 28 versus time, in accordance with certain examples.
Figure 30:
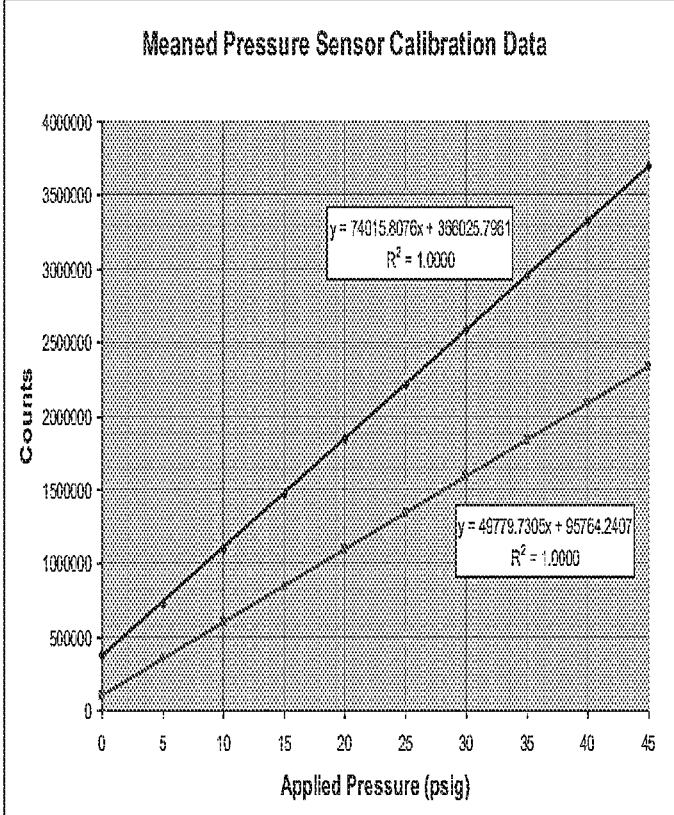
FIG. 30 is a graph showing the mean counts at the pressure sensors for a series of applied pressures, in accordance with certain examples.

Cables were attached to two pressure sensors 2810 and 2820 on the instrument as shown in FIG. 28 and connected to the analog inputs on a TotalChrom NCI 900 box. Data was collected from the sensors with a 0-10V input range and a 50 Hz collection rate. The first sensor (T1) 2810 was in the PPC pressure control module 2805 and the signal output was taken from pins 8 (signal) and 5 (ground) on the socket on the PPC control board. This signal represented the pressure seen by the PPC controller. The second sensor (T2) 2820 was in the sampling head 2815 purge line and the signal output was taken from pins 1 (signal) and 2 (ground). This signal represented the pressure close to that of the sampling needle and vial. A needle valve 2830 was connected to the column port on the sampling head 2815 as shown in FIG. 28. This needle valve was turned off for this test. The two sensors were calibrated over a range of pressures entered into the current HS method by recording the signals with TotalChrom as shown in FIG. 29. The top line represents the vent sensor, and the bottom line represents the PPC module sensor. The y-axis was re-scaled to reflect the digital counts rather than the mV signal. For each of the applied pressures, 1500 data points (30 seconds) were averaged and their means plotted as shown in FIG. 30. The top line in FIG. 30 represents the vent sensor, and the bottom line represents the PPC module sensor. The plot of FIG. 30 was used to calculate the pressures in the examples noted below.

Example 8

Vials with water were sealed and run on an unmodified TurboMatrix HS Trap (with the trap port sealed) under the conditions given in Table 6 and using hydrogen as a carrier gas. The TotalChrom data collection was initiated by manually pressing the START button on the NCI box as the elevator loaded the vial under test into the vial oven. This ensured that the pressures were monitored before, during and after the sampling process. It was difficult to automate the data collection start so a manual start had to be used. Some slight timing variation because of this is expected. The data obtained were processed using the calibration shown in FIG. 30 to provide plots showing how the pressure changed with time on the two pressure sensors.

TABLE 6

| Oven Temp (° C.) | 50 |
|---|---|
| Needle Temp (° C.) | 50 |
| Transfer Line Temp (° C.) | 50 |
| Thermostatting Time (min) | 1.0 |
| Pressurization Time (min) | 0.5 |
| Inject Time (min) | 0.04 |
| Withdraw Time (min) | 0.5 |
| GC Cycle Time (min) | 0.1 |
| PII Time (min) | 2.3 |
| Operating Mode | Constant (trap port capped) |
| Carrier Gas | Hydrogen |
| Column Pressure (psig) | a) 10.0 |
|  | b) 20.0 |
|  | c) 30.0 |
|  | d) 40.0 |
| Sample Volume (mL) | i) 0 |
|  | ii) 5 |
|  | iii) 10 |
| Inject Pressure (psig) | As Column Pressure |
| Column Flow Rate (mL/min) | Port sealed |
| Data Collection | NCI Box at 50 Hz |

Figure 31:
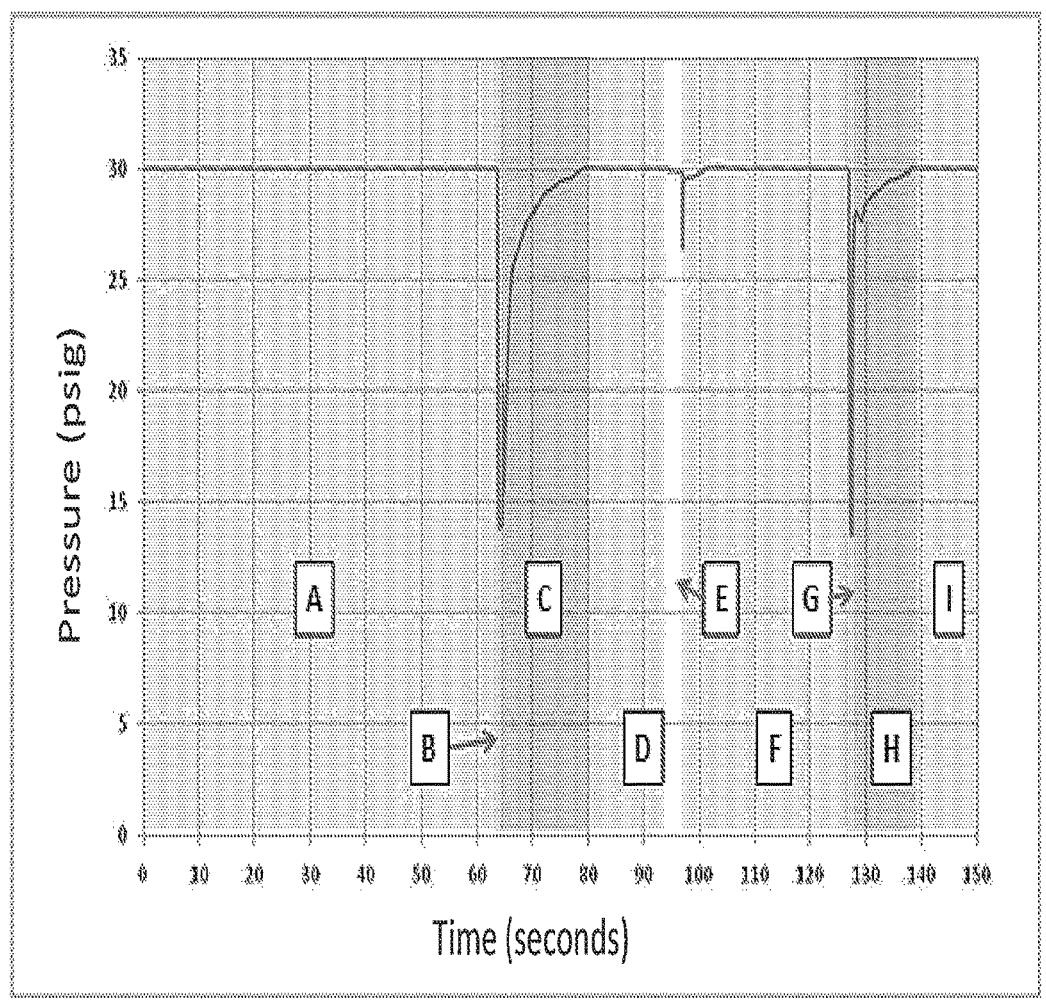
FIG. 31 is a graph showing an illustrative pressure profile with labeled areas, in accordance with certain examples.

Many different pressure profiles were then obtained. To better understand the pressure profiles noted below, FIG. 31 shows a typical pressure profile obtained from the pressure sensor located on the sampling head vent line. For the purposes of explanation, it has been divided up into 9 sections which are summarized in Table 7.

TABLE 7

| Section | Explanation |
|---|---|
| A | Constant pressure is applied during vial thermal equilibration |
| B | Sampling process starts. The needle is moved down into the vial. As the needle orifice passes through the gap between the sampling head seal and the vial septum, there is a large loss of gas and the pressure drops. This is one of the steps that is causing concerns with the use of hydrogen. |
| C | The needle is now inside the sealed vial and the pressure starts to build up. This is a very critical step in headspace analysis. The pressure should return to the original pressure in a smooth manner. Any fluctuations in this smoothness may cause pre-injection effects that are seen as ghost peaks in the chromatography. The time to recover is also important as the pressure should be stable before sampling occurs. Long recovery times may also extend the analysis time. |
| D | The pressure is held stable until the sampling starts. The time of this section plus that of Section C represent the 'Pressurize' time entry in the TurboMatrix method (0.5 min in this instance). |
| E | This is the sampling step. The carrier gas supply is turned off and headspace vapor flows out of the vial and into the GC column. This time is controlled by the 'Inject' time set in the TurboMatrix method (0.04 min in this instance). |
| F | After the sampling step has finished, the carrier gas is re-applied and the system waits for a period defined by the method 'Withdrawal' time. When the needle is withdrawn as described in Section G, there is a sudden drop in pressure. The withdrawal time ensures that sufficient time is given for the vapor to travel down the column and not be pulled back out by this sudden pressure drop. In this instance the Withdrawal time was set to 0.5 min. |
| G | As the needle is pulled out of the vial, the outlet orifice is exposed to ambient air and there is a sudden loss of carrier gas causing a pressure drop. This is the second step causing concern with the use of hydrogen. |
| H | When the needle is fully withdrawn, it is fully re-sealed and the internal pressure inside the sampling head recovers to the set point in the method. The vial is no longer connected. |
| I | The sampling process is complete and carrier gas pressure is maintained at the method set point during the chromatography. |

Figure 32C:
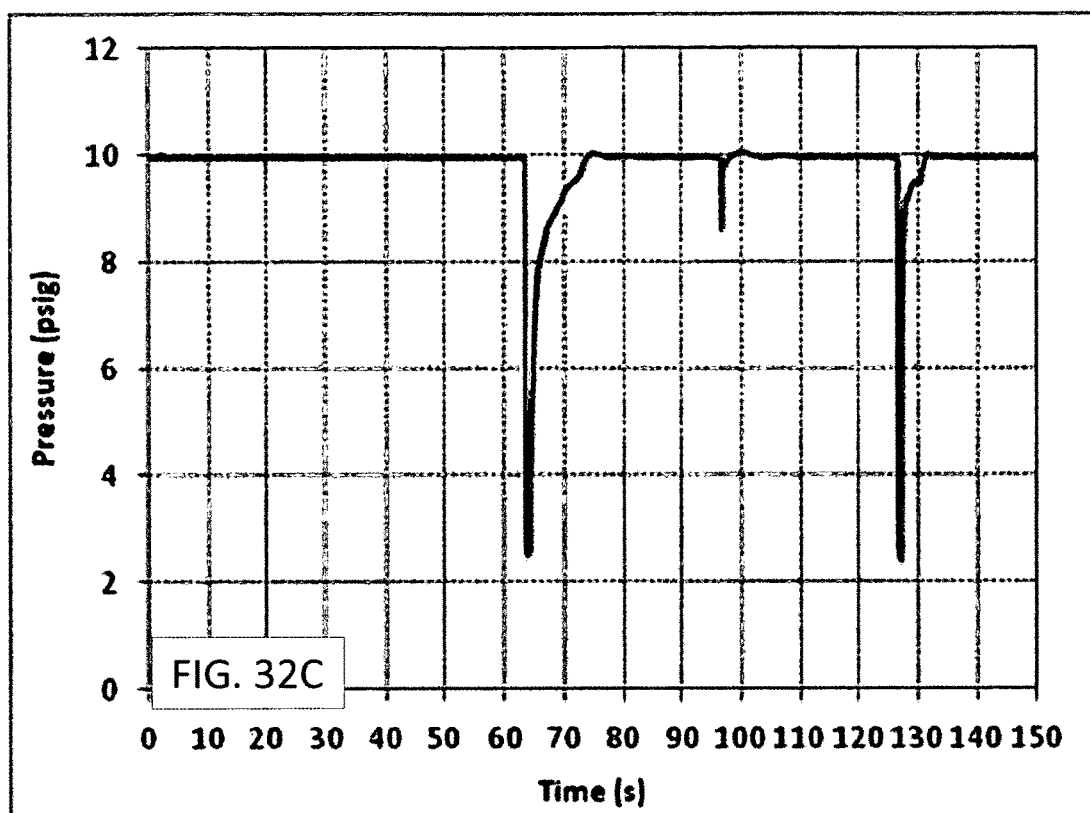
FIGS. 32A-32X are pressure profiles at various conditions, in accordance with certain examples.
Figure 32D:
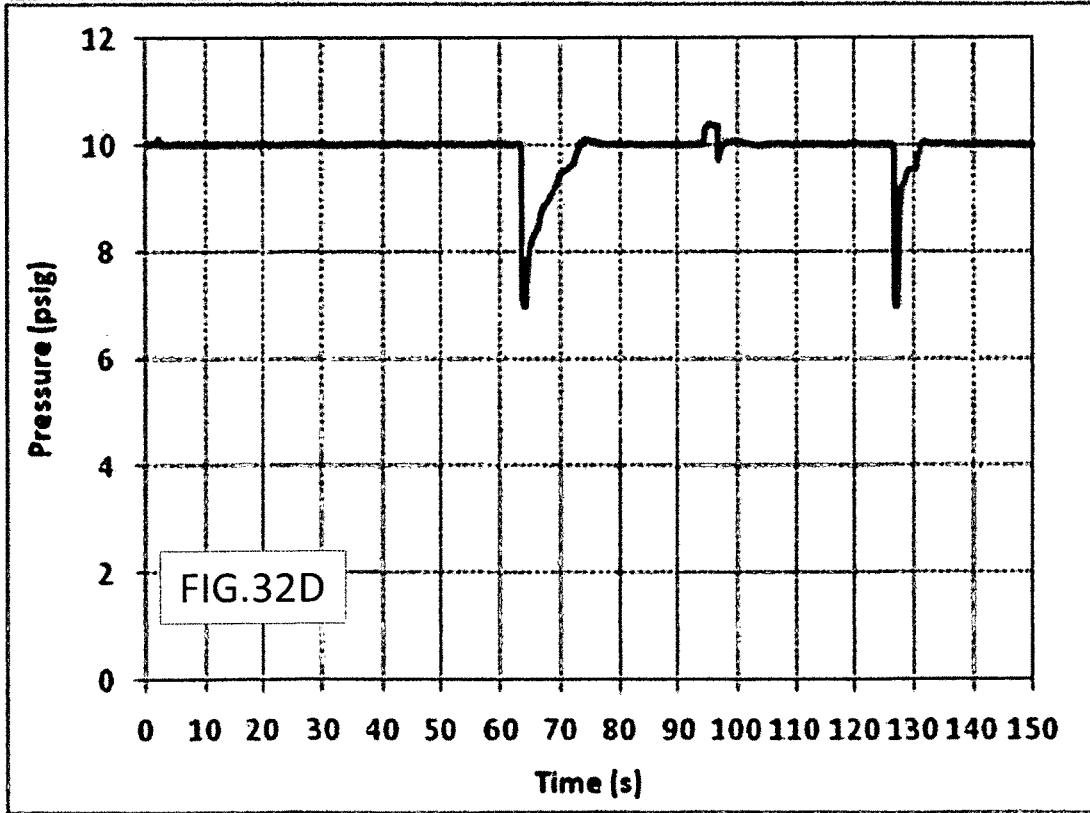
Figure 32I:
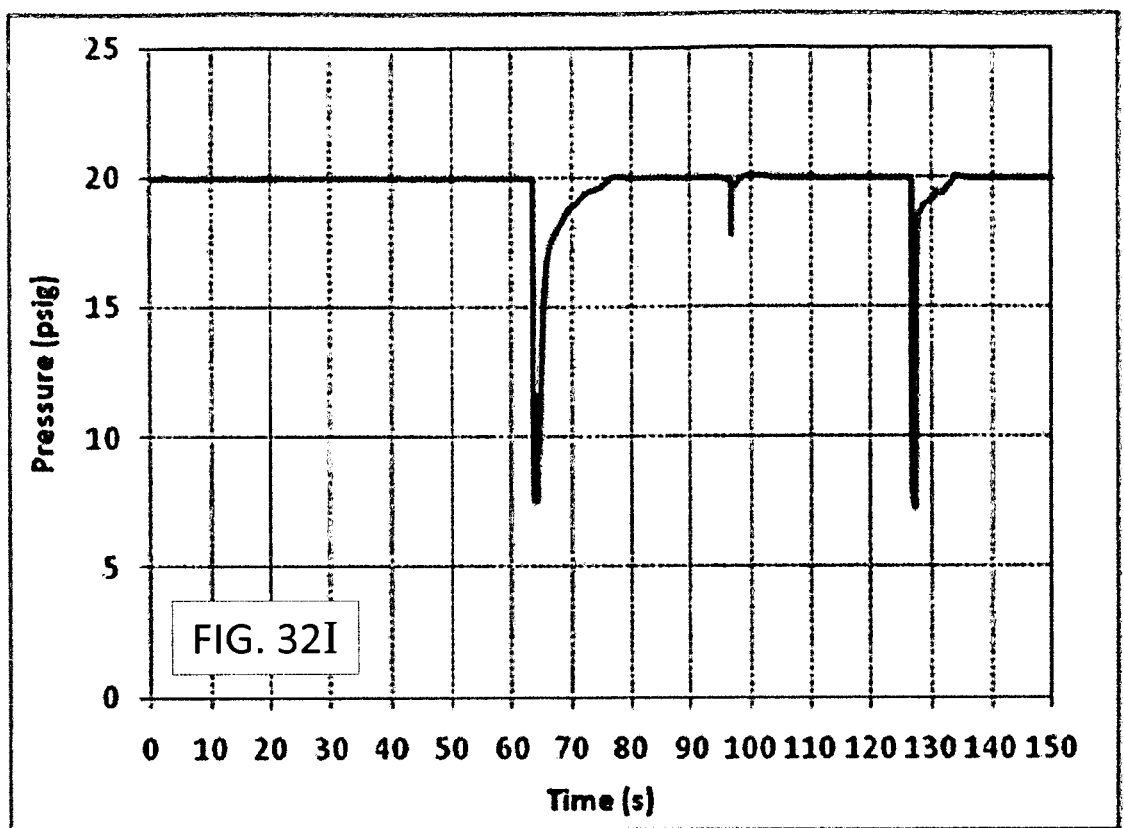
Figure 32J:
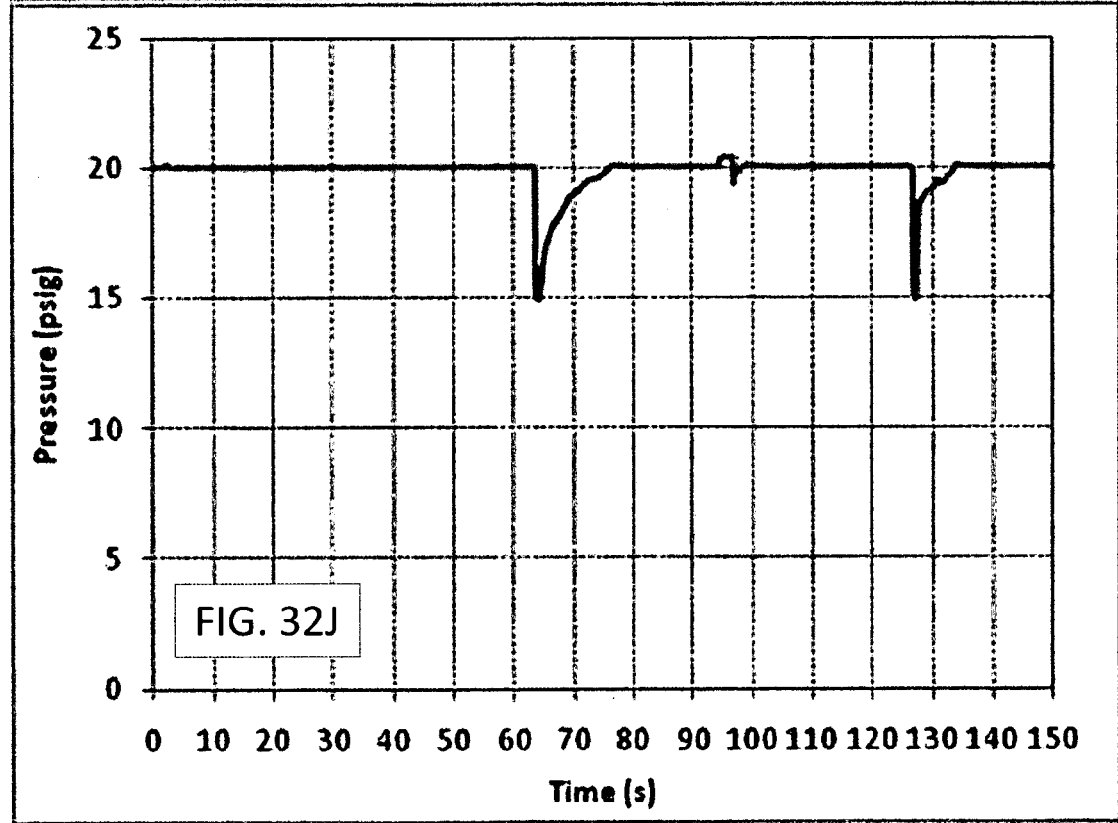
Figures 32S, 32T:
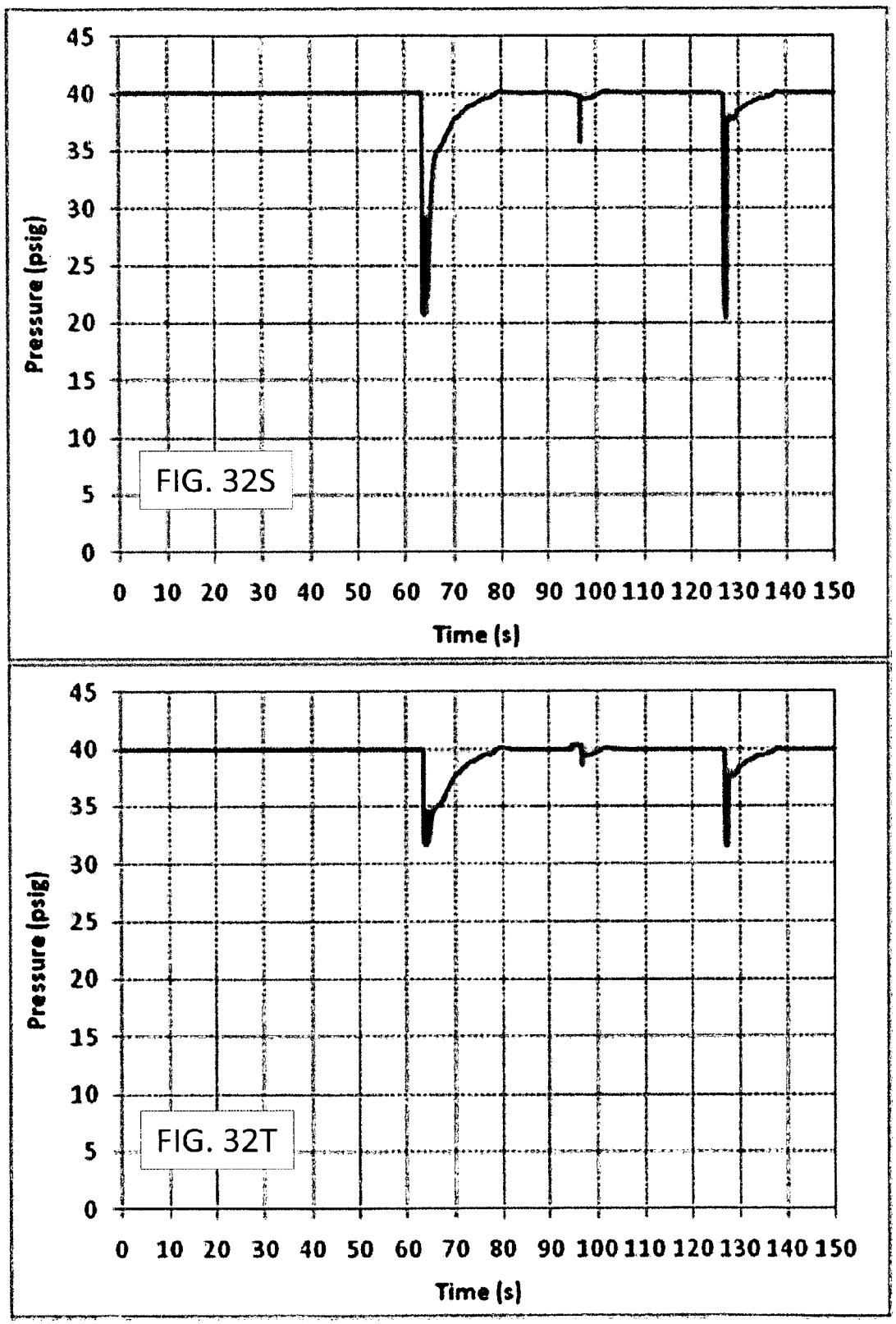
Figure 32W:
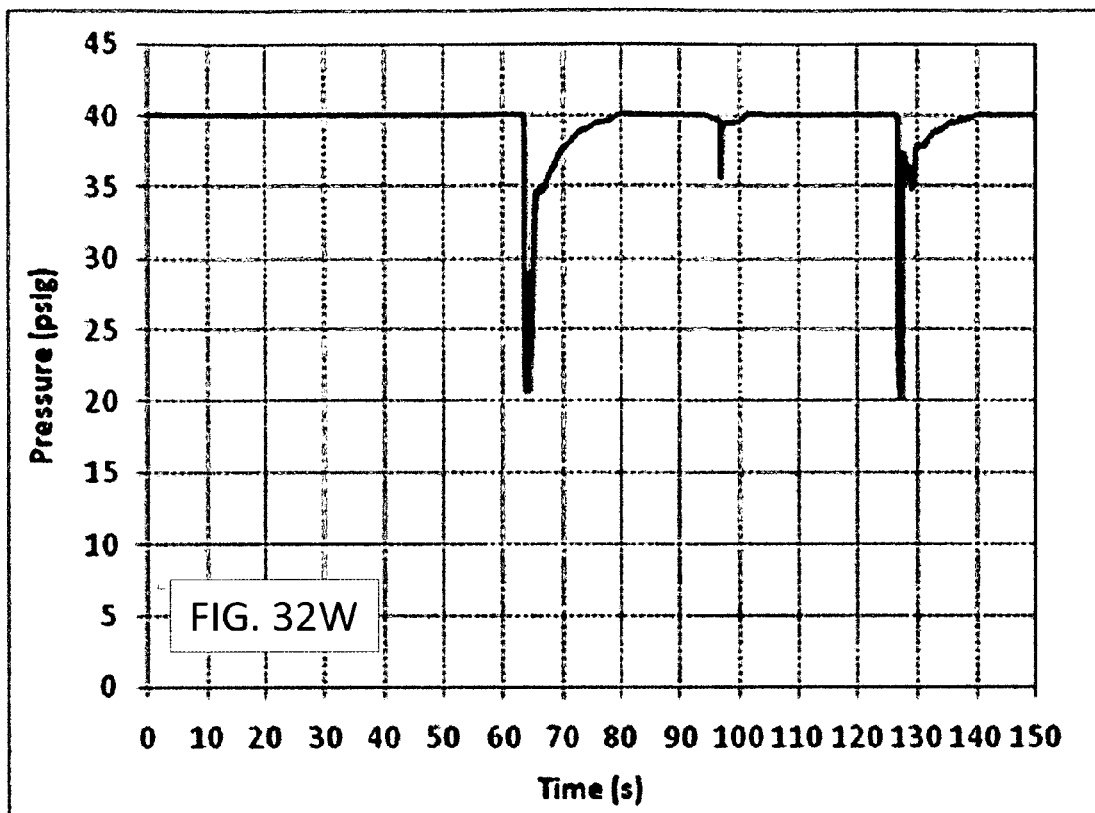
Figure 32X:
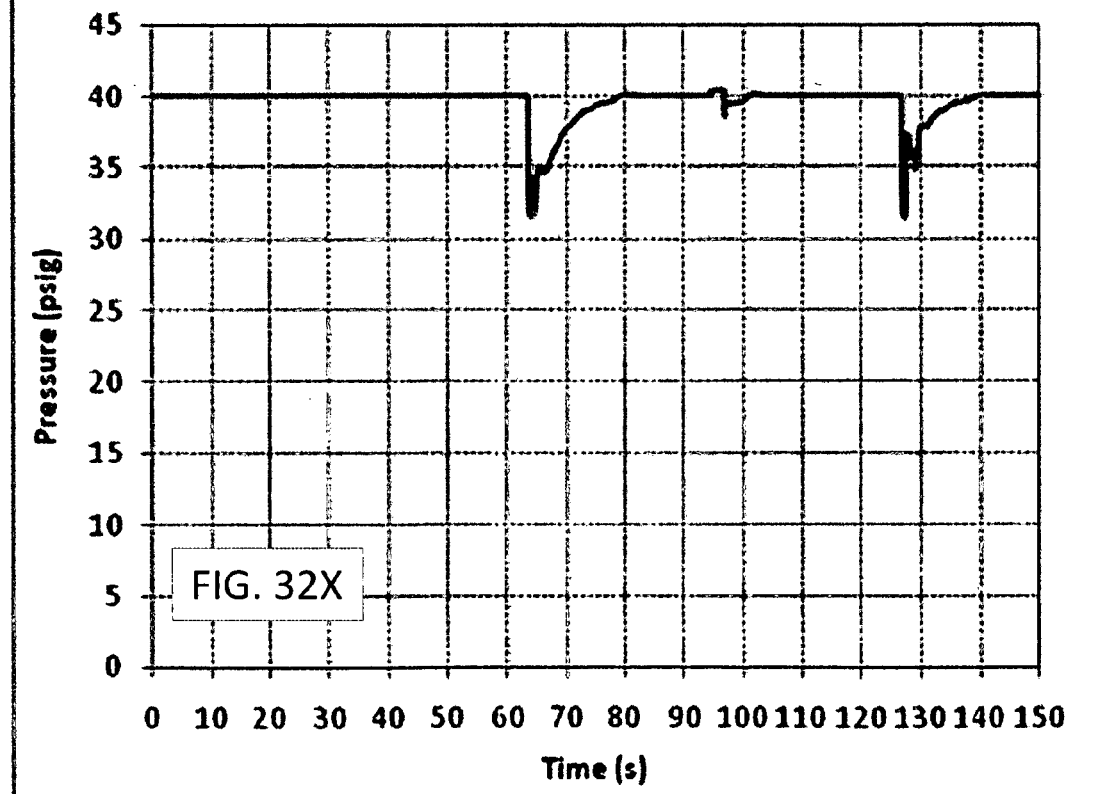

The pressure profiles for the 12 sets of conditions shown in Table 6 from both sensors are shown in FIGS. 32A to 32X with the graphs corresponding to the following: 32A corresponds to the vent sensor at 10 psig column pressure, 0 mL sample; 32B corresponds to the PPC sensor at 10 psig column pressure, 0 mL sample; 32C corresponds to the vent sensor at 10 psig column pressure, 5 mL sample; 32D corresponds to the PPC sensor at 10 psig column pressure, 5 mL sample; 32E corresponds to the vent sensor at 10 psig column pressure, 10 mL sample; 32F corresponds to the PPC sensor at 10 psig column pressure, 10 mL sample; 32G corresponds to the vent sensor at 20 psig column pressure, 0 mL sample; 32H corresponds to the PPC sensor at 20 psig column pressure, 0 mL sample; 32I corresponds to the vent sensor at 20 psig column pressure, 5 mL sample; 32J corresponds to the PPC sensor at 20 psig column pressure, 5 mL sample; 32K corresponds to the vent sensor at 20 psig column pressure, 10 mL sample; 32L corresponds to the PPC sensor at 20 psig column pressure, 10 mL sample; 32M corresponds to the vent sensor at 30 psig column pressure, 0 mL sample; 32N corresponds to the PPC sensor at 30 psig column pressure, 0 mL sample; 32O corresponds to the vent sensor at 30 psig column pressure, 5 mL sample; 32P corresponds to the PPC sensor at 30 psig column pressure, 5 mL sample; 32R corresponds to the vent sensor at 30 psig column pressure, 10 mL sample; 32S corresponds to the PPC sensor at 30 psig column pressure, 10 mL sample; 32T corresponds to the vent sensor at 40 psig column pressure, 0 mL sample; 32Q corresponds to the PPC sensor at 40 psig column pressure, 0 mL sample; 32U corresponds to the vent sensor at 40 psig column pressure, 5 mL sample; 32V corresponds to the PPC sensor at 40 psig column pressure, 5 mL sample; 32W corresponds to the vent sensor at 40 psig column pressure, 10 mL sample; and 32X corresponds to the PPC sensor at 40 psig column pressure, 10 mL sample.

In general these pressure profiles are acceptable. The pressures at the vent sensor seem to track the set pressure very well. The Section C recovery is generally smooth.

Another key factor is the time taken for the pressure to recover after the needle has entered the vial (Section C in FIG. 31). Table 8 summarizes these times taken from FIGS. 32A-32X.

TABLE 1

| | Sample Volume (mL) | | |
|---|---|---|---|
| Pressure (psig) | 0 | 5 | 10 |
| 10 | 12 | 12 | 12 |
| 20 | 14 | 13 | 12 |
| 30 | 16 | 14 | 14 |
| 40 | 16 | 16 | 16 |

There is not a lot of difference between these times. It is assumed that the PPC controller is being throttled during the vial pressurization cycle which would tend to normalize these times.

Finally, a check was made on the unrestricted flow rate of hydrogen from the PPC module. In the initial investigation, the flow rate was checked on a sampling head removed for an instrument and supplied by a manual pressure regulator. This earlier data is shown in FIG. 11.

Figure 33:
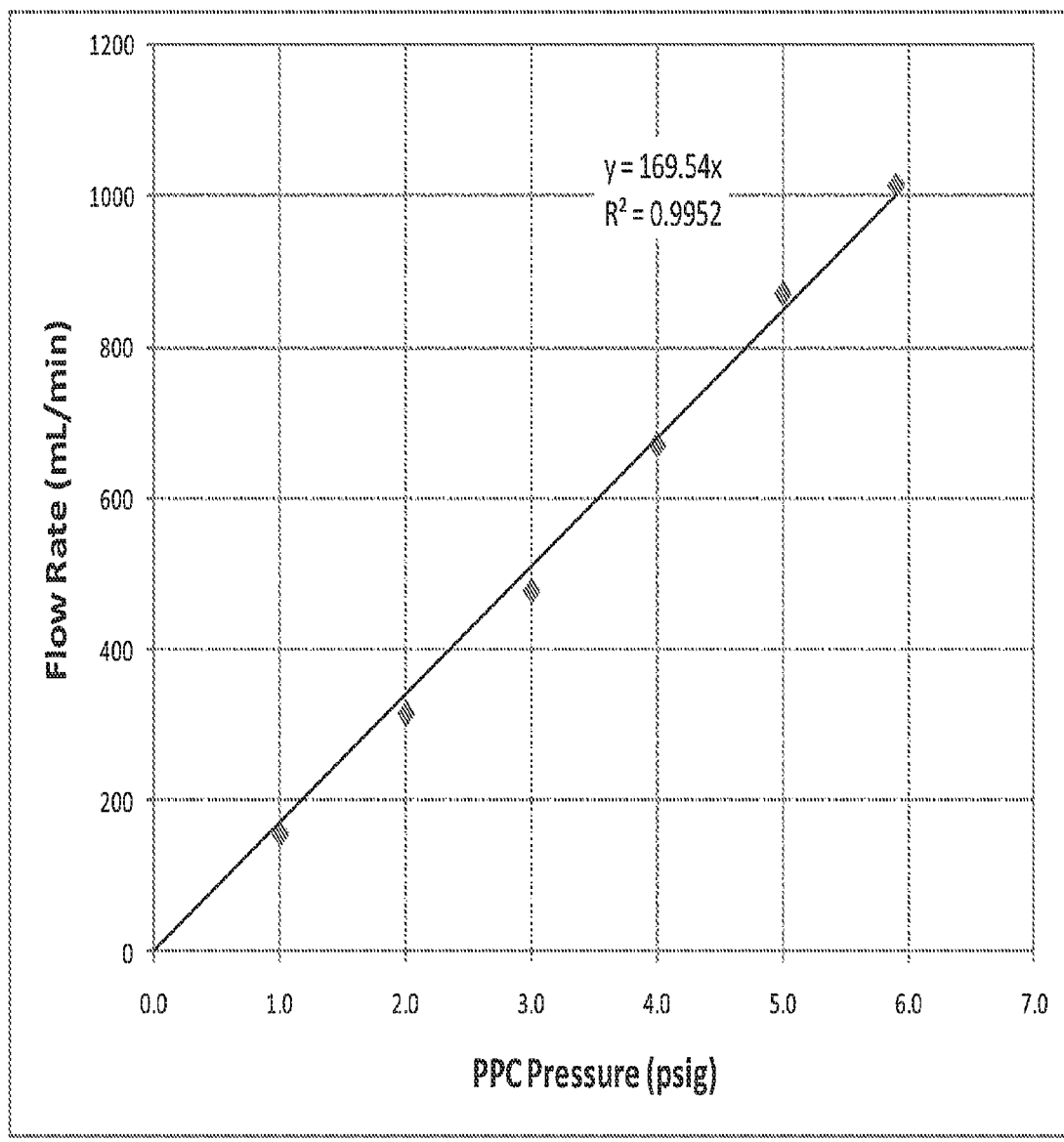
FIG. 33 is a graph showing the measured flow rate of hydrogen, in accordance with certain examples.

The flow rate of hydrogen was checked on the test system of this example with the PPC control over a range of pressures up to a flow rate of 1,000 mL/min (maximum reading on the electronic flow meter being used). These data will serve as a check to see if the predictions from the initial report regarding potential hydrogen emissions were applicable to the test system. These data are shown in FIG. 33. These flow rates are even higher than those observed previously. The total volume of gas emitted was determined by measuring the emission time from videos of the sampling head being operated. The total time was determined to be approximately 1.7 seconds. Inspection of the dynamic pressures shown in the figures (FIG. 32W was used as a representative figure) provides that that hydrogen is being emitted for a total of 0.8+0.6=1.4 seconds. The volume of hydrogen being emitted is similar to that predicted by the initial investigation.

Figure 34:
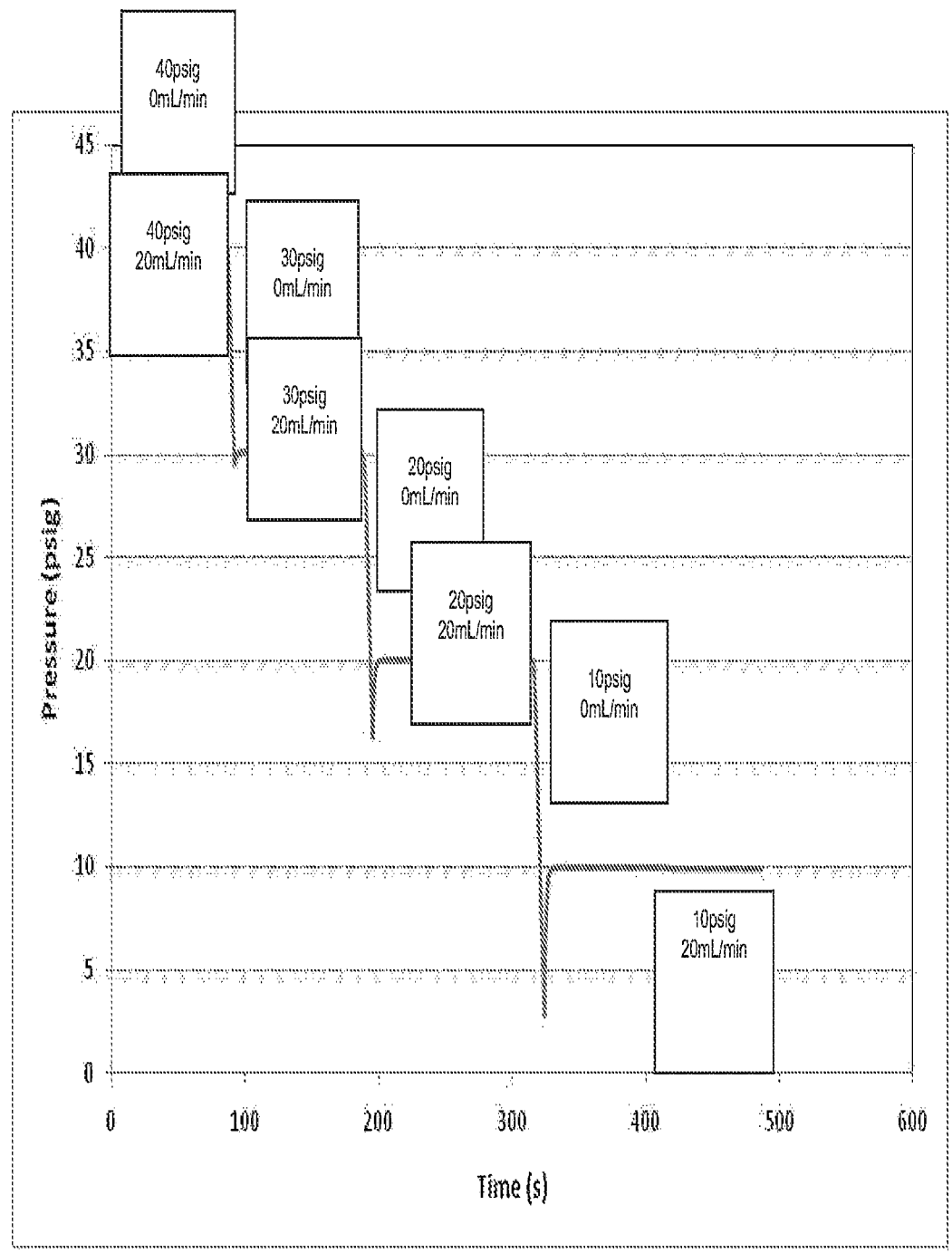
FIG. 34 is a graph showing the measured flow rate of hydrogen when a PPC controller is directly connected to a sample head, in accordance with certain examples.

A final test on the system with the PPC controller directly connected to the sampling head was to check how the pressure at the GC column inlet or transfer line inlet would be affected by the flow rate. At each of the 4 pressures, the needle valve was first turned off and then adjusted to 20 mL/min. The pressure at the vent sensor was recorded at both flow rates. This test was performed while the HS system was at standby and so gas would be flowing out of the PPC bleed vent (~30 mL/min) and the sampling head purge vent (~30 mL/min also). The results of this test are shown in Table 9 and FIG. 34.

TABLE 9

|  | Pressure at Column Port (psig) | |
| --- | --- | --- |
| PPC Pressure (psig) | Flow Rate = 0 mL/min | Flow Rate = 20 mL/min |
| 10 | 10.0 | 9.9 |
| 20 | 20.0 | 20.0 |
| 30 | 30.0 | 30.0 |
| 40 | 40.0 | 40.0 |

The effect of changing the flow rate had very little effect on the pressure seen at the column or transfer line inlet and so excellent pneumatic coupling exists between the PPC regulator and the GC column.

Example 9

Figures 35A, 35B:
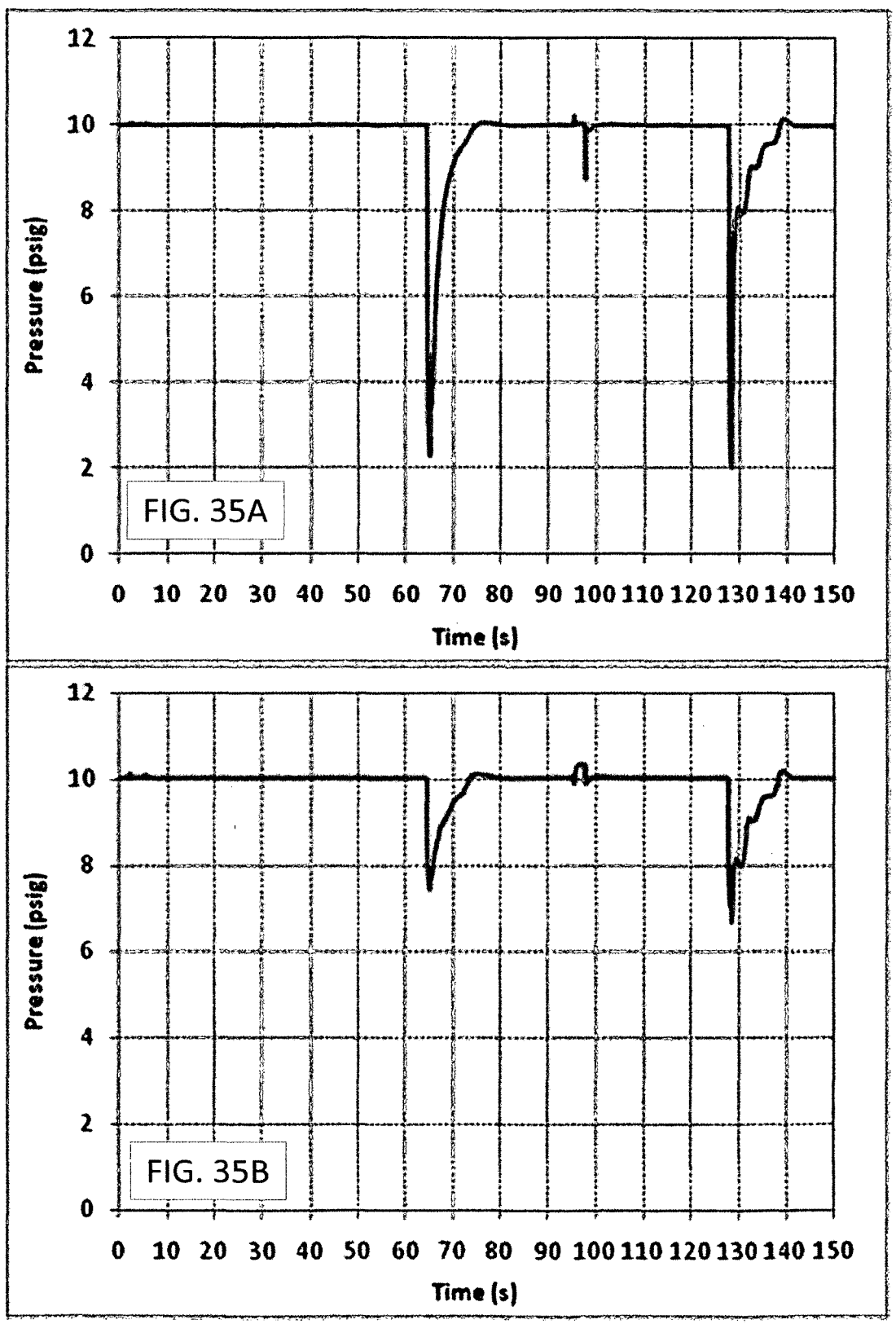
FIGS. 35A-35X are pressure profiles at various conditions, in accordance with certain examples.
Figure 35G:
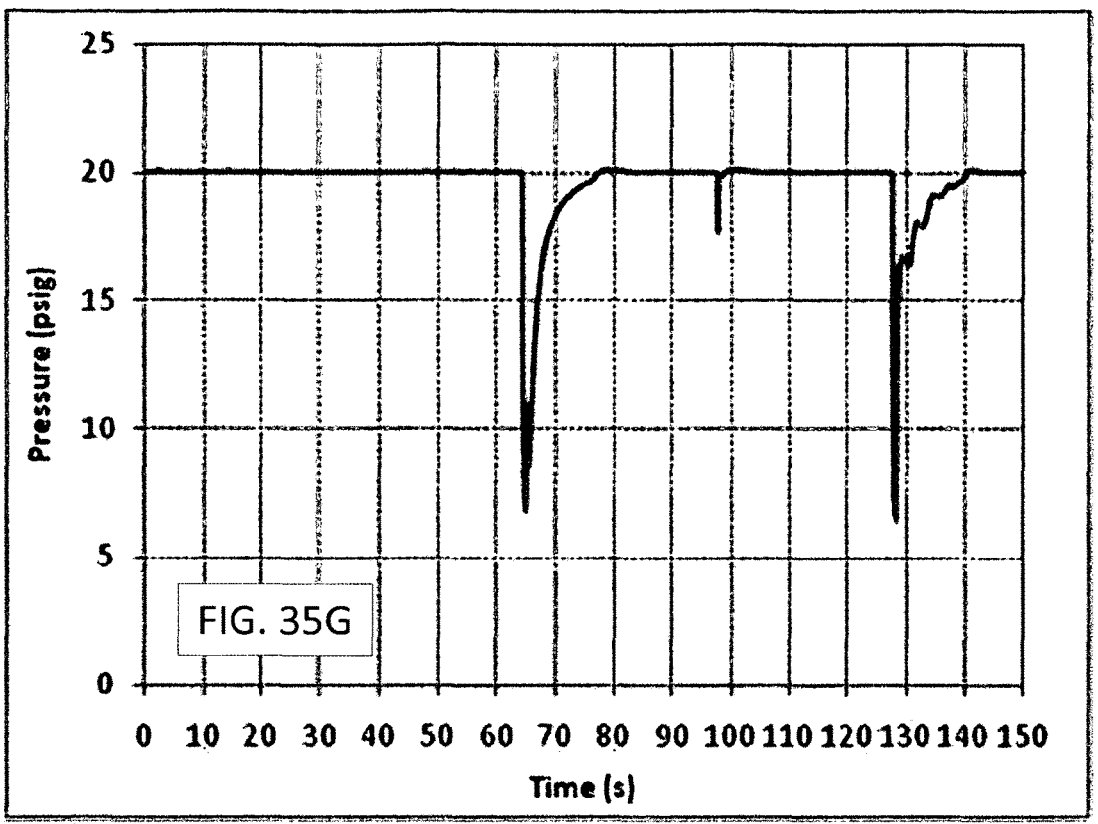
Figure 35H:
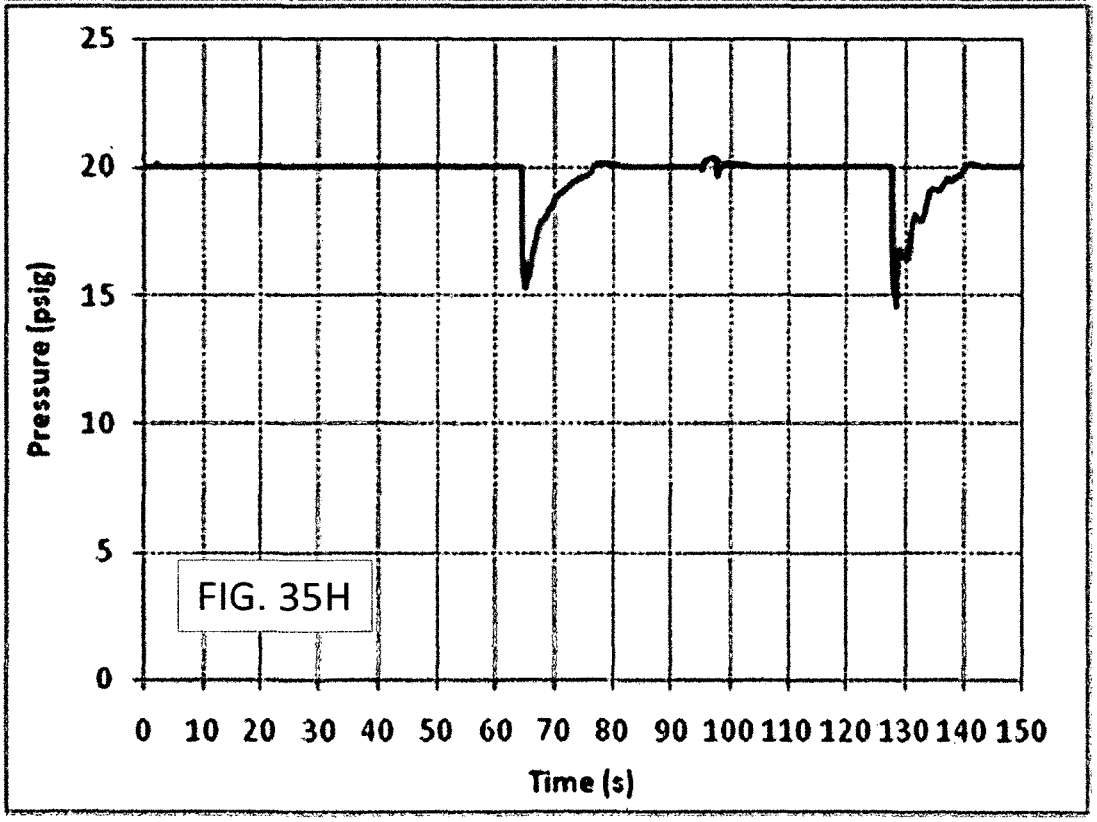
Figures 35K, 35L:
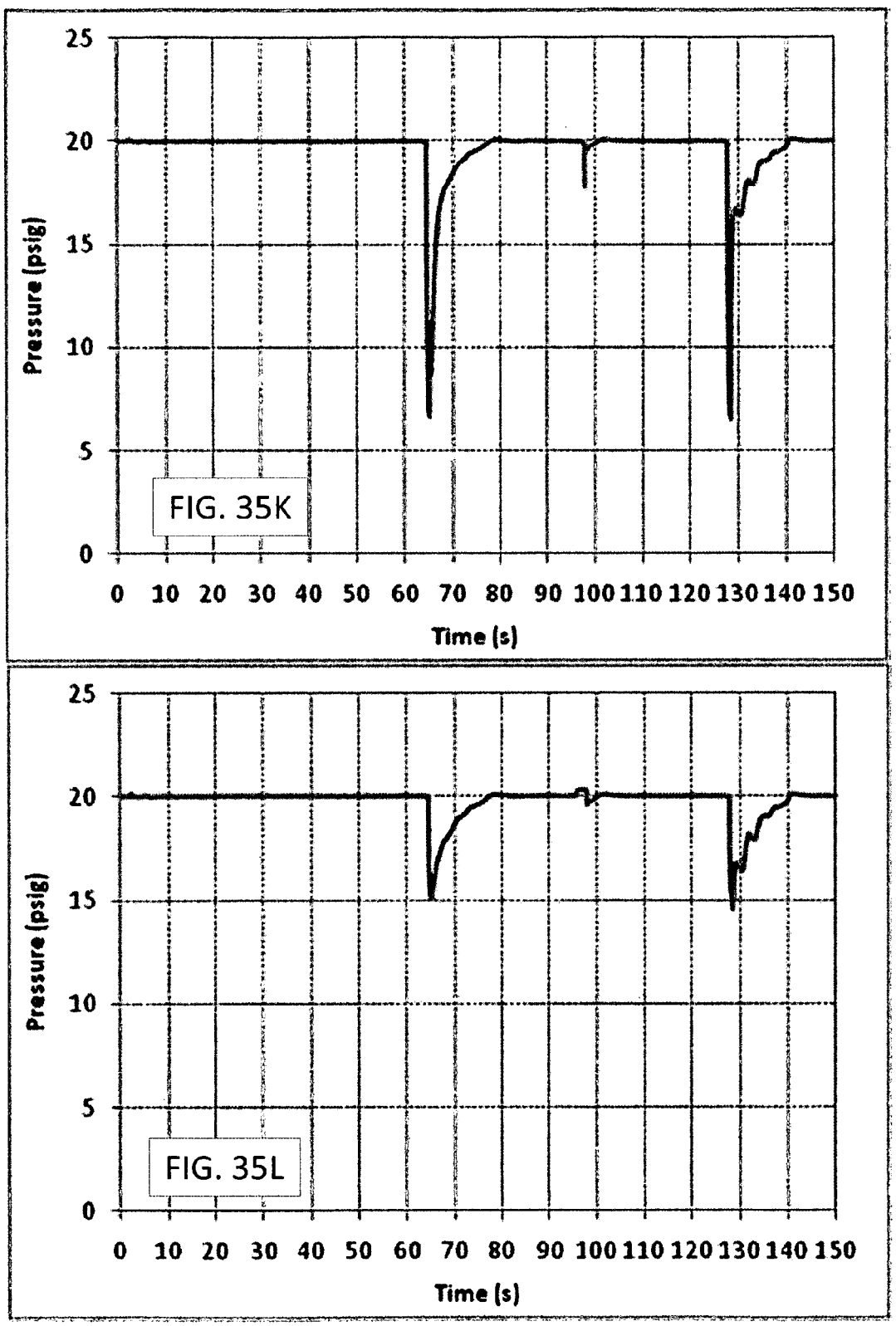
Figure 35O:
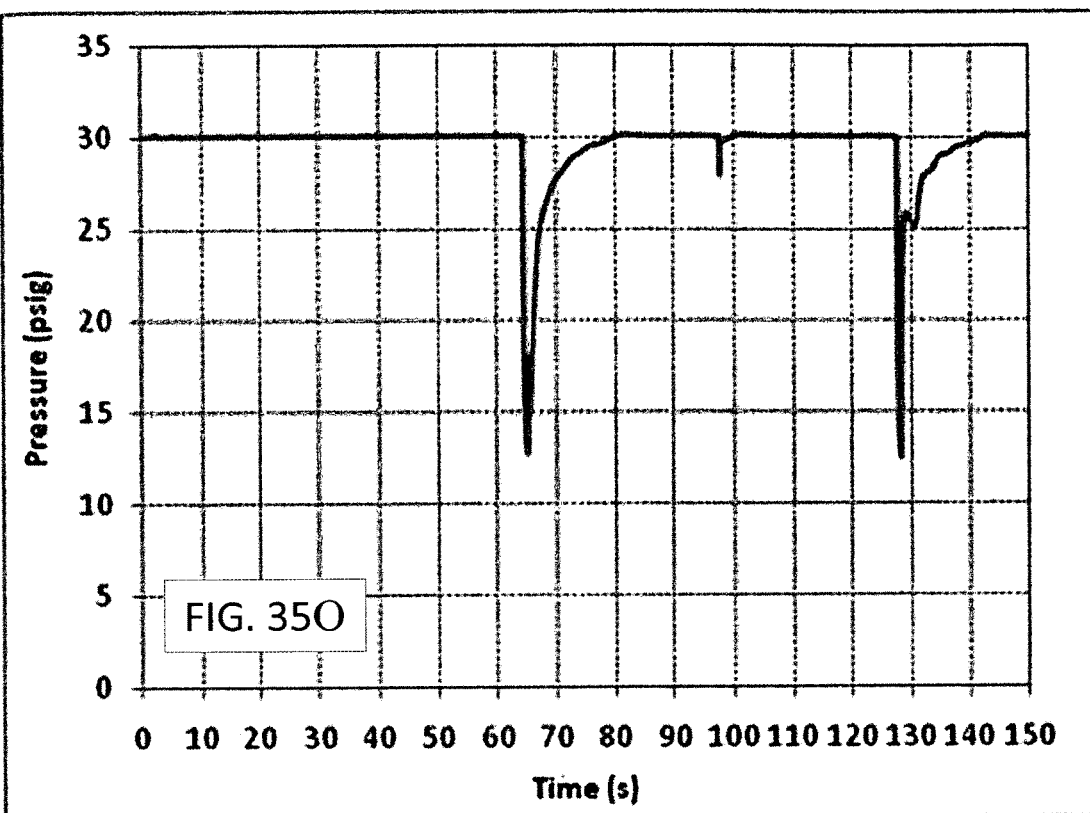
Figure 35P:
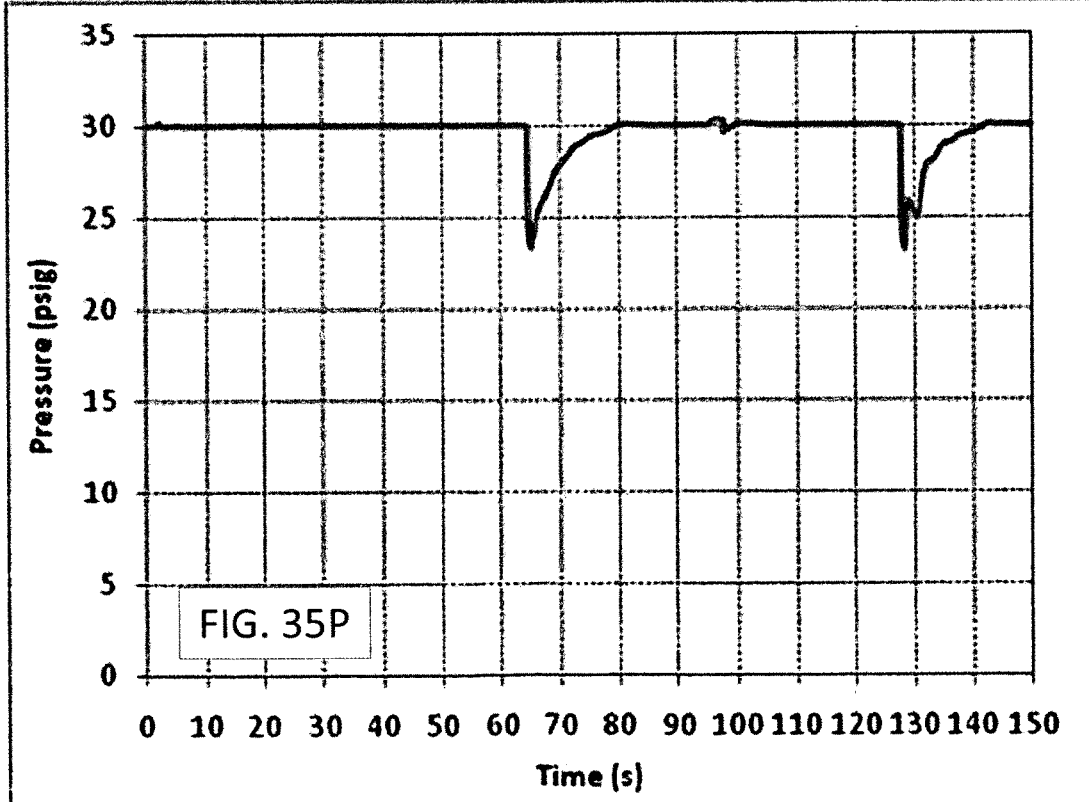
Figures 35W, 35X:
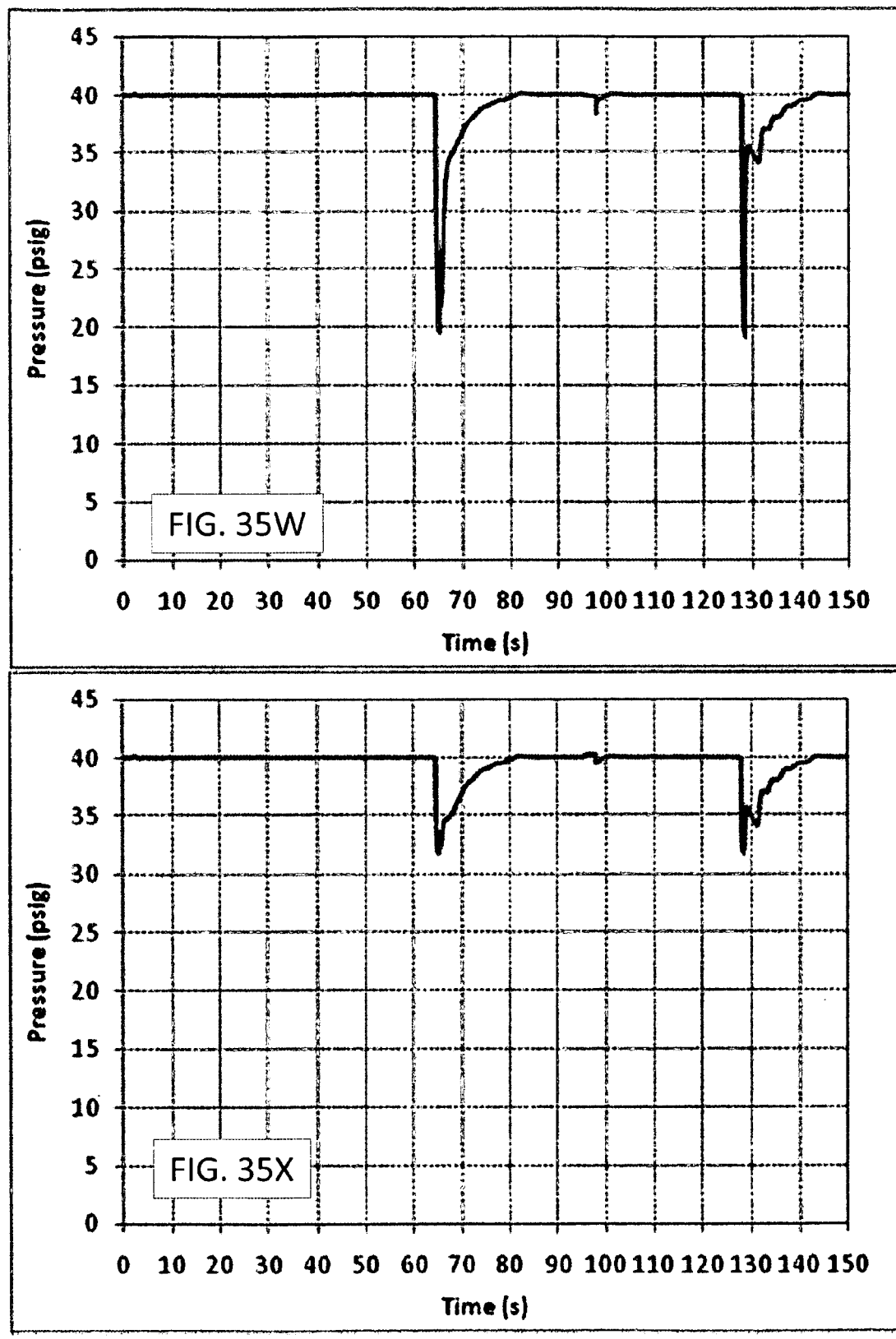

To compare the dynamic pressure profiles for hydrogen (Example 8), equivalent profiles were collected using helium carrier gas. Helium profiles at the 4 pressures and 3 sample sizes at each of the 2 sensors are presented in FIGS. 35A to 35X. The figures correspond as follows: 35A corresponds to the vent sensor at 10 psig column pressure, 0 mL sample; 35B corresponds to the PPC sensor at 10 psig column pressure, 0 mL sample; 35C corresponds to the vent sensor at 10 psig column pressure, 5 mL sample; 35D corresponds to the PPC sensor at 10 psig column pressure, 5 mL sample; 35E corresponds to the vent sensor at 10 psig column pressure, 10 mL sample; 35F corresponds to the PPC sensor at 10 psig column pressure, 10 mL sample; 35G corresponds to the vent sensor at 20 psig column pressure, 0 mL sample; 35H corresponds to the PPC sensor at 20 psig column pressure, 0 mL sample; 35I corresponds to the vent sensor at 20 psig column pressure, 5 mL sample; 35J corresponds to the PPC sensor at 20 psig column pressure, 5 mL sample; 35K corresponds to the vent sensor at 20 psig column pressure, 10 mL sample; 35L corresponds to the PPC sensor at 20 psig column pressure, 10 mL sample; 35M corresponds to the vent sensor at 30 psig column pressure, 0 mL sample; 35N corresponds to the PPC sensor at 30 psig column pressure, 0 mL sample; 35O corresponds to the vent sensor at 30 psig column pressure, 5 mL sample; 35P corresponds to the PPC sensor at 30 psig column pressure, 5 mL sample; 35Q corresponds to the vent sensor at 30 psig column pressure, 10 mL sample; 35R corresponds to the PPC sensor at 30 psig column pressure, 10 mL sample; 35S corresponds to the vent sensor at 40 psig column pressure, 0 mL sample; 35T corresponds to the PPC sensor at 40 psig column pressure, 0 mL sample; 35U corresponds to the vent sensor at 40 psig column pressure, 5 mL sample; 35V corresponds to the PPC sensor at 40 psig column pressure, 5 mL sample; 35W corresponds to the vent sensor at 40 psig column pressure, 10 mL sample; and 35X corresponds to the PPC sensor at 40 psig column pressure, 10 mL sample.

The results from these tests are rather surprising. The pressure recovery profiles are not very smooth and it appears as if the PPC module is struggling to retain control of the pressure. There is evidence of slight pressure overshoot during vial pressurization and it appears that there is oscillation in the control during needle withdrawal. Although the system may appear to work analytically, these data indicate that operation is rather marginal. The differences between these results and those obtained with hydrogen are assumed to be because of the higher viscosity of helium. This extra viscosity effectively decouples the pneumatic operations within the sampling head and so the PPC control experiences some response lag. There is a bigger difference between the pressure excursions observed on the two sensors. Again this is thought to be from the viscosity differences. The vial pressurization times, which are summarized in Table 10, are similar to those seen when using hydrogen as shown in Table 8. Again PPC throttling is thought to be responsible for the similar results.

TABLE 10

|  | Sample Volume (mL) | | |
| --- | --- | --- | --- |
| Pressure (psig) | 0 | 5 | 10 |
| 10 | 11 | 12 | 10 |
| 20 | 13 | 13 | 13 |
| 30 | 16 | 15 | 15 |
| 40 | 16 | 16 | 17 |

The main implication of these data is that better analytical performance should be achieved when using hydrogen rather than helium.

Example 10

Figure 36:
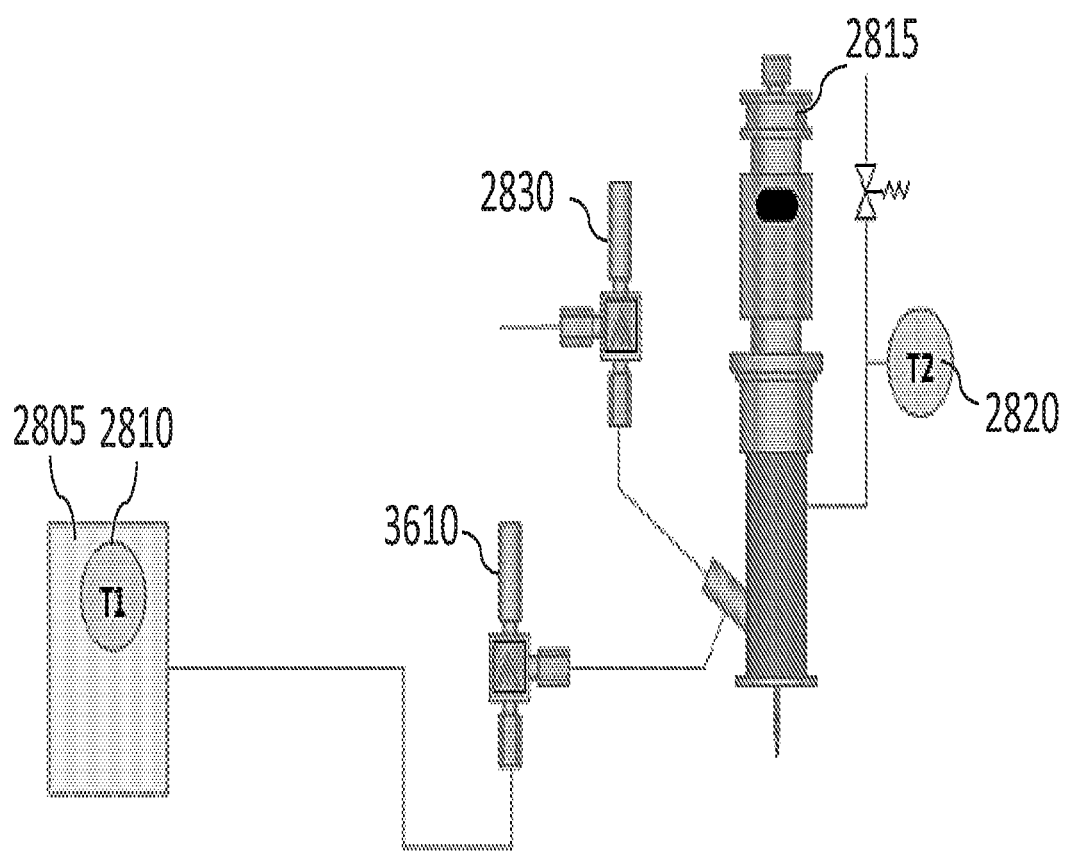
FIG. 36 is a schematic of a system comprising a fixed restrictor, in accordance with certain examples.

A fixed restrictor in the carrier gas supply for flow limitation was used to perform several tests. A needle valve was connected in-line between the PPC regulator and the line feeding the sampling head. This acted as an adjustable restrictor (but fixed during the test) and hence flow limiter feeding the sampling needle. FIG. 36 shows a schematic of the setup. FIG. 36 is similar to the setup of FIG. 28 except a second needle valve 3610 was connected to the column port on the sampling head 2815 to enable the flow rate down the transfer line to be simulated.

Figures 37C, 37D:
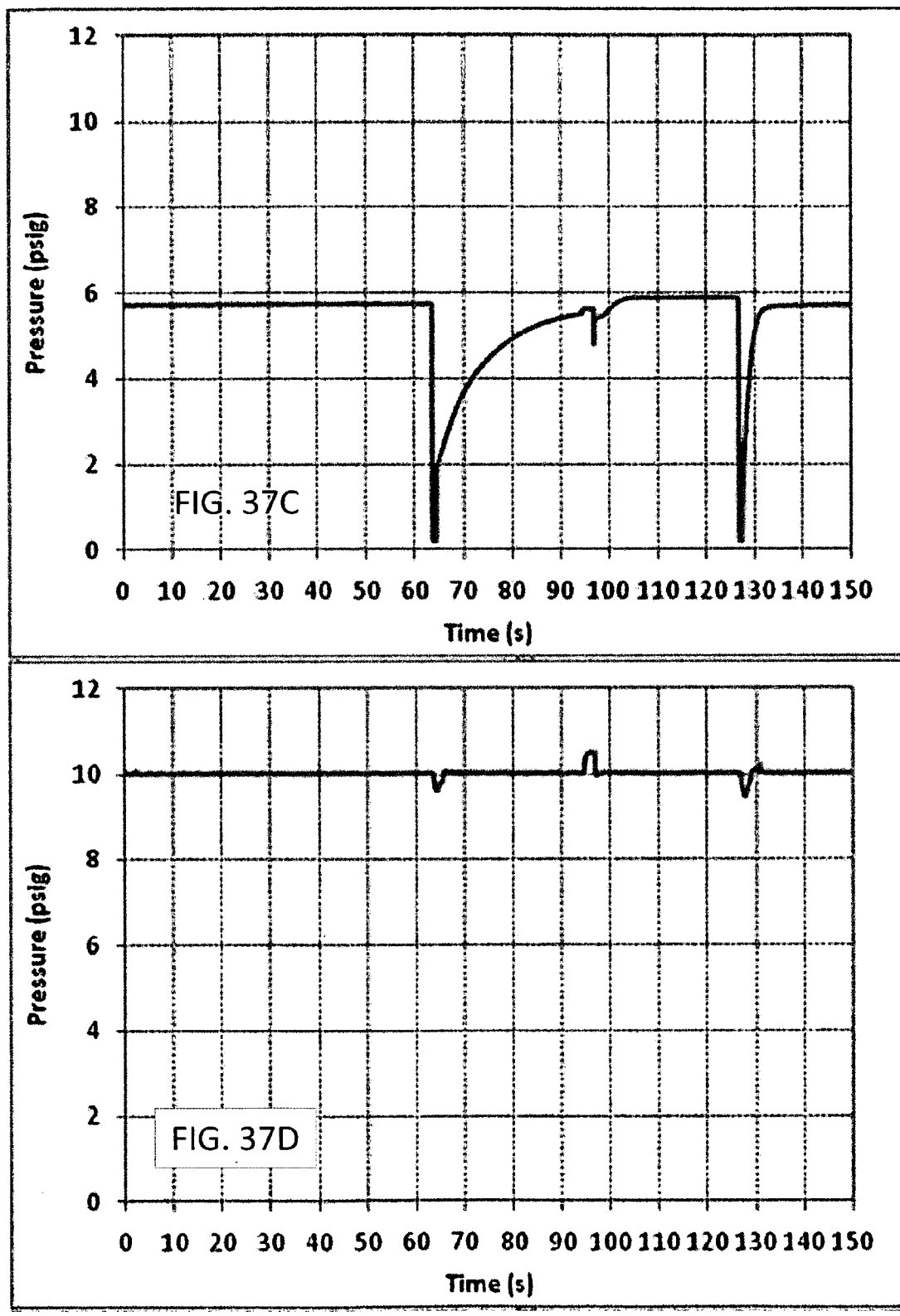
FIGS. 37A-37X are pressure profiles obtained using the setup of FIG. 36, in accordance with certain examples.
Figures 37G, 37H:
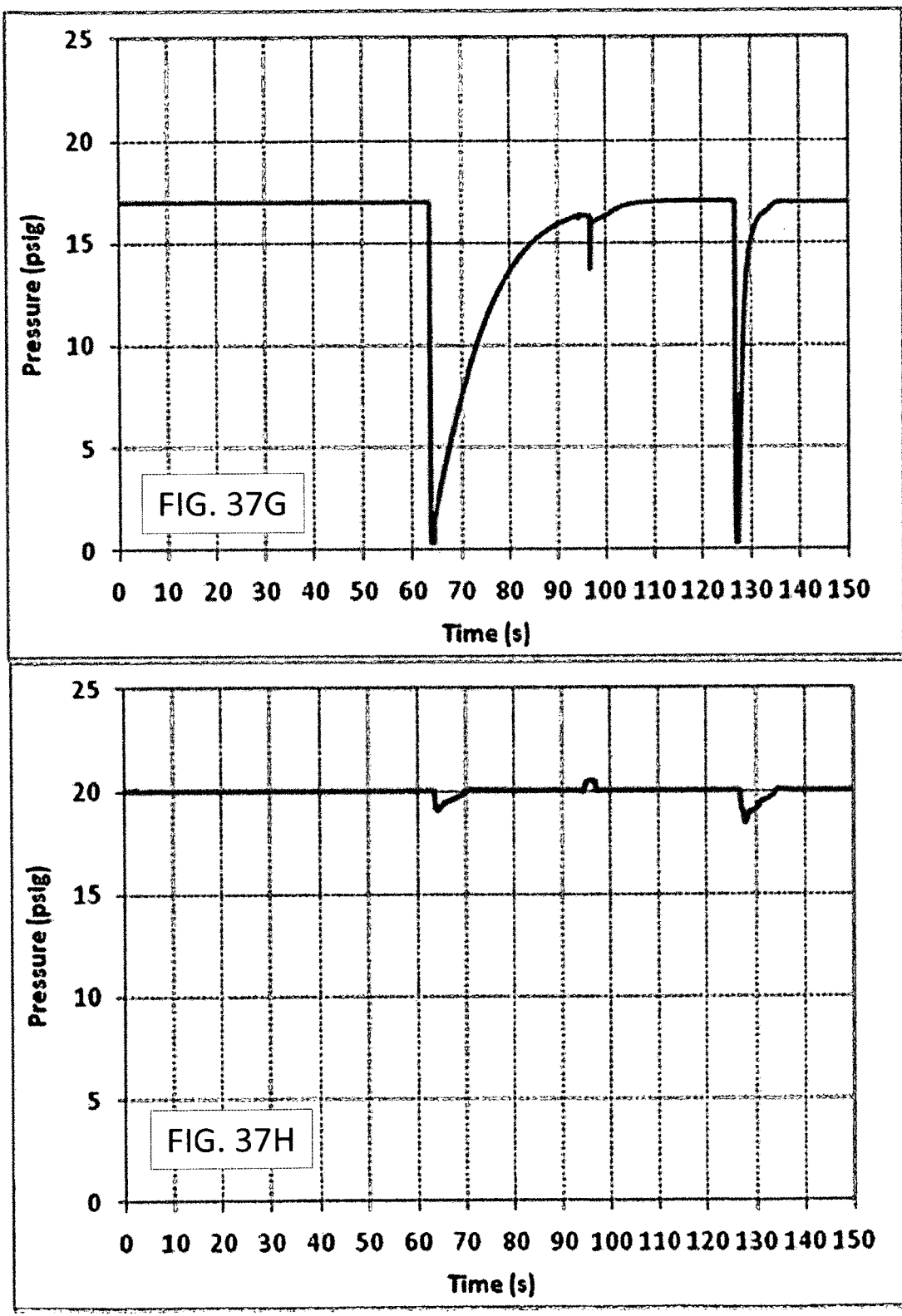
Figure 37O:
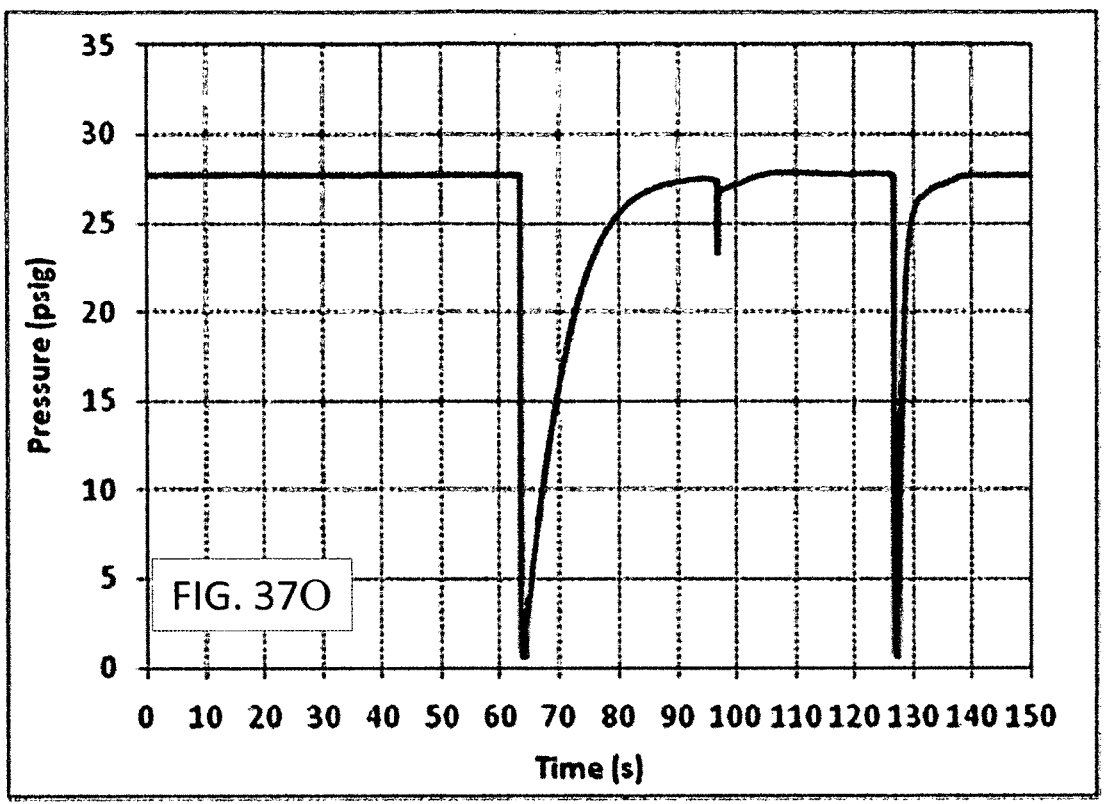
Figure 37P:
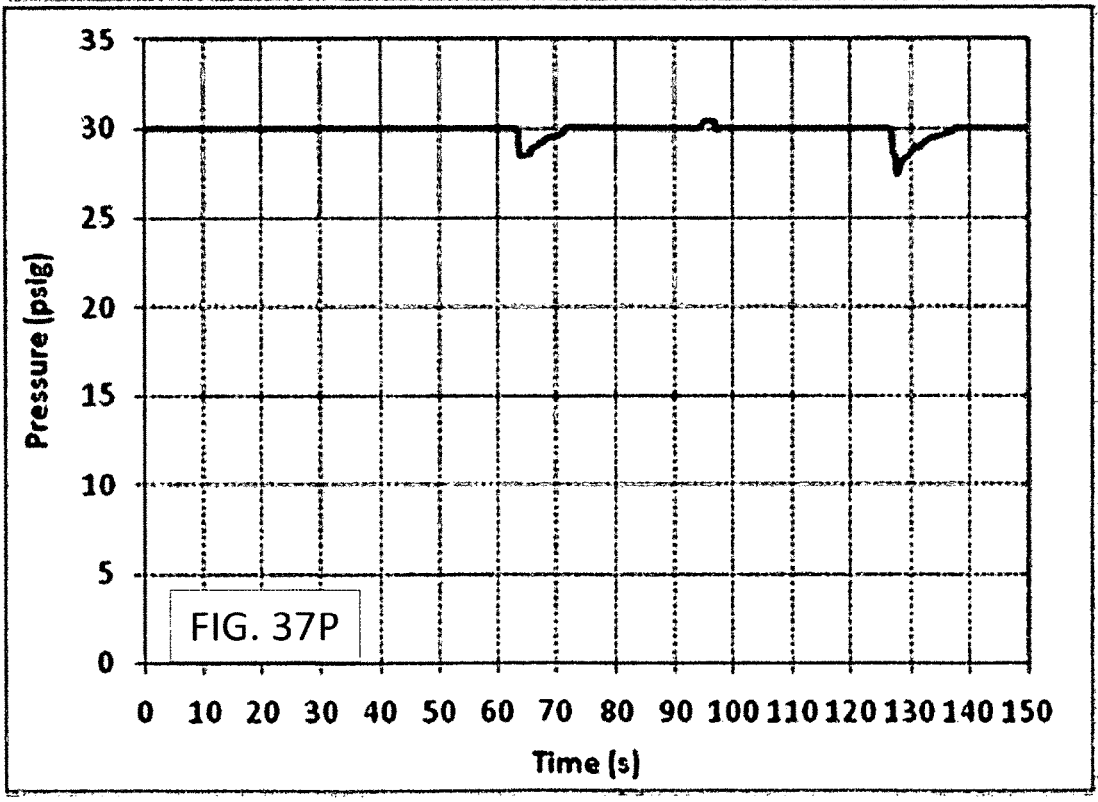

Hydrogen was applied at 40 psig and the in-line needle valve was adjusted to deliver 400 mL/min to atmospheric pressure (i.e. with the second needle valve wide open). The second needle valve was turned off and the experimental conditions given in Table 6 were applied. The resultant pressure profiles are shown in FIGS. 37A to 37X. These graphs correspond to the following parameters: 37A corresponds to the vent sensor at 10 psig column pressure, 0 mL sample; 37B corresponds to the PPC sensor at 10 psig column pressure, 0 mL sample; 37C corresponds to the vent sensor at 10 psig column pressure, 5 mL sample; 37D corresponds to the PPC sensor at 10 psig column pressure, 5 mL sample; 37E corresponds to the vent sensor at 10 psig column pressure, 10 mL sample; 37F corresponds to the PPC sensor at 10 psig column pressure, 10 mL sample; 37G corresponds to the vent sensor at 20 psig column pressure, 0 mL sample; 37H corresponds to the PPC sensor at 20 psig column pressure, 0 mL sample; 37I corresponds to the vent sensor at 20 psig column pressure, 5 mL sample; 37J corresponds to the PPC sensor at 20 psig column pressure, 5 mL sample; 37K corresponds to the vent sensor at 20 psig column pressure, 10 mL sample; 37L corresponds to the PPC sensor at 20 psig column pressure, 10 mL sample; 37M corresponds to the vent sensor at 30 psig column pressure, 0 mL sample; 37N corresponds to the PPC sensor at 30 psig column pressure, 0 mL sample; 37O corresponds to the vent sensor at 30 psig column pressure, 5 mL sample; 37P corresponds to the PPC sensor at 30 psig column pressure, 5 mL sample; 37Q corresponds to the vent sensor at 30 psig column pressure, 10 mL sample; 37R corresponds to the PPC sensor at 30 psig column pressure, 10 mL sample; 37S corresponds to the vent sensor at 40 psig column pressure, 0 mL sample; 37T corresponds to the PPC sensor at 40 psig column pressure, 0 mL sample; 37U corresponds to the vent sensor at 40 psig column pressure, 5 mL sample; 37V corresponds to the PPC sensor at 40 psig column pressure, 5 mL sample; 37W corresponds to the vent sensor at 40 psig column pressure, 10 mL sample; and 37X corresponds to the PPC sensor at 40 psig column pressure, 10 mL sample.

The pressure profiles with the in-line needle valve shown in FIGS. 37A-37X were compared against those collected with direct connection as described in Example 8. A number of observations were made. As the needle travels up and down to and from the vial, the pressure drop at the needle is now much greater and effectively drops to atmospheric pressure. This is expected and should not pose any performance problems except that as the needle is withdrawn, chromatography will now be active and may be affected by major pressure disturbances. The PPC pressure regulation is now largely unaffected by the needle operation. Only small pressure excursions are seen at the PPC device as the pressure effectively drops completely at the needle. This would indicate much more stable operation of the PPC device. The pressure downstream of the needle valve (as seen by both the vial and the GC column or transfer line) was lower than the set pressure. The recovery profiles were much smoother with little or no pressure bounce observed. The recovery times were much longer than seen without the needle valve. This result was expected. The measured times are given in Table 11. Although these are much longer, they are still under 60 seconds and are likely still compatible with most methods.

TABLE 11

| | Sample Volume (mL) | | |
|---|---|---|---|
| Pressure (psig) | 0 | 5 | 10 |
| 10 | 50 | 42 | 36 |
| 20 | 46 | 40 | 39 |
| 30 | 33 | 26 | 23 |
| 40 | 27 | 23 | 18 |

Figure 38:
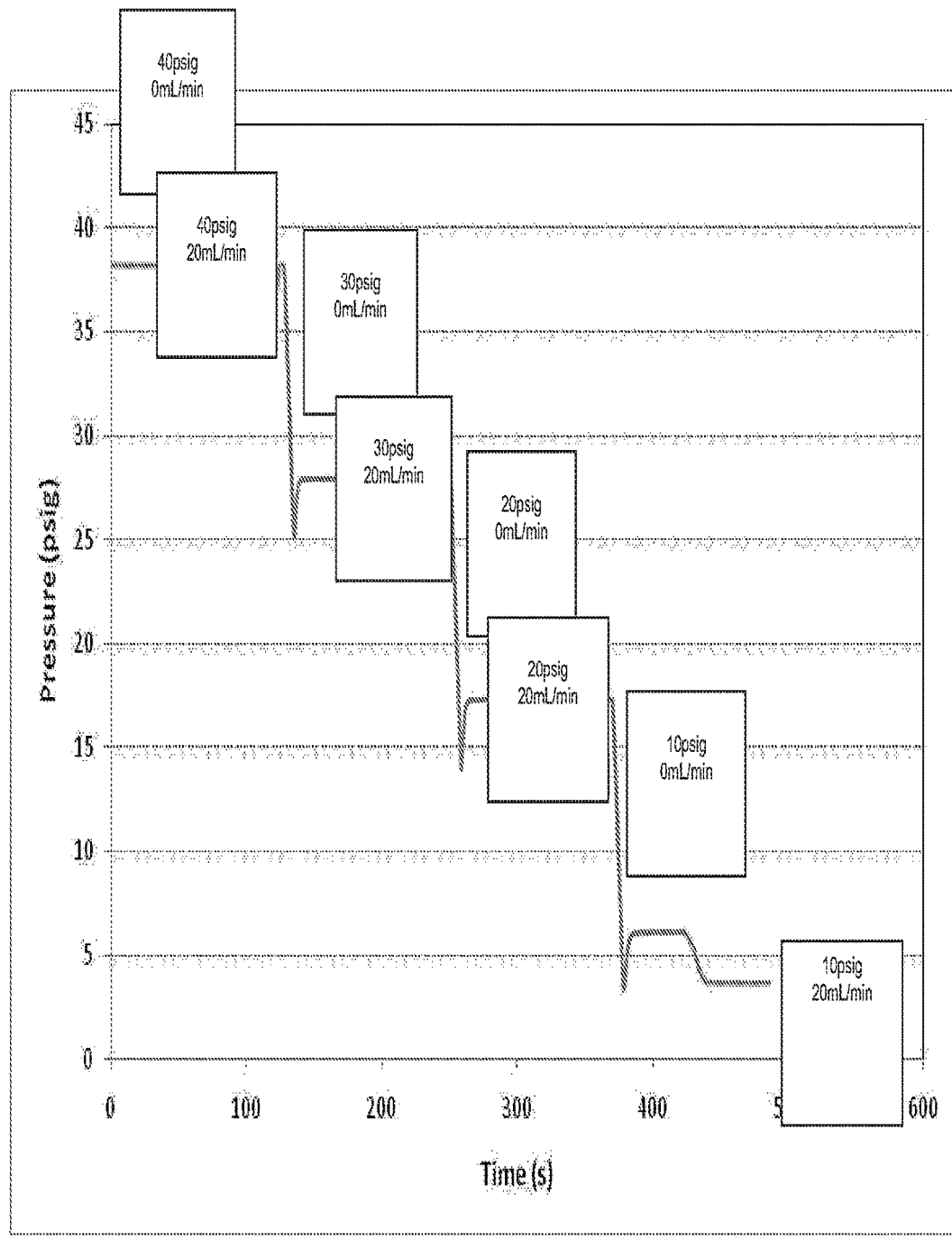
FIG. 38 is a graph showing the results of testing the effect of transfer line flow rate on the pressure applied to the transfer line, in accordance with certain examples.

With the HS system at standby, the pressure was monitored at the vent sensor with the needle valve connected to the column port set to off and to 20 mL/min. This was to assess the effect of transfer line flow rate on the pressure applied to the transfer line. Note that there would be an additional flow rate from the sample head vents. The results of this test are shown in FIG. 38 and Table 12.

TABLE 12

| | Pressure at Column Port (psig) | |
|---|---|---|
| PPC Pressure (psig) | Flow Rate = 0 mL/min | Flow Rate = 20 mL/min |
| 10 | 6.1 | 3.7 |
| 20 | 17.3 | 15.7 |
| 30 | 27.9 | 26.7 |
| 40 | 38.2 | 37.2 |

These data clearly show that there is a significant effect on the pressure applied to the transfer line when varying the flow rate through it.

Example 11

Figure 39:
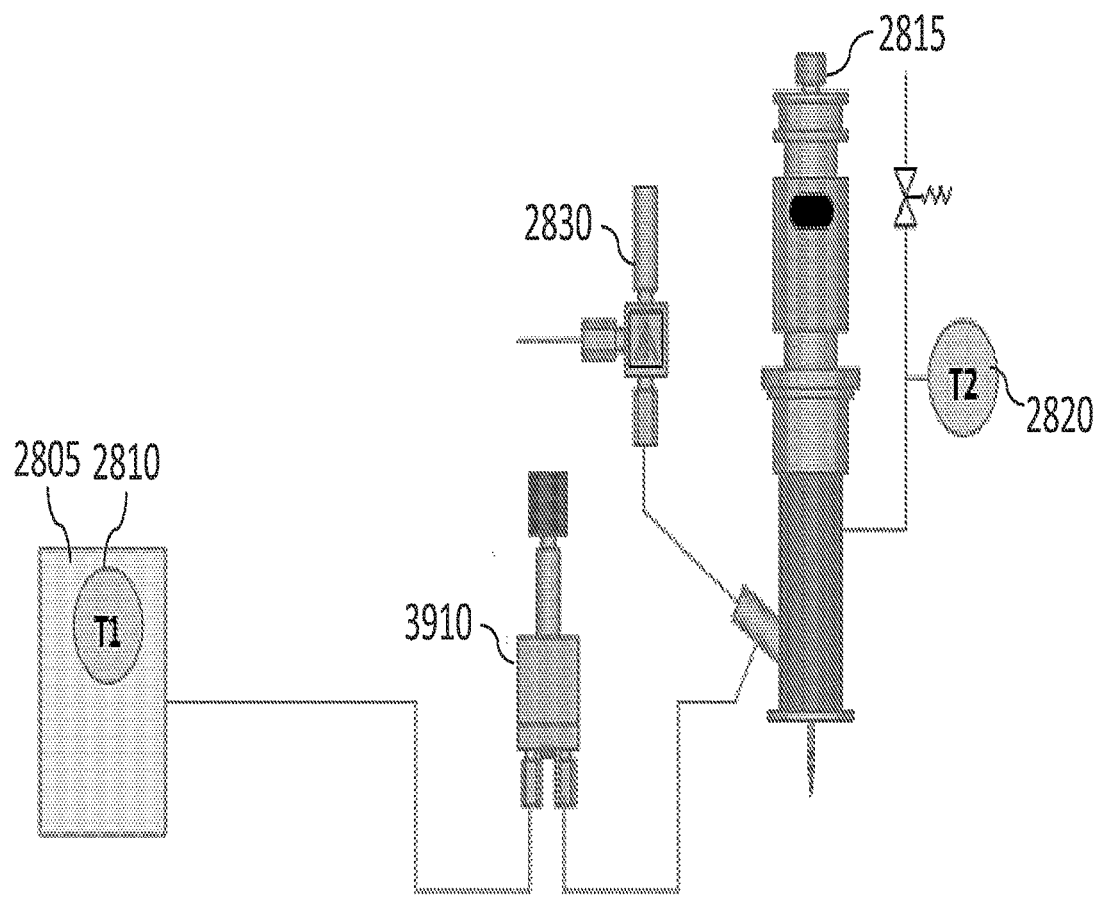
FIG. 39 is a schematic of graph with a system including a mass flow controller, in accordance with certain examples.

The in-line needle valve of Example 10 was removed and replaced with a mechanical mass flow controller (MFC) connected in-line between the PPC regulator and the line feeding the sampling head. A #6 (blue) fit taken off a GC air module was fitted to the MFC; this enabled flow control up to ~450 mL/min hydrogen at 40 psig applied pressure. The MFC acted as a flow limiter feeding the sampling needle. As the pressure at the needle outlet dropped the flow rate would increase but should not increase beyond that set on the MFC. The second needle valve was left connected to the column port on the sampling head to enable the flow rate down the transfer line to be simulated. A schematic of the setup is shown in FIG. 39. The schematic was similar to the setup of FIG. 36 except needle valve 3610 was replaced with MFC 3910.

Figures 40W, 40X:
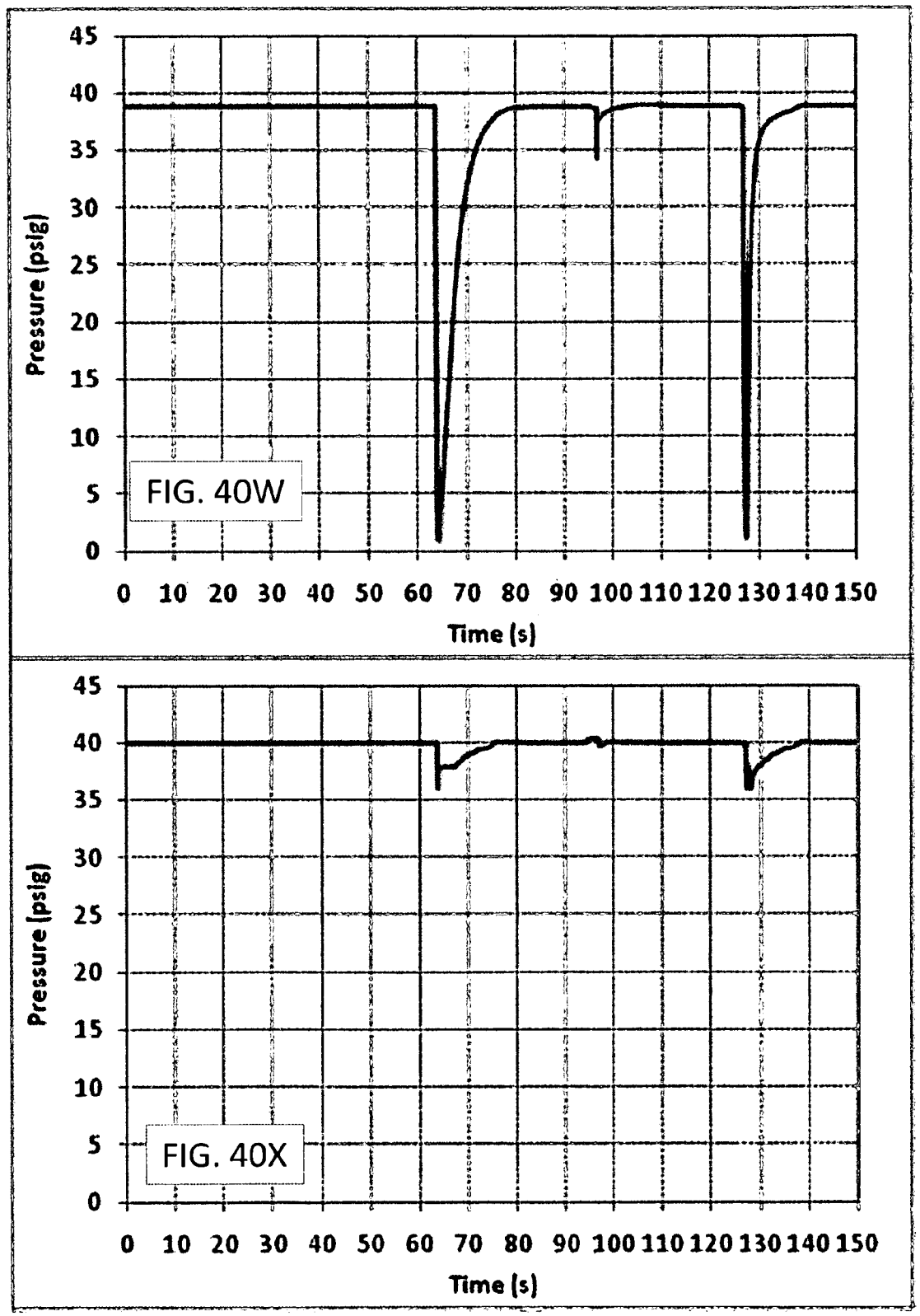

Hydrogen was applied at 40 psig and the mass flow controller was adjusted to deliver 400 mL/min to atmospheric pressure (i.e. with the second needle valve wide open). The second needle valve was turned off and the experimental conditions given in Table 6 were applied. The resultant pressure profiles are shown in FIGS. 40A to 40X. The graphs correspond to: 40A corresponds to the vent sensor at 10 psig column pressure, 0 mL sample; 40B corresponds to the PPC sensor at 10 psig column pressure, 0 mL sample; 40C corresponds to the vent sensor at 10 psig column pressure, 5 mL sample; 40D corresponds to the PPC sensor at 10 psig column pressure, 5 mL sample; 40E corresponds to the vent sensor at 10 psig column pressure, 10 mL sample; 40F corresponds to the PPC sensor at 10 psig column pressure, 10 mL sample; 40G corresponds to the vent sensor at 20 psig column pressure, 0 mL sample; 40H corresponds to the PPC sensor at 20 psig column pressure, 0 mL sample; 40I corresponds to the vent sensor at 20 psig column pressure, 5 mL sample; 40J corresponds to the PPC sensor at 20 psig column pressure, 5 mL sample; 40K corresponds to the vent sensor at 20 psig column pressure, 10 mL sample; 40L corresponds to the PPC sensor at 20 psig column pressure, 10 mL sample; 40M corresponds to the vent sensor at 30 psig column pressure, 0 mL sample; 40N corresponds to the PPC sensor at 30 psig column pressure, 0 mL sample; 40O corresponds to the vent sensor at 30 psig column pressure, 5 mL sample; 40P corresponds to the PPC sensor at 30 psig column pressure, 5 mL sample; 40Q corresponds to the vent sensor at 30 psig column pressure, 10 mL sample; 40R corresponds to the PPC sensor at 30 psig column pressure, 10 mL sample; 40S corresponds to the vent sensor at 40 psig column pressure, 0 mL sample; 40T corresponds to the PPC sensor at 40 psig column pressure, 0 mL sample; 40U corresponds to the vent sensor at 40 psig column pressure, 5 mL sample; 40V corresponds to the PPC sensor at 40 psig column pressure, 5 mL sample; 40W corresponds to the vent sensor at 40 psig column pressure, 10 mL sample; and 40X corresponds to the PPC sensor at 40 psig column pressure, 10 mL sample.

The pressure profiles with the in-line MFC shown in FIGS. 40A-40X were compared against those collected with direct connection shown in Example 8 and with the in-line needle valve as shown in Example 10. The following observations were made. The PPC pressure regulation is largely unaffected by the needle operation. Only small pressure excursions are seen at the PPC device as the pressure effectively drops completely at the needle. This would indicate stable operation of the PPC device. The excursions appear to be slightly greater than seen with the in-line needle valve. The pressure downstream of the needle valve (as seen by both the vial and the GC column or transfer line) was lower than the set pressure. At a setting of 10 psig, this pressure drop was approximately 8 psig. This pressure drop becomes much less significant at higher pressures. This is a much better result than with the in-line needle valve and may be acceptable in practice. The pressure during sampling was closer to that during the chromatography than observed with the in-line needle valve. The recovery profiles (in Section C in FIG. 26) were similar to those seen with the in-line needle valve and much smoother with none of the pressure bounce seen with the direct connection. The vial pressurization times were longer than seen with the direct connection but faster than with the in-line needle valve. The measured times are given in Table 13.

TABLE 13

| Pressure (psig) | Sample Volume (mL) | | |
|---|---|---|---|
| | 0 | 5 | 10 |
| 10 | 38 | 31 | 22 |
| 20 | 26 | 22 | 17 |
| 30 | 23 | 19 | 16 |
| 40 | 21 | 18 | 15 |

Figure 41:
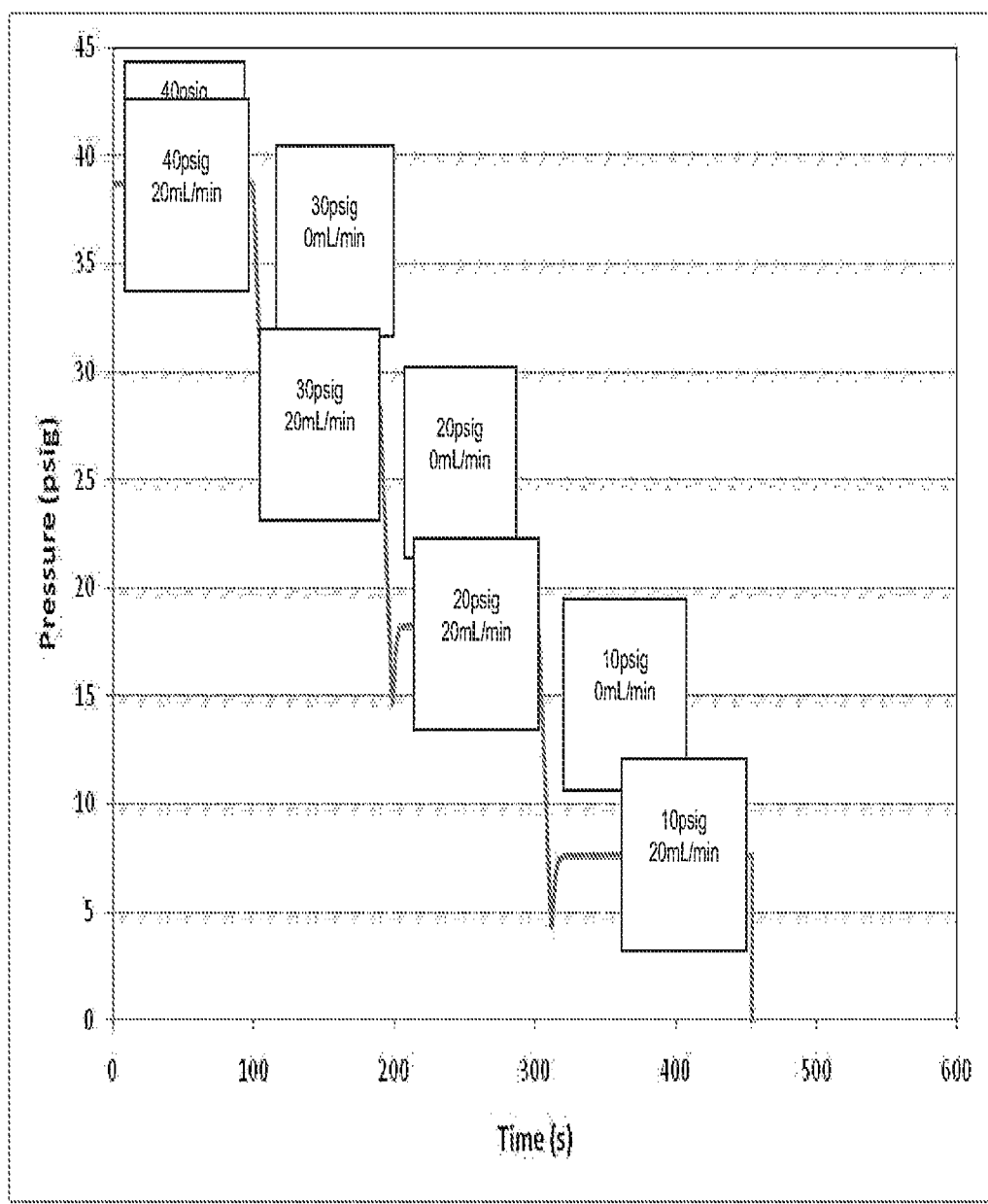
FIG. 41 is a graph showing the effect of flow rate on pressure in the transfer line, in accordance with certain examples.

With the HS system at standby, the pressure was monitored at the vent sensor with the needle valve connected to the column port set to off and to 20 mL/min. This was to assess the effect of transfer line flow rate on the pressure applied to the transfer line. Note that there would be an additional flow rate from the sample head vents. The results of this test are shown in FIG. 41 and Table 14.

TABLE 14

| | Pressure at Column Port (psig) | |
|---|---|---|
| PPC Pressure (psig) | Flow Rate = 0 mL/min | Flow Rate = 20 mL/min |
| 10 | 7.6 | 6.2 |
| 20 | 18.3 | 17.2 |
| 30 | 28.6 | 27.8 |
| 40 | 38.8 | 38.1 |

These data clearly show that there is a still a significant effect on the pressure applied to the transfer line when varying the flow rate through it. The effect is less than that observed with the in-line needle valve.

Example 12

Besides the emissions of hydrogen occurring as the needle moves to and from sample vials, there are other sources of these emissions on the HS systems that must also be considered. There are three flow controllers, based on a small pressure regulator with a fixed internal downstream restrictor, which will also emit hydrogen during use.

The PPC bleed controller: This controller vents a fixed flow rate of carrier gas continually. For PPC pressure regulation to be precise, it needs a continual flow of gas through it. This module supplies 15 mL/min of helium and, based on Table 5, about 32 mL/min of hydrogen. Currently this gas is vented inside the instrument. The PPC bleed controller can be modified to vent gas outside the instrument.

In another configuration, the sample head purge controller can be modified. A flow rate of 32 mL/min of hydrogen will also occur from this source. In this instance, an external vent port is already provided. The flow from this port may be linked to the other vents that need addressing.

In an additional configuration, the headspace trap load controller can be modified. This controller regulates the flow rate of headspace vapor from the vial into the adsorbent trap during sampling. It is set to 50 mL/min for helium. With hydrogen gas, this flow rate was measured at approximately 100 mL/min. This flow rate is excessive. Fortunately, the pressure adjustment screw for this regulator is readily accessible and the user will be able to re-adjust the flow rate back to 50 mL/min. Table 15 shows the results for helium and hydrogen at the normal settings and with hydrogen when the regulator was re-adjusted.

TABLE 15

| Pressure (psig) | He (mL/min) | $H_2$ (mL/min) | $H_2$ Adj. (mL/min) |
|---|---|---|---|
| 5 | 57 | 101 | 59 |
| 10 | 54 | 104 | 55 |
| 15 | 55 | 103 | 55 |
| 20 | 54 | 100 | 52 |
| 25 | 53 | 99 | 52 |
| 30 | 53 | 98 | 52 |
| 35 | 52 | 101 | 52 |
| 40 | 52 | 99 | 51 |
| 45 | 52 | 104 | 52 |

A vent port is provided but resides under the instrument covers. FIG. 139 shows the details. A tube is needed to take this flow of hydrogen gas to the instrument exterior. When introducing elements of the examples disclosed herein, the articles "a," "an," "the" and "said" are intended to mean that there are one or more of the elements. The terms "comprising," "including" and "having" are intended to be open-ended and mean that there may be additional elements other than the listed elements. It will be recognized by the person of ordinary skill in the art, given the benefit of this disclosure, that various components of the examples can be interchanged or substituted with various components in other examples.

Although certain aspects, examples and embodiments have been described above, it will be recognized by the person of ordinary skill in the art, given the benefit of this disclosure, that additions, substitutions, modifications, and alterations of the disclosed illustrative aspects, examples and embodiments are possible.

The invention claimed is:
1. A gas chromatography system comprising:
   a temperature regulated column space configured to receive a chromatography column:
   a sampling system fluidically coupled to the column space and configured to provide sample to the chromatogra- phy column in the column space, the sampling system comprising a flow control device configured to provide release of explosive carrier gas provided by a carrier gas fluid line in less than an explosive amount to void space in the sampling system, in which the sampling system is configured to use hydrogen gas as the explosive carrier gas, and in which the sampling system is configured to reduce sample run time by at least 40% using the explosive carrier gas comprising the hydrogen gas when compared to sample run time using helium as a carrier gas; and
a detector fluidically coupled to the column space and configured to receive analyte from the chromatography column.

2. The gas chromatography system of claim 1, in which the sampling system and the detector each are configured to receive gas from the same carrier gas source.

3. The gas chromatography system of claim 2, in which the detector is configured as a flame detector.

4. The gas chromatography system of claim 3, in which the flame detector is a flame ionization detector.

5. The gas chromatography system of claim 2, in which the detector is configured as a plasma detector.

6. The gas chromatography system of claim 1, in which the flow control device is configured as a sampling device comprising a longitudinal shaft and an effective inner diameter to provide release of the explosive carrier gas in less than the explosive amount to void space in the sampling system.

7. The gas chromatography system of claim 6, in which the effective internal diameter is about 0.15 mm or less.

8. The gas chromatography system of claim 6, in which the sampling device comprises a variable inner diameter with at least some portion comprising an effective inner diameter of about 0.15 mm or less.

9. The gas chromatography system of claim 1, in which the flow control device is configured as an inline restrictor between a carrier gas source and the sampling system, in which the restrictor is configured to provide release of the explosive carrier gas in less than the explosive amount to void space in the sampling system.

10. The gas chromatography system of claim 1, in which the flow control device is configured as a mass flow controller between a carrier gas source and the sampling system, in which the mass flow controller is operative to control the flow rate of explosive carrier gas to provide release of the explosive carrier gas in less than the explosive amount to void space in the sampling system.

11. The gas chromatography system of claim 1, further comprising a fluid transfer line comprising an inner diameter effective to transfer sample to the chromatography column from the sampling system without release of an explosive amount of the explosive carrier gas to void space in the sampling system.

12. A gas chromatography system comprising:
a temperature regulated column space configured to receive a chromatography column:
a sampling system fluidically coupled to the column space and configured to provide sample to the chromatography column in the column space, the sampling system comprising a flow control device configured to provide release of explosive carrier gas provided by a carrier gas fluid line in less than an explosive amount to void space in the sampling system;
a fluid transfer line comprising an inner diameter effective to transfer sample to the chromatography column from the sampling system without release of an explosive amount of the explosive carrier gas to void space in the sampling system, in which the effective inner diameter of the transfer line provides a pressure 15-20 psig at an explosive carrier gas flow rate of 15-20 mL/minute; and
a detector fluidically coupled to the column space and configured to receive analyte from the chromatography column.

13. The gas chromatography system of claim 12, in which the effective inner diameter of the transfer line is about 0.2 mm to about 0.25 mm.

14. The gas chromatography system of claim 12, further comprising at least one active component in the void space of the sampling system, the at least one active component capable of causing explosion of the explosive carrier gas when released in an explosive amount.

15. The gas chromatography system of claim 12 further comprising an explosive carrier gas vent fluidically coupled to the sampling system, the vent configured to provide release of explosive carrier gas from void space in the sampling system to the atmosphere.

16. A method of facilitating use of an explosive carrier gas in a chromatography instrument, the method comprising providing a flow control device configured to provide release of explosive hydrogen carrier gas provided by a carrier gas fluid line in less than an explosive amount to void space in a sampling system, in which the chromatography instrument is configured to reduce sample run time by at least 40% using the hydrogen carrier gas when compared to sample run time using helium as a carrier gas.

17. The method of claim 16, further comprising configuring the flow control device as a sampling device comprising a longitudinal shaft and an effective inner diameter to provide release of the explosive carrier gas in less than the explosive amount to void space in the sampling system.

18. The method of claim 17, further comprising configuring the effective inner diameter to be about 0.15 mm or less.

19. The method of claim 16, further comprising configuring the flow control device as an inline restrictor for insertion between a carrier gas source and a sampling assembly, in which the restrictor is configured to provide release of the explosive carrier gas in less than the explosive amount to void space in the sampling system.

20. The method of claim 16, further comprising configuring the flow control device as a mass flow controller for insertion between a carrier gas source and a sampling assembly, in which the mass flow controller is operative to control the flow rate of explosive carrier gas to provide release of the explosive carrier gas in less than the explosive amount to void space in the sampling system.

* * * * *